US009161967B2

(12) United States Patent
Hart et al.

(10) Patent No.: US 9,161,967 B2
(45) Date of Patent: *Oct. 20, 2015

(54) COMPOSITIONS AND METHODS FOR TREATING THE VERTEBRAL COLUMN

(75) Inventors: Charles E. Hart, Brentwood, TN (US); Samuel E. Lynch, Franklin, TN (US); Conan S. Young, Franklin, TX (US); Dan Perrien, Murfreesboro, TN (US)

(73) Assignee: BioMimetic Therapeutics, LLC, Franklin, TN (US)

( * ) Notice: Subject to any disclaimer, the term of this patent is extended or adjusted under 35 U.S.C. 154(b) by 577 days.

This patent is subject to a terminal disclaimer.

(21) Appl. No.: 12/631,731

(22) Filed: Dec. 4, 2009

(65) Prior Publication Data

US 2010/0183515 A1   Jul. 22, 2010

Related U.S. Application Data

(63) Continuation-in-part of application No. PCT/US2008/065666, filed on Jun. 3, 2008, and a continuation-in-part of application No. PCT/US2007/003582, filed on Feb. 9, 2007, and a continuation-in-part of application No. 11/704,685, filed on Feb. 9, 2007, now Pat. No. 7,799,754.

(60) Provisional application No. 60/933,202, filed on Jun. 4, 2007, provisional application No. 61/026,835, filed on Feb. 7, 2008, provisional application No. 60/817,988, filed on Jun. 30, 2006, provisional application No. 60/859,809, filed on Nov. 17, 2006.

(51) Int. Cl.

| A61K 38/18 | (2006.01) |
|---|---|
| A61K 38/17 | (2006.01) |
| A61K 9/00 | (2006.01) |
| A61K 49/04 | (2006.01) |
| A61L 27/22 | (2006.01) |
| A61L 27/42 | (2006.01) |
| A61L 27/54 | (2006.01) |

(52) U.S. Cl.
CPC ........... *A61K 38/1858* (2013.01); *A61K 9/0024* (2013.01); *A61K 49/0433* (2013.01); *A61K 49/0452* (2013.01); *A61L 27/227* (2013.01); *A61L 27/425* (2013.01); *A61L 27/54* (2013.01); *A61L 2300/202* (2013.01); *A61L 2300/414* (2013.01); *A61L 2300/44* (2013.01); *A61L 2300/45* (2013.01); *A61L 2430/38* (2013.01)

(58) Field of Classification Search
None
See application file for complete search history.

(56) References Cited

U.S. PATENT DOCUMENTS

| 3,943,072 A | 3/1976 | Thomson et al. |
|---|---|---|
| 4,795,467 A | 1/1989 | Piez et al. |
| 4,845,075 A | 7/1989 | Murray et al. |
| 4,861,757 A | 8/1989 | Antoniades et al. |
| 4,874,746 A | 10/1989 | Antoniades et al. |
| RE33,161 E | 2/1990 | Brown et al. |
| 4,904,259 A | 2/1990 | Itay |
| 4,963,145 A | 10/1990 | Takagi et al. |
| 4,975,526 A | 12/1990 | Kuberasampath et al. |
| 5,011,910 A | 4/1991 | Marshall et al. |
| 5,013,649 A | 5/1991 | Wang et al. |
| 5,019,559 A | 5/1991 | Antoniades et al. |
| 5,034,375 A | 7/1991 | Antoniades et al. |
| 5,035,887 A | 7/1991 | Antoniades et al. |
| 5,045,633 A | 9/1991 | Murray et al. |
| 5,053,212 A | 10/1991 | Constantz et al. |
| 5,106,748 A | 4/1992 | Wozney et al. |
| 5,108,922 A | 4/1992 | Wang et al. |
| 5,112,354 A | 5/1992 | Sires |
| 5,116,738 A | 5/1992 | Wang et al. |
| 5,124,316 A | 6/1992 | Antoniades et al. |
| 5,128,321 A | 7/1992 | Murray et al. |
| 5,129,905 A | 7/1992 | Constantz |
| 5,141,905 A | 8/1992 | Rosen et al. |
| 5,149,691 A | 9/1992 | Rutherford |
| 5,165,938 A | 11/1992 | Knighton |
| 5,187,076 A | 2/1993 | Wozney et al. |
| 5,187,263 A | 2/1993 | Murray et al. |
| 5,219,576 A | 6/1993 | Chu et al. |
| 5,219,759 A | 6/1993 | Heldin et al. |
| 5,270,300 A | 12/1993 | Hunziker |
| 5,290,708 A | 3/1994 | Ashihara et al. |

(Continued)

FOREIGN PATENT DOCUMENTS

| EP | 0 289 584 B1 | 11/1988 |
|---|---|---|
| EP | 0 479 799 B1 | 4/1992 |

(Continued)

OTHER PUBLICATIONS

Nevins et al., J. Periodontol., Sep. 2003, vol. 74(9):1282-1292.*
Higashi et al., J. Endod., 1996, vol. 22(6):281-283 (Abstract).*
Chapman et al., J. Bone Joint Surg., 1997, vol. 79(4):495-501.*
Erbe et al., Eur. Spine J. 2001, vol. 10:S141-S146.*
D. T. Gold, Bone, 1996, vol. 18(3):185S-189S.*
Aastrom Biosciences, Inc. (Mar. 23, 2006). "Aastrom Biosciences Received Orphan Drug Designation From the FDA for Proprietary Marrow Cells," located at <http://www.aastrom.com/pressreleases.asp?GetLink=http%3A%2F%2Fwww%2E7ware%...>, last visited on Feb. 24, 2010, 2 pages.

(Continued)

*Primary Examiner* — Xiaozhen Xie
(74) *Attorney, Agent, or Firm* — Hilary Dorr Lang; Patterson Intellectual Property Law, P.C.

(57) ABSTRACT

The present invention relates to compositions and methods useful for treating structures of the vertebral column, including vertebral bodies. In one embodiment, a method for promoting bone formation in a vertebral body comprising providing a composition comprising a PDGF solution and a biocompatible matrix and applying the composition to at least one vertebral body. Promoting bone formation in a vertebral body, according to some embodiments, can increase bone volume, mass, and/or density leading to an increase in mechanical strength of the vertebral body treated with a composition of the present invention.

29 Claims, 5 Drawing Sheets

(56) References Cited

U.S. PATENT DOCUMENTS

| | | |
|---|---|---|
| 5,338,772 A | 8/1994 | Bauer et al. |
| 5,376,636 A | 12/1994 | Rutherford et al. |
| 5,457,093 A | 10/1995 | Cini et al. |
| 5,460,962 A | 10/1995 | Kemp |
| 5,516,896 A | 5/1996 | Murray et al. |
| 5,518,680 A | 5/1996 | Cima et al. |
| 5,531,794 A | 7/1996 | Takagi et al. |
| 5,533,836 A | 7/1996 | Moore |
| 5,549,123 A | 8/1996 | Okuyama et al. |
| 5,599,558 A | 2/1997 | Gordinier et al. |
| 5,629,191 A | 5/1997 | Cahn |
| 5,635,372 A | 6/1997 | Celeste et al. |
| 5,650,176 A | 7/1997 | Lee et al. |
| 5,747,273 A | 5/1998 | Khosravi et al. |
| 5,759,815 A | 6/1998 | Charette et al. |
| 5,783,217 A | 7/1998 | Lee et al. |
| 5,804,176 A | 9/1998 | Grotendorst |
| 5,837,258 A | 11/1998 | Grotendorst |
| 5,853,746 A | 12/1998 | Hunziker |
| 5,866,165 A | 2/1999 | Liu et al. |
| 5,962,028 A | 10/1999 | Constantz |
| 5,965,403 A | 10/1999 | Celeste et al. |
| 5,972,385 A | 10/1999 | Liu et al. |
| 6,018,095 A | 1/2000 | Lerch et al. |
| 6,027,742 A | 2/2000 | Lee et al. |
| 6,030,636 A | 2/2000 | Randolph et al. |
| 6,077,989 A | 6/2000 | Kandel et al. |
| 6,083,910 A | 7/2000 | Kunitani et al. |
| 6,136,029 A | 10/2000 | Johnson et al. |
| 6,180,606 B1 | 1/2001 | Chen et al. |
| 6,214,368 B1 | 4/2001 | Lee et al. |
| 6,221,625 B1 | 4/2001 | Ashihara et al. |
| 6,224,635 B1 | 5/2001 | Ricci et al. |
| 6,280,191 B1 | 8/2001 | Gordon |
| 6,280,478 B1 | 8/2001 | Richter et al. |
| 6,281,195 B1 | 8/2001 | Rueger et al. |
| 6,287,341 B1 | 9/2001 | Lee et al. |
| 6,313,189 B1 | 11/2001 | Wenz et al. |
| 6,316,091 B1 | 11/2001 | Richart et al. |
| 6,331,312 B1 | 12/2001 | Lee et al. |
| 6,346,123 B1 | 2/2002 | McKay |
| 6,398,972 B1 | 6/2002 | Blasetti et al. |
| 6,440,444 B2 | 8/2002 | Boyce et al. |
| 6,451,059 B1 | 9/2002 | Janas et al. |
| 6,465,205 B2 | 10/2002 | Hicks, Jr. |
| 6,468,543 B1 | 10/2002 | Gilbertson et al. |
| 6,541,022 B1 | 4/2003 | Murphy et al. |
| 6,541,037 B1 | 4/2003 | Lee et al. |
| 6,558,307 B2 | 5/2003 | Headley |
| 6,576,015 B2 | 6/2003 | Geistlich et al. |
| 6,586,388 B2 | 7/2003 | Oppermann et al. |
| 6,592,507 B2 | 7/2003 | Jorgensen et al. |
| 6,599,558 B1 | 7/2003 | Al-Lamee et al. |
| 6,613,566 B2 | 9/2003 | Kandler et al. |
| 6,641,552 B1 | 11/2003 | Kingsley et al. |
| 6,649,072 B2 | 11/2003 | Brandt et al. |
| 6,652,473 B2 | 11/2003 | Kaufman et al. |
| 6,663,870 B2 | 12/2003 | Hart et al. |
| 6,710,025 B1 | 3/2004 | Spector |
| 6,739,112 B1 | 5/2004 | Marino |
| 6,743,232 B2 | 6/2004 | Overaker et al. |
| 6,866,991 B2 | 3/2005 | Gilbertson et al. |
| 6,884,428 B2 | 4/2005 | Binette et al. |
| 6,903,078 B1 | 6/2005 | Williams |
| 6,949,251 B2 | 9/2005 | Dalal et al. |
| 6,972,130 B1 | 12/2005 | Lee et al. |
| 6,974,862 B2 | 12/2005 | Ringeisen et al. |
| 7,005,135 B2 | 2/2006 | Janas et al. |
| 7,012,034 B2 | 3/2006 | Heide et al. |
| 7,022,506 B2 | 4/2006 | Brighton et al. |
| 7,041,641 B2 | 5/2006 | Rueger et al. |
| 7,052,518 B2 | 5/2006 | Irie et al. |
| 7,087,540 B2 | 8/2006 | Heide et al. |
| 7,148,209 B2 | 12/2006 | Hoemann et al. |
| 7,192,592 B2 | 3/2007 | Gilbertson et al. |
| 7,192,604 B2 | 3/2007 | Brown et al. |
| 7,250,550 B2 | 7/2007 | Overby et al. |
| 7,357,941 B2 | 4/2008 | Dalal et al. |
| 7,390,498 B2 | 6/2008 | Dalal et al. |
| 7,473,678 B2 | 1/2009 | Lynch |
| 7,491,384 B2 | 2/2009 | Hart et al. |
| 7,597,883 B2 | 10/2009 | Hart et al. |
| 7,799,754 B2 | 9/2010 | Hart et al. |
| 7,943,573 B2 | 5/2011 | Lynch et al. |
| 2001/0014662 A1 | 8/2001 | Rueger et al. |
| 2001/0016646 A1 | 8/2001 | Rueger et al. |
| 2001/0016703 A1 | 8/2001 | Wironen et al. |
| 2001/0020188 A1 | 9/2001 | Sander |
| 2001/0038848 A1 | 11/2001 | Donda et al. |
| 2002/0004225 A1 | 1/2002 | Hart et al. |
| 2002/0006437 A1 | 1/2002 | Grooms et al. |
| 2002/0018796 A1 | 2/2002 | Wironen et al. |
| 2002/0022885 A1 | 2/2002 | Ochi |
| 2002/0037799 A1 | 3/2002 | Li et al. |
| 2002/0082220 A1 | 6/2002 | Hoemann et al. |
| 2002/0082694 A1 | 6/2002 | McKay |
| 2002/0098222 A1 | 7/2002 | Wironen et al. |
| 2002/0115647 A1 | 8/2002 | Halvorsen et al. |
| 2002/0120281 A1 | 8/2002 | Overaker |
| 2002/0127265 A1 | 9/2002 | Bowman et al. |
| 2002/0131989 A1 | 9/2002 | Brown et al. |
| 2002/0193883 A1 | 12/2002 | Wironen |
| 2003/0006025 A1 | 1/2003 | Manini et al. |
| 2003/0049328 A1* | 3/2003 | Dalal et al. .............. 424/602 |
| 2003/0055511 A1* | 3/2003 | Schryver et al. .......... 623/23.5 |
| 2003/0105015 A1 | 6/2003 | Gilbertson et al. |
| 2003/0109000 A1 | 6/2003 | Moore et al. |
| 2003/0109537 A1 | 6/2003 | Turner et al. |
| 2003/0114936 A1 | 6/2003 | Sherwood et al. |
| 2003/0125252 A1 | 7/2003 | Underhill et al. |
| 2003/0152606 A1 | 8/2003 | Gerber |
| 2003/0180376 A1 | 9/2003 | Dalal et al. |
| 2003/0193106 A1 | 10/2003 | Yu et al. |
| 2003/0199615 A1 | 10/2003 | Chaput et al. |
| 2003/0203002 A1 | 10/2003 | Murphy et al. |
| 2003/0224488 A1 | 12/2003 | Fox et al. |
| 2003/0228364 A1 | 12/2003 | Nathan |
| 2003/0232071 A1 | 12/2003 | Gower et al. |
| 2003/0235622 A1 | 12/2003 | Tas |
| 2004/0002770 A1* | 1/2004 | King et al. .............. 623/23.51 |
| 2004/0014727 A1 | 1/2004 | Garrett |
| 2004/0022825 A1 | 2/2004 | Lagow |
| 2004/0033949 A1 | 2/2004 | Bunting et al. |
| 2004/0043031 A1 | 3/2004 | Hart et al. |
| 2004/0064194 A1 | 4/2004 | Irie et al. |
| 2004/0076685 A1 | 4/2004 | Tas |
| 2004/0078077 A1 | 4/2004 | Binette et al. |
| 2004/0078090 A1 | 4/2004 | Binette et al. |
| 2004/0197311 A1 | 10/2004 | Brekke et al. |
| 2004/0224027 A1 | 11/2004 | Spiro et al. |
| 2004/0228870 A9 | 11/2004 | Hart et al. |
| 2004/0230303 A1 | 11/2004 | Gomes et al. |
| 2004/0243133 A1 | 12/2004 | Materna |
| 2004/0265350 A1 | 12/2004 | Sambrook et al. |
| 2005/0027367 A1 | 2/2005 | Heide et al. |
| 2005/0031694 A1 | 2/2005 | Gilbertson et al. |
| 2005/0074481 A1 | 4/2005 | Brekke et al. |
| 2005/0098915 A1 | 5/2005 | Long et al. |
| 2005/0107162 A1 | 5/2005 | Kilby et al. |
| 2005/0107887 A1 | 5/2005 | Knothe Tate et al. |
| 2005/0119754 A1 | 6/2005 | Trieu et al. |
| 2005/0169893 A1 | 8/2005 | Koblish et al. |
| 2005/0170012 A1 | 8/2005 | Dalal et al. |
| 2005/0177203 A1 | 8/2005 | Brighton et al. |
| 2005/0187162 A1 | 8/2005 | Dhanaraj et al. |
| 2006/0029578 A1 | 2/2006 | Hoemann et al. |
| 2006/0084602 A1 | 4/2006 | Lynch |
| 2006/0148024 A1 | 7/2006 | Savage |
| 2006/0149392 A1 | 7/2006 | Hsieh et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154367 A1 | 7/2006 | Kihm et al. |
| 2006/0177475 A1 | 8/2006 | Rueger et al. |

(56) References Cited

U.S. PATENT DOCUMENTS

| | | |
|---|---|---|
| 2006/0190043 A1 | 8/2006 | Brighton et al. |
| 2006/0198939 A1 | 9/2006 | Smith et al. |
| 2006/0205652 A1 | 9/2006 | Zamora et al. |
| 2006/0233853 A1 | 10/2006 | Remington et al. |
| 2006/0247156 A1 | 11/2006 | Vanderby et al. |
| 2006/0257358 A1* | 11/2006 | Wen et al. .............. 424/85.1 |
| 2006/0292198 A1 | 12/2006 | Dalal et al. |
| 2007/0003752 A1 | 1/2007 | Bruce et al. |
| 2007/0026044 A1 | 2/2007 | Bunting et al. |
| 2007/0048381 A1 | 3/2007 | Hart et al. |
| 2007/0053951 A1 | 3/2007 | Gonzalez Santos et al. |
| 2007/0129807 A1 | 6/2007 | Lynch et al. |
| 2007/0160681 A1 | 7/2007 | Park et al. |
| 2007/0190101 A1 | 8/2007 | Yang et al. |
| 2007/0191851 A1 | 8/2007 | Ashammakhi |
| 2007/0207185 A1 | 9/2007 | Hart et al. |
| 2007/0218098 A1 | 9/2007 | Reif et al. |
| 2007/0244484 A1 | 10/2007 | Luginbuehl |
| 2007/0259018 A1 | 11/2007 | McKay |
| 2007/0259814 A1 | 11/2007 | Lynch |
| 2007/0260326 A1 | 11/2007 | Williams et al. |
| 2007/0282455 A1 | 12/2007 | Luginbuehl et al. |
| 2008/0027470 A1 | 1/2008 | Hart et al. |
| 2008/0193424 A1 | 8/2008 | McKale et al. |
| 2008/0200372 A1 | 8/2008 | Ghosh |
| 2009/0054339 A1 | 2/2009 | Marshall et al. |
| 2009/0074753 A1 | 3/2009 | Lynch |
| 2009/0092674 A1 | 4/2009 | Ingram et al. |
| 2009/0130173 A1 | 5/2009 | Behnam et al. |
| 2009/0232890 A1 | 9/2009 | Lynch et al. |
| 2010/0136085 A1 | 6/2010 | Hart et al. |
| 2010/0151025 A1 | 6/2010 | Lynch et al. |
| 2010/0174368 A1 | 7/2010 | Lynch et al. |
| 2010/0196347 A1 | 8/2010 | Kery et al. |
| 2010/0247651 A1 | 9/2010 | Kestler et al. |
| 2011/0020419 A1* | 1/2011 | Yuan et al. .............. 424/602 |
| 2011/0117018 A1 | 5/2011 | Hart et al. |

FOREIGN PATENT DOCUMENTS

| | | |
|---|---|---|
| EP | 0530804 A1 | 3/1993 |
| EP | 0530804 B1 | 3/1993 |
| EP | 0 741 785 B1 | 11/1996 |
| EP | 0 741 785 B2 | 11/1996 |
| EP | 0 896 825 A1 | 2/1999 |
| EP | 0 896 825 B1 | 2/1999 |
| EP | 0 994 694 B1 | 4/2000 |
| EP | 1 025 871 A1 | 8/2000 |
| EP | 1 100 488 B1 | 5/2001 |
| EP | 1 146 897 B1 | 10/2001 |
| EP | 1 234 552 A1 | 8/2002 |
| EP | 1 234 552 B1 | 8/2002 |
| EP | 1 242 129 B1 | 9/2002 |
| EP | 1 374 857 A1 | 1/2004 |
| EP | 1 410 811 A1 | 4/2004 |
| EP | 1 410 811 B1 | 4/2004 |
| EP | 1 464 307 A1 | 10/2004 |
| EP | 1 464 307 B1 | 10/2004 |
| EP | 1 561 481 A2 | 8/2005 |
| EP | 1 561 481 A3 | 8/2005 |
| EP | 1 563 846 A1 | 8/2005 |
| EP | 1 681 087 A2 | 7/2006 |
| EP | 1 681 087 A3 | 7/2006 |
| EP | 1 712 244 A1 | 10/2006 |
| EP | 1 719 531 A2 | 11/2006 |
| EP | 1 719 532 A2 | 11/2006 |
| GB | 2 367 497 A | 4/2002 |
| JP | 7-250688 A | 10/1995 |
| JP | 2003-265592 A | 9/2003 |
| WO | WO-88/03409 A1 | 5/1988 |
| WO | WO-91/15231 A1 | 10/1991 |
| WO | WO-91/18098 A1 | 11/1991 |
| WO | WO-92/09301 A1 | 6/1992 |
| WO | WO-92/16181 A2 | 10/1992 |
| WO | WO-93/00432 A1 | 1/1993 |
| WO | WO-93/05808 A1 | 4/1993 |
| WO | WO-93/08825 A1 | 5/1993 |
| WO | WO-93/09229 A1 | 5/1993 |
| WO | WO-93/16099 A2 | 8/1993 |
| WO | WO-93/20859 A1 | 10/1993 |
| WO | WO-94/01557 A1 | 1/1994 |
| WO | WO-94/05800 A1 | 3/1994 |
| WO | WO-94/15949 A1 | 7/1994 |
| WO | WO-94/15965 A1 | 7/1994 |
| WO | WO-94/15966 A1 | 7/1994 |
| WO | WO-94/21681 A1 | 9/1994 |
| WO | WO-94/22463 A1 | 10/1994 |
| WO | WO-94/26892 A1 | 11/1994 |
| WO | WO-94/26893 A1 | 11/1994 |
| WO | WO-94/28889 A1 | 12/1994 |
| WO | WO-95/01801 A1 | 1/1995 |
| WO | WO-95/01802 A1 | 1/1995 |
| WO | WO-95/07982 A1 | 3/1995 |
| WO | WO-95/10539 A1 | 4/1995 |
| WO | WO-95/16035 A2 | 6/1995 |
| WO | WO-95/16035 A3 | 6/1995 |
| WO | WO-95/18856 A1 | 7/1995 |
| WO | WO-95/20967 A1 | 8/1995 |
| WO | WO-95/28124 A2 | 10/1995 |
| WO | WO-95/28124 A3 | 10/1995 |
| WO | WO-95/28950 A1 | 11/1995 |
| WO | WO-96/01845 A1 | 1/1996 |
| WO | WO-96/02559 A1 | 2/1996 |
| WO | WO-96/13226 A1 | 5/1996 |
| WO | WO-96/16668 A1 | 6/1996 |
| WO | WO-96/17924 A2 | 6/1996 |
| WO | WO-96/17924 A3 | 6/1996 |
| WO | WO-97/13857 A1 | 4/1997 |
| WO | WO-98/00183 A2 | 1/1998 |
| WO | WO-98/00183 A3 | 1/1998 |
| WO | WO-98/40113 A1 | 9/1998 |
| WO | WO-98/41246 A2 | 9/1998 |
| WO | WO-98/41246 A3 | 9/1998 |
| WO | WO-98/51354 A2 | 11/1998 |
| WO | WO-98/51354 A3 | 11/1998 |
| WO | WO-99/30726 A1 | 6/1999 |
| WO | WO-99/38543 A2 | 8/1999 |
| WO | WO-99/38543 A3 | 8/1999 |
| WO | WO-99/67289 A1 | 12/1999 |
| WO | WO-00/04940 A1 | 2/2000 |
| WO | WO-01/32197 A2 | 5/2001 |
| WO | WO-01/32197 A3 | 5/2001 |
| WO | WO-01/35932 A2 | 5/2001 |
| WO | WO-01/35932 A3 | 5/2001 |
| WO | WO-01/41822 A1 | 6/2001 |
| WO | WO-01/57083 A1 | 8/2001 |
| WO | WO-01/60424 A2 | 8/2001 |
| WO | WO-01/60424 A3 | 8/2001 |
| WO | WO-01/66044 A2 | 9/2001 |
| WO | WO-01/66044 A3 | 9/2001 |
| WO | WO-01/66130 A1 | 9/2001 |
| WO | WO-01/68135 A2 | 9/2001 |
| WO | WO-01/68135 A3 | 9/2001 |
| WO | WO-02/00244 A2 | 1/2002 |
| WO | WO-02/00244 A3 | 1/2002 |
| WO | WO-02/00272 A2 | 1/2002 |
| WO | WO-02/00272 A3 | 1/2002 |
| WO | WO-02/36147 A1 | 5/2002 |
| WO | WO-02/062405 A2 | 8/2002 |
| WO | WO-02/062405 A3 | 8/2002 |
| WO | WO-02/067978 A1 | 9/2002 |
| WO | WO-02/070029 A2 | 9/2002 |
| WO | WO-02/070029 A3 | 9/2002 |
| WO | WO-02/102783 A1 | 12/2002 |
| WO | WO-03/006025 A1 | 1/2003 |
| WO | WO-03/043576 A2 | 5/2003 |
| WO | WO-03/043576 A3 | 5/2003 |
| WO | WO-03/065996 A2 | 8/2003 |
| WO | WO-03/065996 A3 | 8/2003 |
| WO | WO-03/070186 A2 | 8/2003 |
| WO | WO-03/070186 A3 | 8/2003 |
| WO | WO-03/071997 A1 | 9/2003 |
| WO | WO-2004/002539 A2 | 1/2004 |

(56) References Cited

FOREIGN PATENT DOCUMENTS

| WO | WO-2004/002539 A3 | 1/2004 |
|---|---|---|
| WO | WO-2004/002539 C1 | 1/2004 |
| WO | WO-2004/010907 A1 | 2/2004 |
| WO | WO-2004/071543 A1 | 8/2004 |
| WO | WO-2004/073563 A2 | 9/2004 |
| WO | WO-2004/073563 A3 | 9/2004 |
| WO | WO-2004/110308 A2 | 12/2004 |
| WO | WO-2004/110308 A3 | 12/2004 |
| WO | WO-2004/110308 C2 | 12/2004 |
| WO | WO-2005/009496 A1 | 2/2005 |
| WO | WO-2005/032461 A2 | 4/2005 |
| WO | WO-2005/032461 A3 | 4/2005 |
| WO | WO-2005/042048 A2 | 5/2005 |
| WO | WO-2005/042048 A3 | 5/2005 |
| WO | WO-2005/046746 A2 | 5/2005 |
| WO | WO-2005/054279 A1 | 6/2005 |
| WO | WO-2005/054279 C1 | 6/2005 |
| WO | WO-2005/072656 A1 | 8/2005 |
| WO | WO-2006/031388 A2 | 3/2006 |
| WO | WO-2006/031388 A3 | 3/2006 |
| WO | WO-2006/034365 A2 | 3/2006 |
| WO | WO-2006/034365 A3 | 3/2006 |
| WO | WO-2006/044334 A2 | 4/2006 |
| WO | WO-2006/044334 A3 | 4/2006 |
| WO | WO-2006/050493 A2 | 5/2006 |
| WO | WO-2006/050493 A3 | 5/2006 |
| WO | WO-2006/093808 A1 | 9/2006 |
| WO | WO-2006/133403 A2 | 12/2006 |
| WO | WO-2006/133403 A3 | 12/2006 |
| WO | WO-2007/061889 A2 | 5/2007 |
| WO | WO-2007/061889 A3 | 5/2007 |
| WO | WO-2007/087436 A2 | 8/2007 |
| WO | WO-2007/087436 A3 | 8/2007 |
| WO | WO-2007/089997 A2 | 8/2007 |
| WO | WO-2007/089997 A3 | 8/2007 |
| WO | WO-2007/090102 A2 | 8/2007 |
| WO | WO-2007/090102 A3 | 8/2007 |
| WO | WO-2007/092622 A2 | 8/2007 |
| WO | WO-2007/092622 A3 | 8/2007 |
| WO | WO-2008/005427 A2 | 1/2008 |
| WO | WO-2008/005427 A3 | 1/2008 |
| WO | WO-2008/073628 A2 | 6/2008 |
| WO | WO-2008/073628 A3 | 6/2008 |
| WO | WO-2008/103690 A2 | 8/2008 |
| WO | WO-2008/103690 A3 | 8/2008 |
| WO | WO-2008/151193 A1 | 12/2008 |
| WO | WO-2009/100454 A1 | 8/2009 |
| WO | WO-2010/030714 A2 | 3/2010 |
| WO | WO-2010/071857 A1 | 6/2010 |
| WO | WO-2010/102266 A1 | 9/2010 |

OTHER PUBLICATIONS

Adalberto et al. "Periodontal Regeneration," *J. Periodontal*, 2005, 76(9):1601-1622.

Adornato, M.C. et al. (Jul. 2007). "The Treatment of Bisphosphonate-Associated Osteonecrosis of the Jaws with Bone Resection and Autologous Platelet-Derived Growth Factors," *Journal of the American Dental Association* 138(7):971-977.

Aghaloo, T.L. DDS MD et al. "Evaluation of Platelet-Rich Plasma in Combination with Anorganic Bovine Bone in the Rabbit Cranium: A Pilot Study," *The International Journal of Oral and Maxillofacial Implants*; 2004, 19:59-65.

Ahn, S-H. et al. (Jun. 2003). "Effect of Recombinant Human Bone Morphogenetic Protein-4 with Carriers in Rat Calvarial Defects," *Journal of Periodontology* 74(6):787-797.

Akita, S. et al. (2004). "Capillary Vessel Network Integration by Inserting a Vascular Pedicle Enhances Bone Formation in Tissue-Engineered Bone Using Interconnected Porous Hydroxyapatite Ceramics," *Tissue Eng.* 10(5/6):789-795.

Almojaly, S. (2008). "The Effect of Bisphosphonate, Alendronate, on Primary Human Alveolar Bone Cells," *Masters Abstracts International* 46(6):61.

American Dental Association (Jun. 2006). Expert Panel Recommendations: Dental Management of Patients on Oral Bisphosphonate Therapy, *Report of the Council of Scientific Affairs*, 14 pages.

Anitua, E. et al. "Autologous platelets as a source of proteins for healing and tissue regeneration," *Thromb Haemost*, 2004, 91:4-15.

Anitua et al. (2005). "Autologous Preparations Rich in Growth Factors Promote Proliferation and Induce VEGF and HGF Production by Human Tendon Cells in Culture," *Journal of Orthopaedic Research* 23:281-286.

Anonymous (2003). "The European Market for Dental Bone Graft Substitutes," *Implant Dentistry* 12(1):3-5.

Antoniades, H.N. et al. (May 27, 1983). "Human Platelet-Derived Growth Factor (PDGF): Amino-Terminal Amino Acid Sequence," *Science* 220:963-965.

Antoniades, H.N. et al. (1985). "Platelet-Derived Growth Factor: A Link to Malignant Transformation," *in Cancer Cells 3: Growth Factors and Transformations*, Fermasico, J. et al.eds., Cold Spring Harbor Laboratory: Cold Spring Harbor, NY, 3:145-151.

Antoniades, H.N. et al. (1991). "Molecular Mechanism of Tissue Repair: Injury Induces Expression of PDGF-B and its Receptor," Abstract No. 2156, *J. Dental Res.* 70:536.

Anusaksathien et al. "Growth Factor Delivery to Re-Engineer Periodontal Tissues," *Current Pharmaceutical Biotechnology*, 2002, vol. 3(2):129-139.

Anusaksathien et al. "Platelet-Derived Growth Factor Gene Delivery Stimulates ex Vivo Gingival Repair," *Tissue Engineering*, 2003, 9(4):745-756.

Anusaksathien et al. "Effect of Sustained Gene Delivery of Platelet-Derived Growth Factor or Its Antagonist (PDGF-1308) on Tissue-Engineered Cementum," *J. Periodontal*, Mar. 2004, 75(3):429-440.

Arm, D.M. et al. "Effect of Controlled Release of Platelet-derived Growth Factor from a Porous Hydroxyapatite Implant on Bone Ingrowth," *Biomaterials*, 1996, 17(7):703-709.

Assael, L.A. (2006). "A Time for Perspective on Bisphosphonates," *J. Oral Maxillofac. Surg.* 64:877-879.

Babbush, C.A. DDS MSCD et al. "An In Vitro and In Vivo Evaluation of Autologous Platelet Concentrate in Oral Reconstruction," *Implant Dent.*, 2003, 12(1):24-34.

Barker, K. et al. (Jun. 2006). "Bisphosphonate-Associated Osteonecrosis of the Jaws: A Guide for the General Dental Practitioner," *Dental Update* pp. 270-275.

Basa, S. et al. (2004). "Alternative Bone Expansion Technique for Immediate Placement of Implants in the Edentulous Posterior Mandibular Ridge: A Clinical Report," *International Journal of Oral & Maxofacial Implants* 19(4):554-558.

Bateman, J. et al. "Platelet-Derived Growth Factor Enhancement of Two Alloplastic Bone Matrices," *J. Periodontol.* (Nov. 2005) 76(11):1833-1841.

Becker. W. et al. (Nov. 1992). "A Comparison of ePTFE Membranes Alone or in Combination with Platelet-Derived Growth Factor and Insulin-Like Growth Factor-I, or Demineralized Freeze Dried Bone in Promoting Bone Formation Around Immediate Extraction Socket Implants: A Study in Dogs," *J. Periodtonol.* 63(11):929-940.

Berlemann, U. et al. (2002). "Adjacent Vertebral Failure After Vertebroplasty," *J. Bone Joint Surg. BR* 84(B):748-752.

Betsholtz, C. et al. (Apr. 24, 1986). "cDNA Sequence and Chromosomal Localization of Human Platelet-Derived Growth Factor A-Chain and its Expression in Tumour Cell Lines," *Nature* 320:695-699.

Biomimetic Therapeutics (Aug. 21, 2002). "Orthovita and BioMimetic Enter into a Supply Agreement," located at <http://biomimetics.com/cgi-bin/aw/acuweb.cgi?s=biomimetics&t=pressreleasedtl.htm&StoryID=82&>, last visited on May 18, 2010, 6 pages.

Biomimetic Therapeutics (May 21, 2003). "BioMimetic Pharmaceuticals, Inc. Closes Series B Venture Funding," located at <http://biomimetics.com/cgi-bin/aw/acuweb.cgi?s=biomimetics&t=pressreleasedtl.htm&StoryID=76&>, last visited on May 18, 2010, 5 pages.

(56) References Cited

OTHER PUBLICATIONS

Biomimetic Therapeutics (Feb. 12, 2004). "BioMimetic Pharmaceuticals Announces Additions to Senior Management Team," located at <http://biomimetics.com/cgi-bin/aw/acuweb.cgi?s=biomimetics&t=pressreleasedtl.htm&StoryID=83&>, last visited on May 18, 2010, 6 pages.

Biomimetic Therapeutics (Jul. 15, 2004). "BioMimetic Pharmaceuticals' Receives Approvable Recommendation from FDA Advisory Panel for *GEM 21S®*," located at <http://biomimetics.com/cgi-bin/aw/acuweb.cgi?s=biomimetics&t=pressreleasedtl.htm&StoryID=78&>, last visited on May 18, 2010, 6 pages.

Biomimetic Therapeutics (Nov. 4, 2004). "BioMimetic Pharmaceuticals Raises $25.7 Million in Series C Financing," located at <http://biomimetics.com/cgi-bin/aw/acuweb.cgi?s=biomimetics&t=pressreleasedtl.htm&StoryID=79&>, last visited on May 20, 2010, 5 pages.

Biomimetic Therapeutics (May 18, 2005). "BioMimetic Pharmaceuticals Raises Additional $11.8 Million in Equity Financing," located at <http://biomimetics.com/cgi-bin/aw/acuweb.cgi?s=biomimetics&t=pressreleasedtl.htm&StoryID=80&>, last visited on May 18, 2010, 6 pages.

Biomimetic Therapeutics (Jul. 13, 2005). "BioMimetic Pharmaceuticals Strengthens Senior Leadership Team," located at <http://biomimetics.com/cgi-bin/aw/acuweb.cgi?s=biomimetics&t=pressreleasedtl.htm&StoryID=81&>, last visited on May 20, 2010, 6 pages.

Biomimetic Therapeutics (Nov. 21, 2005). "BioMimetic Therapeutics Announces FDA Approval of *GEM 21S®* Growth-Factor Enhanced Matrix for the Treatment of Periodontally-Related Bone Defects," located at <http://biomimetics.com/cgi-bin/aw/acuweb.cgi?s=biomimetics&t=pressreleasedtl.htm&StoryID=87&>, last visited on May 18, 2010, 6 pages.

Biomimetic Therapeutics (Mar. 20, 2006). "BioMimetic Therapeutics Initiates Trials with Novel Bio-Active Drug-Device Combination Bone Graft in Two Orthopedic Indications," located at <http://biomimetics.com/cgi-bin/aw/acuweb.cgi?s=biomimetics&t=pressreleasedtl.htm&StoryID=118&>, last visited on May 18, 2010, 6 pages.

Biomimetic Therapeutics (Jun. 7, 2006). "BioMimetic Therapeutics Receives Approval to Market GEM 21S® Growth-Factor Enhanced Matrix in Canada," located at <http://www.biomimetics.com/cgi-bin/acuweb/acuweb.cgi?s=biom&t=NewsDetail.htm&StoryID=166&>, 5 pages.

Biomimetic Therapeutics (Jul. 11, 2006). "BioMimetic Therapeutics Successfully Completes Enrollment in Three Orthopedic Pilot Clinical Trials for GEM OS1™ Bone Graft; Canadian Study Expanded to 60 Patients," located at <http://biomimetics.com/cgi-bin/aw/acuweb.cgi?s=biomimetics&t=pressreleasedtl.htm&StoryID=93&>, last visited on May 18, 2010, 6 pages.

Biomimetic Therapeutics (Sep. 14, 2006). "BioMimetic Therapeutics' Clinical Investigators to Receive Award from American Academy of Periodontolgy for Outstanding Publication; Clinical Investigators to Present Data at Annual AAP Meeting," located at <http://biomimetics.com/cgi-bin/aw/acuweb.cgi?s=biomimetics&t=pressreleasedtl.htm&StoryID=94&>, last visited on May 18, 2010, 6 pages.

Biomimetic Therapeutics (Sep. 27, 2006). "BioMimetic Therapeutics Adds Key Talent to Board of Directors," located at <http://biomimetics.com/cgi-bin/aw/acuweb.cgi?s=biomimetics&t=pressreleasedtl.htm&StoryID=97&>, last visited on May 20, 2010, 6 pages.

Biomimetic Therapeutics (Nov. 6, 2006). "BioMimetic Therapeutics' Clinical Investigator Highlights Results of Orthopedic Clinical Trial Canada," located at <http://biomimetics.com/cgi-bin/aw/acuweb.cgi?s=biomimetics&t=pressreleasedtl.htm&StoryID=101&>, last visited on May 18, 2010, 7 pages.

Biomimetic Therapeutics (Dec. 13, 2006). "BioMimetic Therapeutics Announces Positive Results; GEM OS1 Stimulates Bone Healing Comparable to Autograft," located at <http://biomimetics.com/cgi-bin/aw/acuweb.cgi?s=biomimetics&t=pressreleasedtl.htm&StoryID=104&>, last visited on May 18, 2010, 7 pages.

Biomimetic Therapeutics (Jan. 25, 2007). "BioMimetic Therapeutics Reports Positive Clinical Results Using *GEM OS® 1* to Treat Distal Radius Fractures," located at <http://biomimetics.com/cgi-bin/aw/acuweb.cgi?s=biomimetics&t=pressreleasedtl.htm&StoryID=105&>, last visited on May 18, 2010, 6 pages.

Biomimetic Therapeutics (Feb. 21, 2007). "BioMimetic Therapeutics Receives Orphan Drug Designation for rhPDGF-BB Treatment of Osteonecrosis of the Jaw," located at < http://biomimetics.com/cgi-bin/aw/acuweb.cgi?s=biomimetics&t=pressreleasedtl.htm&StoryID=112&>, last visited on Apr. 5, 2010, 6 pages.

Biomimetic Therapeutics (Mar. 28, 2007). "BioMimetic Therapeutics Reports 2006 Fourth Quarter and Year-End Results; Company Receives Clearance to Initiate Enrollment in GEM OS1 US Pivotal Trial," located at <http://biomimetics.com/cgi-bin/aw/acuweb.cgi?s=biomimetics&t=pressreleasedtl.htm&StoryID=113&>, last visited on May 18, 2010, 8 pages.

Biomimetic Therapeutics (May 10, 2007). "BioMimetic Therapeutics to Report 2007 First Quarter Financial Results on May 14," located at <http://biomimetics.com/cgi-bin/aw/acuweb.cgi?s=biomimetics&t=pressreleasedtl.htm&StoryID=111&>, last visited on May 18, 2010, 4 pages.

Biomimetic Therapeutics (May 14, 2007). "BioMimetic Therapeutics Reports 2007 First Quarter Results; Company Added to NASDAQ Biotechnology Index," located at <http://biomimetics.com/cgi-bin/aw/acuweb.cgi?s=biomimetics&t=pressreleasedtl.htm&StoryID=116&>, last visited on May 18, 2010, 7 pages.

Biomimetic Therapeutics (Jun. 7, 2007). "BioMimetic Therapeutics Initiates Enrollment in E.U. Registration Trial for GEM OS®1 Bone Graft; U.S. GEM OS1 Pivotal Study Protocol Amended to Allow Shorter Follow-Up Time and More Patients," located at <http://biomimetics.com/cgi-bin/aw/acuweb.cgi?s=biomimetics&t=pressreleasedtl.htm&StoryID=119&>, last visited on May 18, 2010, 6 pages.

Biomimetic Therapeutics (Jul. 13, 2007). "BioMimetic Therapeutics' Clinical Investigator Presents Positive Interim Data on U.S. and Canadian Foot and Ankle Clinical Trials," located at <http://biomimetics.com/cgi-bin/aw/acuweb.cgi?s=biomimetics&t=pressreleasedtl.htm&StoryID=123&>, last visited on May 18, 2010, 8 pages.

Biomimetic Therapeutics (Aug. 14, 2007). "BioMimetic Therapeutics Reports 2007 Second Quarter Results," located at <http://biomimetics.com/cgi-bin/aw/acuweb.cgi?s=biomimetics&t=pressreleasedtl.htm&StoryID=125&>, last visited on May 18, 2010, 7 pages.

Biomimetic Therapeutics (Nov. 13, 2007). "BioMimetic Therapeutics Reports 2007 Third Quarter Results," located at <http://biomimetics.com/cgi-bin/aw/acuweb.cgi?s=biomimetics&t=pressreleasedtl.htm&StoryID=127&>, last visited on May 18, 2010, 7 pages.

Biomimetic Therapeutics (Dec. 13, 2007). "BioMimetic Therapeutics reports Positive Clinical Results for GEM OS®1 in Canadian Foot and Ankle Fusion Study; Clinical Success Rate of 90% Achieved in High Risk Patient Population," located at <http://biomimetics.com/cgi-bin/aw/acuweb.cgi?s=biomimetics&t=pressreleasedtl.htm&StoryID= 131 &>, last visited on May 18, 2010, 6 pages.

Biomimetic Therapeutics (Dec. 17, 2007). "BioMimetic Therapeutics to Sell Remaining Dental Business for Additional $40 Million Cash Plus Continuation of Royalties; Company to Focus on Orthopedics, Spine and Sports Medicine," located at <http://biomimetics.com/cgi-bin/aw/acuweb.cgi?s=biomimetics&t=pressreleasedtl.htm&StoryID=149&>, last visited on May 18, 2010, 7 pages.

Biomimetic Therapeutics (Feb. 29, 2008). "BioMimetic Therapeutics, Inc. to Highlight Clinical and Preclinical Activities at ORS and AAOS Meetings," located at http://biomimetics.com/cgi-bin/aw/acuweb.cgi?s=biomimetics&t=pressreleasedtl.htm&StoryID=136&>, last visited on May 18, 2010, 6 pages.

(56) References Cited

OTHER PUBLICATIONS

Biomimetic Therapeutics (Mar. 7, 2008). "BioMimetic Therapeutics, Inc. Provides Updates on Clinical and Preclinical Activities; Company Receives Go Ahead from Health Canada to File GEM OS1 DLA," located at <http://biomimetics.com/cgi-bin/aw/acuweb.cgi?s=biomimetics&t=pressreleasedtl.htm&StoryID=138&>, last visited on May 18, 2010, 6 pages.
Biomimetic Therapeutics (Mar. 12, 2008). "BioMimetic Therapeutics Reports 2007 fourth Quarter and Year-End Results; Year Marked by Strong Cash Position, Positive Orthopedic Data and Progressing Clinical Trials," located at <http://biomimetics.com/cgi-bin/aw/acuweb.cgi?s=biomimetics&t=pressreleasedtl.htm&StoryID=137&>, last visited on May 18, 2010, 8 pages.
Biomimetic Therapeutics (Aug. 11, 2008). "BioMimetic Therapeutics Reports 2008 Second Quarter Results; Positive Results Achieved with Augment™ Injectable Bone Graft to Enhance Healing in Foot and Ankle Fusions," located at <http://biomimetics.com/cgi-bin/aw/acuweb.cgi?s=biomimetics&t=pressreleasedtl.htm&StoryID= 151&>, last visited on May 18, 2010, 8 pages.
Biomimetic Therapeutics (Sep. 23, 2008). "BioMimetic Therapeutics Announces No Changes Requested by Independent Data Monitoring Committee to Pivotal Trial Design for Augment™ Bone Graft; 268 of 396 Patients Enrolled to Date in U.S. Pivotal Trial," located at <http://biomimetics.com/cgi-bin/aw/acuweb.cgi?s=biomimetics&t=pressreleasedtl.htm&StoryID=153&>, last visited on May 18, 2010, 7 pages.
Biomimetic Therapeutics (Oct. 29, 2008). "BioMimetic Therapeutics Reports Promising Clinical Results Using Augment Injectable Bone Graft to Treat Distal Radius Fractures; Enrollment in North American Augment Pivotal Trial Accelerates; 314 of 396 Patients Enrolled," located at <http://biomimetics.com/cgi-bin/aw/acuweb.cgi?s=biomimetics&t=pressreleasedtl.htm&StoryID=159&>, last visited on May 18, 2010, 6 pages.
Biomimetic Therapeutics (Nov. 10, 2008). "BioMimetic Therapeutics Reports 2008 Third Quarter Results," located at <http://biomimetics.com/cgi-bin/aw/acuweb.cgi?s=biomimetics&t=pressreleasedtl.htm&StoryID=157&>, last visited on May 18, 2010, 8 pages.
Biomimetic Therapeutics (Nov. 21, 2008). "BioMimetic Therapeutics, Inc. Announces Patent Allowance from the United States Patent and Trademark Office for PDGF Compositions Patent; Expanded Protection for Augment™, Augment™ Injectable and GEM 21S® Until 2024," located at <http://biomimetics.com/cgi-bin/aw/acuweb.cgi?s=biomimetics&t=pressreleasedtl.htm&StoryID=163&>, last visited on May 18, 2010, 5 pages.
Biomimetic Therapeutics (Dec. 11, 2008). "BioMimetic Therapeutics, Inc. Achieves Patient Enrollment Target (396) in North American Pivotal Study for Augment™ Bone Graft," located at <http://biomimetics.com/cgi-bin/aw/acuweb.cgi?s=biomimetics&t=pressreleasedtl.htm&StoryID=169&>, last visited on May 18, 2010, 5 pages.
Biomimetic Therapeutics (Jan. 7, 2009). "BioMimetic Therapeutics, Inc. Closes Enrollment with 436 Patients in North American Pivotal Study for Augment™ Bone Graft; Company Will File Modular PMA with the FDA Beginning This Spring," located at <http://biomimetics.com/cgi-bin/aw/acuweb.cgi?s=biomimetics&t=pressreleasedtl.htm&StoryID=168&>, last visited on May 18, 2010, 5 pages.
Biomimetic Therapeutics (Feb. 19, 2009). "BioMimetic Therapeutics, Inc. to Highlight Pre-Clinical and Clinical Activities at ORS and AAOS Meetings; Company to Host an Analyst and Investor Meeting Feb. 26," located at <http://biomimetics.com/cgi-bin/aw/acuweb.cgi?s=biomimetics&t=pressreleasedtl.htm&StoryID=154&>, last visited on May 18, 2010, 6 pages.
Biomimetic Therapeutics (Mar. 12, 2009). "BioMimetic Therapeutics Reports 2008 Fourth Quarter and Year End Results," located at <http://biomimetics.com/cgi-bin/aw/acuweb.cgi?s=biomimetics&t=pressreleasedtl.htm&StoryID=160&>, last visited on May 18, 2010, 11 pages.
Biomimetic Therapeutics (May 7, 2009). "BioMimetic Therapeutics Releases 2009 First Quarter Financial Results," located at <http://biomimetics.com/cgi-bin/aw/acuweb.cgi?s=biomimetics&t=pressreleasedtl.htm&StoryID=167&>, last visited on May 18, 2010, 8 pages.
Biomimetic Therapeutics (Aug. 10, 2009). "BioMimetic Therapeutics Reports 2009 Second Quarter Earnings Results," located at <http://biomimetics.com/cgi-bin/aw/acuweb.cgi?s=biomimetics&t=pressreleasedtl.htm&StoryID=185&>, last visited on May 18, 2010, 8 pages.
Biomimetic Therapeutics (Oct. 13, 2009). "BioMimetic Announces Positive Top-Line Data from its Augment Bone Graft North American Pivotal Trial; Augment Demonstrates Non-Inferiority to Autograft," located at < http://biomimetics.com/cgi-bin/aw/acuweb.cgi?s=biomimetics&t=pressreleasedtl.htm&StoryID=188&>, last visited on May 18, 2010, 8 pages.
Biomimetic Therapeutics (Nov. 3, 2009). "BioMimetic Therapeutics Receives First Orthopedic Marketing Approval for Augment Bone Graft," located at <http://biomimetics.com/cgi-bin/aw/acuweb.cgi?s=biomimetics&t=pressreleasedtl.htm&StoryID=190&>, last visited on May 18, 2010, 6 pages.
Biomimetic Therapeutics (Nov. 5, 2009). "BioMimetic Therapeutics Reports 2009 Third Quarter Earnings Results; Company's Second Orthopedic Product Candidate Enters Pivotal Trial for Foot and Ankle Fusion Indications," located at <http://biomimetics.com/cgi-bin/aw/acuweb.cgi?s=biomimetics&t=pressreleasedtl.htm&StoryID= 191 &>, last visited on May 18, 2010, 8 pages.
Biomimetic Therapeutics (Feb. 1, 2010). "BioMimetic Therapeutics, Inc. Patent Portfolio Further Strengthened" located at <http://biomimetics.com/cgi-bin/aw/acuweb.cgi?s=biomimetics&t=pressreleasedtl.htm&StoryID=199&>, last visited on May 18, 2010, 5 pages.
Biomimetic Therapeutics (Mar. 4, 2010). "BioMimetic Therapeutics, Inc. to Highlight Pre-Clinical and Clinical Activities at ORS and AAOS Meetings; Company to Host Analyst and Investor Meeting on Mar. 11," located at <http://biomimetics.com/cgi-bin/aw/acuweb.cgi?s=biomimetics&t=pressreleasedtl.htm&StoryID=201&>, last visited on May 18, 2010, 6 pages.
Biomimetic Therapeutics (Mar. 9, 2010). "BioMimetic Therapeutics Presents Promising Pre-Clinical Sports Medicine data at the 2010 ORS Meeting," located at <http://biomimetics.com/cgi-bin/aw/acuweb.cgi?s=biomimetics&t=pressreleasedtl.htm&StoryID=202&>, last visited on May 18, 2010, 6 pages.
Biomimetic Therapeutics (Mar. 11, 2010). "BioMimetic Therapeutics Reports 2009 Fourth Quarter and Year End Earnings Results; Company Releases Additional Pivotal Data on Augment," located at <http://biomimetics.com/cgi-bin/aw/acuweb.cgi?s=biomimetics&t=pressreleasedtl.htm&StoryID=203&>, last visited on May 18, 2010, 11 pages.
Biomimetic Therapeutics (Mar. 12, 2010). "Morningstar® Document ResearchSM Form 10-K," United States Securities and Exchange Commission Annual Report, located at <http://investor.biomimetics.com/phoenix.zhtml?c=196896&p=irol-sec>, last visited on May 19, 2010, 247 pages.
Björkenheim, J-M. (1989). "Structure and Function of the Rabbit's Supraspinatus Muscle After Resection of its Tendon," *Acta Orthop. Scand.* 60(4):461-463.
Boileau, P. et al. (Jun. 2005). "Arthroscopic Repair of Full-Thickness Tears of the Supraspinatus: Does the Tendon Really Heal?" *J. Bone Joint Surg. Am.* 87-A(6):1229-1240.
Bolander, "Regulation of Fracture Repair by Growth Factors," *P.S.E.B.M.*, 1992, 200:165-170.
Bonfini, T. et al. (Jan. 1, 2006). "Autologous Marrow and Platel Gel in Bone Tissue Regeneration," *Cytotherapy* 8(1), Abstract No. 239, 2 pages.
Bora, F.W. Jr. et al. (Aug. 1987). "Joint Physiology, Cartilage Metabolism, and the Etiology of Osteoarthritis," *Hand Clin.* 3(3):325-336.
Boyden, E.M. et al. (Aug. 1995). "Late Versus Early Repair of Achilles Tendon Rupture: Clinical and Biomechanical Evaluation," *Clin. Orthop. Relat. Res.* 317:150-158.
Braddock, M. et al. (Oct. 2001). "Born Again Bone: Tissue Engineering for Bone Repair," *News Physiool. Sci.* 16:208-213.

(56) References Cited

OTHER PUBLICATIONS

Buser, D. et al. (1991). "Effects of Growth Factors on Bone Regeneration Around Titanium Implants," Abstract No. 282, *J. Dental Res.* 70:301.

Business Wire (Dec. 15, 2000). "Orthovita Recieves U.S. FDA Clearance for VITOSS Scaffold, the First Engineered 90% Porous Beta-Tricalcium Phosphate; Another Milestone Achievement This Year for Orthovita," located at <http://www.highbeam.com/doc/1G1-680271 13.html>, last visited on Apr. 26, 2010, 3 pages.

Business Wire (May 29, 2002). "Orthovita Issued Patent for Biomaterials Platform Designed to Facilitate Natural Mechanism of Action in Bone Healing," located at <http://www.highbeam.com/doc/1G1-86413645.html>, last visited on Jun. 17, 2010, 3 pages.

Camargo et al. "Platelet-rich Plasma and Bovine Porous Bone Mineral Combined with Guided Tissue Regeneration in the Treatment of Intrabony Defects in Humans," *J Periodont Res* 2002, 37:300-306.

Camargo, L.V. PM et al. "Effectiveness of a Combination of Platelet-Rich Plasma, Bovine Porous Bone Mineral and Guided Tissue Regeneration in the Treatment of Mandibular Grade II Molar Furcations in Humans," *J. Clin. Periodontol*, 2003, 30:746-751.

Camelo et al. "Clinical, radiographic, and histologic evaluation of human periodontal defects treated with bio-oss and bio-guide," *International Journal of Periodontics and Restorative Dentistry*, 1998, 18(4):321-332.

Camelo et al. "Periodontal regeneration with an autogenous bone-bio-oss composite graft and a bio-guide membrane," *International Journal of Periodontics and Restorative Dentistry.* 2001, 21(2):109-120.

Camelo, M. et al. (Nov. 3, 2003). "Periodontal Regeneration in Human Class II Furcations Using Purified Recombinant Human Platelet-Derived Growth Factor-BB (rhPDGF-BB) with Bone Allograft," *International Journal of Periodontics & Restorative Dentistry* 23(3):213-225.

Canalis, "Effect of Growth Factors on Bone Cell Replication and Differentiation," *Clinical Orthopedics and Related Research*, Mar. 1985, 193:246-263.

Carpio, L. et al. (Nov. 2000). "Guided Bone Regeneration Around Endosseous Implants with Anorganic Bovine Bone Material. A Randomized Controlled Trial Comparing Bioabsorbable Versus Non-Resorbable Barriers," *J. Periodontol.* 71(1):1743-1749.

Catalano, L. et al. (2006). "Bisphoshonates and Risk of Osteonecorisis of the Jaws," *Haema* 9(3):410-414.

Cenni, E. et al. (2003, e-pub. Oct. 1, 2003). "Plasma Levels of Coagulation Inhibitors, Fibrinolytic Markers and Platelet-Derived Growth Factor-AB in Patients with Failed Hip Prosthesis," *Acta Orthop. Scand.* 74(5):559-564.

Cenni, E. et al. (2005, e-pub. Feb. 1, 2005). "Plasma Levels of Platelet-Derived Growth Factor BB and Transforming Growth Factor in Patients with Failed Hip Protheses," *Acta Orthopaedica* 76(1):64-66.

Chalmers, J. (Jun. 2000). "Review Article: Treatment of Achilles Tendon Ruptures," *J. Orthop. Surg.* 8(1):97-99.

Chan, B.P. et al. (Jul. 2006). "Supplementation-time Dependence of Growth Factors in Promoting Tendon Healing," *Clinical Orthopaedics and Related Research* 448:240-247.

Chen et al. "Adenoviral Gene Transfer of PDGF Downregulates Gas Gene Product PDGFR and Prolongs ERK and AktIPKB Activation," *Am J Physiol Cell Physiol.*, Mar. 2002, 282:C538-C544.

Chiandussi, S. et al. (2006). "Clinical and Diagnostic Imaging of Bisphosphonate-Associated Osteonecrosis of the Jaws," *Dentomaxillofacial Radiology* 35:236-243.

Chin, M. (1995). "Distraction Osteogenesis in Maxillofacial Surgery," Chapter 9 in *Tissue Engineering: Applications in Maxillofacial Surgery and Periodontics*, Lynch, S.E. et al. eds., Quintessence Publishing, pp. 147-159.

Cho et al. (Jun. 1995). "Platelet Derived Growth Factor—Modulated Guided Tissue Regenerative Therapy," *J. Periodontol.* 66(6):522-530.

Clain, M.R. et al. (Oct. 1992). "Achilles Tendinitis," *Foot Ankle Int.* 13(8):482-487.

Clergeau, L.P. et al. (Feb. 1996). "Healing Response to Anorganic Bone Implantation in Periodontal Intrabony Defects in Dogs Part 1. Bone Regeneration. A Microradiographic Study," *J. Periodontool.* 67(2):140-149.

Cochran et al. "Effects of Platelet-Derived Growth Factor Isoforms on Calcium Release From Neonatal Mouse Calvariae," *Bone*, 1993, 14:53-58.

Coleman, S.H. et al. (Dec. 2003). "Chronic Rotator Cuff Injury and Repair Model in Sheep," *The Journal of Bone and Joint Surgery* 85-A(12):2391-2402.

Collins, T. et al. (Aug. 22, 1985). "Cultured Human Endothelial Cells Express Platelet-Derived Growth Factor B Chain: cDNA Cloning and Structural Analysis," *Nature* 316:748-750.

Convery, F.R. et al. (Jan.-Feb. 1972). "The Repair of Large Osteochondral Defects. An Experimental Study in Horses," *Clin. Orthop. Relat. Res.* 82:253-262.

Cooke et al. "Effect of rhPDGR-BB Delivery on Mediators of Periodontal Wound Repair," *Tissue Engineering*, 2006, 12(6):1441-1450.

Costa, M.A. et al. (Jul. 2006). "Tissue Engineering of Flexor Tendons: Optimization of Tenocyte Proliferation Using Growth Factor Supplementation," *Tissue Eng.* 12(7):1937-1943.

Courneya, J-P. et al. (2010). "Normal and Diseased Primary Human Tenocytes in Response to rhPDGF-BB," Poster No. 1118, *56th Annual Meeting of the Orhopaedic Research Society*, located at < http://www.ors.org/web/Transactions/56/1118.pdf>, last visited on Feb. 23, 2010, 1 page.

Creaney, L. et al. (May 2008, e-pub. Nov. 5, 2007). "Growth Factor Delivery Methods in the Management of Sports Injuries: The State of Play," *Br. J. Sports Med.* 42(5):314-320, Abstract Only.

Curt et al. (Jan. 19, 2007). "Treatment of Avascular Osteonecorsis of the Mandible in Cancer Patients with a History of Bisphosphonate Therapy by Combining Bone Resection and Autologous Platelet-Rich Plasma: Report of 3 Cases," *Journal of Oral and Maxillofacial Surgery* 65(2):349-355.

Dalla-Favera, R. et al. (Nov. 12, 1982). "Chromosomal Localization of the Human Homolog (*c-sis*) of the Simian Sarcoma Virus onc Gene," *Science* 218:686-688.

Daniels, T.R. et al. (2008). "Application of rhPDGF-BB in Foot and Ankle Fusion Procedures," Chapter 19 in *Tissue Engineering: Applications in Maxillofacial Surgery and Periodontics*, Second Edition, Lynch, S.E. et al. eds., Quintessence Publishing Co.: Hanover Park, IL, pp. 267-275.

Dines J.S. et al. (Sep./Oct. 2007). "Tissue Engineering and Rotator Cuff Tendon Healing," *J. Shoulder Elbow Surg.* 16(5S):204S-207S.

Dines, J.S. et al. (Sep./Oct. 2007). "The Effect of Growth on Differentiation Factor-5-Coated Sutures on Tendon Repair in a Rat Model," *J. Shoulder Elbow Surg.* 16(5S):215S-221S.

Donnelly, B.P. et al. (Jul. 2006). "Nucleotide Structure of Equine Platelet-Derived Growth Factor-A and -B and Expression in Horses with Induced Acute Tendinitis," *Am. J. Vet. Res.* 67(7):1218-1225, Abstract Only.

Doolittle et al. (Jul. 15, 1983). "Simian Sarcoma Virus onc Gene *v-sis*, Is Derived from the Gene (or Genes) Encoding a Platelet-Derived Growth Factor," *Science* 221:275-277.

Duffy, F.J. et al. (Jul. 1995). "Growth Factors and Canine Flexor Tendon Healing: Initial Studies in Uninjured and Repair Models," *The Journal of Hand Surgery* 20A(4):645-649.

Dunn, C.A. et al. (Feb. 2005, e-pub. Nov. 6, 2004). "BMP Gene Delivery for Alveolar Bone Engineering at Dental Implant Defects," *Molecular Therapy* 11(2):294-299.

Easley, M.E. et al. (May 2000). "Isolated Subtalar Arthodesis," *JBJS* 82-A(5):613-624.

Eastell, R. et al. (Mar. 1991). "Classification of Vertebral Fractures," *J. Bone Miner. Res.* 6(3):207-215.

Erikson, a. et al. (Nov. 5, 1991). "Induction of Platelet-Derived Growth Factor α- and β-Receptor mRNA and Protein by Platelet Derived Growth Factor BB," *J. Biol. Chem.* 266(31):21138-21144.

Fagan, M.C. et al. (2008). "Simultaneous Augmentation of Hard and Soft Tissues for Implant Site Preparation Using Recombinant Human Platelet-Derived Growth Factor: A Human Case Report," *Int. J. Periodontics Restorative Dent.* 28(1):37-43.

(56) References Cited

OTHER PUBLICATIONS

Farrugia, M.C. et al. (Jan. 2006). "Osteonecrosis of the Mandible or Maxilla Associated with the Use of New Generation Bisphosphonates," *The Laryngoscope* 116:115-120.

Feldman, D. et al. (Sep. 1998). "In a Time of Change, Orthopedics Sector is Marked by New Modalities," *The BBI Newsletter*, located at <http://findarticles.com/p/articles/mi_m3570/is_n9_v21/ai_n27541529>, last visited on Mar. 12, 2009, 2 pages.

Fennis et al. "Mandibular reconstruction: A clinical and radiographic animal study on the use of autogenous scaffolds and platelet-rich plasma," *Int. J. Oral Maxillofac. Surg.*, 2002, 31:281-286.

Fennis et al. "Mandibular reconstruction: A histological and histomorphometric study on the use of autoge-us scaffolds, particulate cortico-cancellous bone grafts and platelet rich plasma in goats," *Int. J. Oral Maxillofac. Surg.*, 2004, 33:48-55.

Ficarra, G. et al. (2005). "Osteonecrosis of the Jaws in Periodontal Patients with a History of Bisphophonates Treatment," *J. Clin. Periodontol.* 32:1123-1128.

Finkelman, R.D. et al. (1995). "Systematic PDGF ± Alendronate Increases Bone Density in OVX Rats," Abstract No. 1281, *J. Dental Res.* 74:172.

Fontana et al. "Effect of Platelet-Rich Plasma on the Peri-implant Bone Response: An Experimental Study," *Implant Dentistry*, 2004, 13:73-78.

Franco, B. et al. (Jan.-Jun. 2008). "Tissue Engineering Approaches for the Construction of a Completely Autologous Tendon Substitute," *Indian J. Plast. Surg.* 41(1):38-46, 13 pages.

Freedonia (Sep. 2006). "Biocompatible Materials. US Industry Study with Forecasts to 2010 & 2015," Study #2111, located at < http://www.freedoniagroup.com/pdf/2111smwe.pdf>, last visited on Jun. 17, 2010, 8 pages (Table of Contents Only.).

Fribourg, D. et al. (Oct. 15, 2004). "Incidence of Subsequent Vertebral Fracture After Kyphoplasty," *Spine* 29(20):2270-2276.

Fukui, A. et al. (Sep. 1993). "Isolation and Characterization of *Xenopus* activin and Follistatin," *Devel. Biol.* 159(1):131-139.

Galatz, L.M. et al. (Feb. 2004). "The Outcome and Repair Integrity of Completely Arthoscopically Repaired Large and Massive Rotator Cuff Tears," *J. Bone Joint Surg. Am.* 86A(2):219-244.

Gamradt, S.C. et al. (Mar. 2007). "Platelet Rich Plasma in Rotator Cuff Repair," *Tech. In Orthop.* 22(1):26-33.

Garg, A.K. (1995). "Grafting Materials in Repair and Restoration," Chapter 5 in *Tissue Engineering: Applications in Maxillofacial Surgery and Periodontics*, Lynch, S.E. et al. eds., Quintessence Publishing, pp. 83-101.

Garg, "The Use of Platelet-Rich Plasma to Enhance the Success of Bone Grafts Around Dental Implants," *Dental Implantology Update*, Mar. 2000, 11(3):17-21.

Gazielly, D.F. et al. (Jul. 1994). "Functional and Anatomical Results After Rotator Cuff Repair," *Clin. Orthop. Relat. Res.* 304:43-53.

Gelberman, R.H. et al. (Mar. 2007). "The Early Effects of Sustained Platelet-Derived Growth Factor Administration on the Functional and Structural Properties of Repaired Intrasynovial Flexor Tendons: An In Vivo Biomechanic Study at 3 Weeks in Canines," *J. Hand Surg. Am.* 32A(3):373-379.

Gerber, C. et al. (May 1994). "Mechanical Strength of Repairs of the Rotator Cuff," *J. Bone Joint Surg. Br.* 76-B(3):371-380.

Gerber, C. et al. (Apr. 2000). "The Results of Repair of Massive Tears of the Rotator Cuff," *J. Bone Joint Surg. Am.* 82-A(4):505-515.

Giannobile, W.V. et al. (1994). "Synergistic Effects of Insulin-Like Growth Factors-I (IGF-I) with Other Growth Factors on Bone Formation in vitro," Abstract No. 831, J. Dental Res. 73:205.

Giannobile et al. "Comparison of Canine and Non-Human Primate Animal Models for Periodontal Regenerative Therapy: Results Following a Single Administration of PDGF/IGF-I," *J. Periodontol.*, Dec. 1994, 65(12):1158-1168.

Giannobile, W.V. et al. (Nov. 1995). "Platelet Derived Growth Factor (PDGF) and Insulin-Like Growth Factor (IGF-I) Enhances Periodontal Regeneration in *Macaca fascicularis*," Abstract No. 28, Advanced Dental Research 9(3 Suppl.):29.

Giannobile, W.V. et al. (Jul. 1996). "Comparative Effects of Platelet-Derived Growth Factor and Insulin-Like Growth Factor-I, Individually and in Combination, on Periodontal Regeneration in *Macaca fascicularis*," *J. Periodontal Res.* 31(5):301-312.

Giannobile et al. "Periodontal Tissue Engineering by Growth Factors," *Bone*, Jul. 1996, 19(1), Supplement: 23S-37S.

Giannobile et al. "Non-Coordinate Control of Bone Formation Displayed by Growth Factor Combinations with IGF-I," *J Dent Res*, Sep. 1997, 76(9):1569-1578.

Giannobile et al. "Recombinant Human Osteogenic Protein-1 (OP-1) Stimulates Periodontal Wound Healing in Class III Furcation Defects," *J Periodontol*, Feb. 1998, 69(2):129-137.

Giannobile, "Platelet-Derived Growth Factor (PDGF) Gene Delivery for Application in Periodontal Tissue Engineering," *J Periodontol*, Jun. 2001, 72(6):815-823.

Giannobile, W.V. (2008). "Advances in Gene Therapy for Periodontal Bioengineering," Chapter 3 in *Tissue Engineering: Applications in Maxillofacial Surgery and Periodontics*, Second Edition, Lynch, S.E. et al. eds., Quintessence Publishing Co.: Hanover Park, IL, pp. 37-46.

Giddings, V.L. et al. (2000). "Calcaneal Loading During Walking and Running," *Med. Sci. Sports Exerc.* 32(3):627-634.

Gilbertson et al. "Platelet-derived Growth Factor C (PDGF-C), a Novel Growth Factor That Binds to PDGF α and β Receptor," *The Journal of Biological Chemistry*, Jul. 20, 2001, 276(29):27406-27414.

Goutallier, D. et al. (Jul. 1994). "Fatty Muscle Degeneration in Cuff Ruptures: Pre- and Postoperative Evaluation by CT Scan," *Clin. Orthop.* 304:78-83.

Grageda, "Platelet-Rich Plasma and Bone Graft Materials: A Review and a Standardized Research Protocol," *Implant Dentistry*, 2004, 13(4):301-309.

Green et al. "Immunolocalization of platelet-derived growth factor A and B chains and PDGF-α and β-receptors in human gingival wounds," *Journal of Periodontal Research*, 1997, 32(2):209-214.

Gronwald et al. "Cloning and expression of a cDNA coding for the human platelet-derived growth factor receptor: Evidence for more than one receptor class," *Proc. Natl. Acad. Sci. USA*, May 1988, 85:3435-3439.

Hanel, D.P. et al. (Jan. 2002). "Wrist Fractures," *Orthop. Clin. North Am.* 33(1):35-57.

Harryman, D.T. et al. (Aug. 1991). "Repairs of the Rotator Cuff," *J. Bone Joint Surg. Am.* 73-A(7):982-989.

Hart et al. "Synthesis, Phosphorylation, and Degradation of Multiple Forms of the Platelet-derived Growth Factor Receptor Studied Using a Monoclonal Antibody," *The Journal of Biological Chemistry*, Aug. 5, 1987, 262(22):10780-10785.

Hart et al. "Two Classes of PDGF Receptor Recognize Different Isoforms of PDGF," *Science*, Jun. 1988, 240:1529-1531.

Hart, C.E. et al. "Purification of PDGF-AB and PDGF-BB from Human Platelet Extracts and Identification of All Three PDGF Dimers in Human Platelets," Biochemistry, Jan. 9, 1990, 29(1):166-172.

Hattrup, S.J. et al. (1985). "A Review of Ruptures of the Achilles Tendon," *Foot & Ankle* 6(1):34-38.

Hee et al. (2003). "Do Autologous Growth Factors Enhance Transformational Lumbar Interbody Fusion?" *Eur. Spine. J.* 12(4):400-407.

Heini, P.F. et al. (2001, e-pub. Jun. 14, 2001). "Bone Substitutes in Vertebroplasty," *Eur. Spine J.* 10:S205-S213.

Helm et al. (Apr. 2001). "Bone Graft Substitutes for the Promotion of Spinal Arthrodesis," *Neurosur. Foc.* 10(4):1-5.

Hess, G.W. (Feb. 2010). "Achilles Tendon Rupture: A Review of the Etiology, Population, Anatomy, Risk Factors, and Injury Prevention," *Foot Ankle Spec.* 3(1):29-32.

Higashi, T. et al. (Jun. 1996). "Influence of Particle Size of Calcium Phosphate Ceramics as a Capping Agent on the Formation of a Hard Tissue Barrier in Amputated Dental Pulp," *Journal of Endodontics* 22(6):281-283.

Hildebrand, K.A. et al. (1998). "The Effects of Platelet-Derived Growth Factor-BB on Healing of the Rabbit Medial Collateral Ligament. An in Vivo Study," *American Journal of Sports Medicine* 26(4):549-554.

(56) References Cited

OTHER PUBLICATIONS

Hoffmann, A. et al. (Dec. 2007, e-pub. Jul. 19, 2007). "Tendon and Ligament Engineering in the Adult Organism: Mesenchymal Stem Cells and Gene-Therapeutic Approaches," *Int. Orthop.* 31(6):791-797.

Hollinger, J.O. et al. (Jan. 2008, e-pub. Aug. 3, 2007). "Accelerated Fracture Healing in the Geriatric Osteoporotic Rat with Recombinant Human Platelet-Derived Growth Factor-BB and an Injectable Beta-Tricalcium Phosphate/Collagen Matrix," *J. Orthopedic Res.* 26:83-90.

Hollinger, J.O. et al. (Feb. 2008). "Recombinant Human Platelet Derived Growth Factor: Biology and Clinical Applications," *J. Bone & Joint Surgery* 90-A(Suppl. 1):48-54.

Hollinger, J.O. et al. (2008). "Therapeutic Opportunities for Bone Grafting," Chapter 68 *in Principles of Regenerative Medicine Atala*, A. et al. eds., Academic Press: Burlington, MA, pp.1164-1175.

Hollinger, J.O. et al. (2008). "Protein Therapeutics and Bone Healing," Chapter 1 *in Tissue Engineering: Applications in Maxillofacial Surgery and Periodontics*, Second Edition, Lynch, S.E. et al. eds., Quintessence Publishing Co.: Hanover Park, IL, pp. 3-25.

Hossain, M.Z. et al. (Jul. 1996). "Biological Responses of Autogenous Bone and Beta-Tricalcium Phosphate Ceramics Transplanted into Bone Defects to Orthodontic Forces," *Cleft Palate-Craniofacial Journal* 33(4):277-283.

Howell, T.H. et al. (1996). "Polypeptide Growth Factors for Periodontal Regeneration," *Current Opinion in Periodontology* 3:149-156.

Howell et al. "A Phase I/II Clinical Trial to Evaluate a Combination of Recombinant Human Platelet-Derived Growth Factor-BB and Recombinant Human Insulin-Like Growth Factor-I in Patients with Period. Dis.," *J. Periodontol.*, Dec. 1997, 68(12):1186-1193.

Howes et al. "Platelet-Derived Growth Factor Enhances Demineralized Bone Matrix-Induced Cartilage and Bone Formation," *Calcif Tissue Int.*, 1988, 42:34-38.

Huang, L-H. et al. "The Effect of Platelet-Rich Plasma on the Coronally Advanced Flap Root Coverage Procedure: A Pilot Human Trial," *J. Periodontal*, Oct. 2005, 76(10):1768-1777.

Hsu et al. (Jul. 2004). "Clinical Implications of Growth Factors in Flexor Tendon Wound Healing," *The Journal of Hand Surgery* 29A(4):551-563.

Ignotz, R.A. et al. (Mar. 25, 1986). "Transforming Growth Factor-β Simulates the Expression of Fibronectin and Collagen and Their Incorporation in the Extracellular Matrix," *J. Biol.Chem.* 261(9):4337-4345.

Ikezawa et al. "Characterization of Cementum Derived Growth Factor as an Insulin-Like Growth Factor-I Like Molecule," *Connective Tissue Research*, 1997, 36(4):309-319.

Inglis, A.E. et al. (Oct. 1976). "Ruptures of the Tendo Achilles: An Objective Assessment of Surgical and Non-Surgical Treatment," *J. Bone Joint Surg.* 58A(7):990-993.

Ito, Y. et al. (2004, e-pub. Mar. 26, 2004). "Bone Formation Using Novel Interconnected Porous Calcium Hydroxyapatite Ceramic Hybridized with Cultured Marrow Stromal Stem Cells Derived From Green Rat," *J. Biomed. Mater. Res.* 69A:454-461.

Jensen et al. "Platelet rich plasma and fresh frozen bone allograft as enhancement of implant fixation—An experimental study in dogs," *Journal of Orthopaedic Research*, 2004, 22:653-658.

Jensen, O.T. et al. (2008). "Alveolar Distraction Osteogenesis and Tissue Engineering," Chapter 14 *in Tissue Engineering: Applications in Maxillofacial Surgery and Periodontics*, Second Edition, Lynch, S.E. et al. eds., Quintessence Publishing Co.: Hanover Park, IL, pp. 203-219.

Jensen, O.T. (2008). "Dentoalveolar Modification with an Osteoperiosteal Flap and rhPDGF-BB," Chapter 15 *in Tissue Engineering: Applications in Maxillofacial Surgery and Periodontics*, Second Edition, Lynch, S.E. et al. eds., Quintessence Publishing Co.: Hanover Park, IL, pp. 220-225.

Jiang, D. et al. "Modification of an Osteoconductive Anorganic Bovine Bone Miami Matrix with Growth Factors," *J. Periodonlol.*, Aug. 1999, 70(8):834-839.

Jin et al. "Engineering of Tooth-Supporting Structures by Delivery of Pdgf Gene Therapy Vectors," *Molecular Therapy*, Apr. 2004, 9(4):519-526.

Jin, Q. et al. (Mar. 5, 2008). "Nanofibrous Scaffolds Incorporating PDGF-BB Microspheres Induce Chemokine Expression and Tissue Neogenesis In Vivo," *PLoS One* 3(3):e1729, pp. 1-9.

Jones et al. (1992). "Isolation of Vgr-2, a Novel Member of the Transforming Growth Factor-Beta-related Gene Family," *Mol Endocnnol.* 6(11):1961-1968.

Jozsa, L. et al. (Aug. 1989). "Fibronectin and Laminin in Achilles Tendon," *Acta Orthop Sacninavica* 60(4):469-471.

Kademani, D. et al. (Aug. 2006). "Primary Surgical Therapy for Osteonecrosis of the Jaw Secondary to Bisphosphonate Therapy," *Mayo Clin. Proc.* 81(8):1100-1103.

Kaigler, "Growth factor delivery for oral and periodontal tissue engineering," *Expert Opin Drug Deliv.*, 2006, 3(5):647-662.

Kapuściński, P. et al. (Jul.-Sep. 1996). "An Analgesic Effect of Synthetic Human Calcitonin in Patients with Primary Osteoporosis," *The Polish Journal of Medicine and Pharmacy* 28(98):83-86.

Kassolis et al. "Alveolar Ridge and Sinus Augmentation Utilizing Platelet-Rich Plasma in Combination with Freeze-Dried Bone Allograft: Case Series," *Journal of Periodontology*, Oct. 2000, 71(10):1654-1661.

Kazlauskas et al. "Different effects of homo- and heterodimers of platelet-derived growth factor A and B chains on human and mouse fibroblasts," *The EMBO Journal* (1988) 7 (12):3727-3735.

Kim et al. "Use of Particulate Dentin-Plaster of Paris Combination with/without Platelet-Rich Plasma in the Treatment of Bone Defects Around Implants," *The International Journal of Oral & Maxillofacial Implants*, 2002; 17:86-94.

Kim et al. "A Comparative Study of Osseointegration of Avana Implants in a Demineralized Freeze-Dried Bone Alone or With Platelet-Rich Plasma," *J Oral Maxillofac Surg*, 2002, 60:1018-1025.

Klotzbuecher, C.M. et al. (Apr. 2000). "Patients with Prior Fractures Have an Increased Risk of Future Fractures: A Summary of the Literature and Statistical Synthesis," *J. Bone Miner. Res.* 15(4):721-739.

Kobayashi, M. et al. (May/Jun. 2006). "Expression of Growth Factors in Early Phase of Supraspinatus Tendon Healing in Rabbits," *J. Shoulder Elbow Surg.* 15(3):371-377.

Kovacevic, D. et al. (Mar. 2008). "Biological Augmentation of Rotator Cuff Tendon Repair," *Clin. Orthop. Relat. Res.* 466(3):622-633.

Kovacs et al. "Comparative Study of β-Tricalclum Phosphate Mixed with Platelet-Rich Plasma versus β-Tricalcium Phosphate, A Bone Substitute Material in Dentistry," *Acts Veterinaria Hungarica*, 2003, 51(4):475-484.

Landesberg et al. "Quantification of Growth Factor Levels Using a Simplified Method of Platelet-Rich Plasma Gel Preparation," *J. Oral Maxillofac. Surg.*, 2000, 58:297-301.

Lasa et al. "Delivery of Demineralized Bone Powder by Fibrin Sealant," *Plast. Reconstr. Surg.*, 1995, 96(6):1409-1417.

Lasa Jr., C. et al. (1996). "Bone Induction by Demineralized Bone Powder and Partially Purified Osteogenin Using a Fibrin-Sealant Carrier," Chapter 14 *in Surgical Adhesives and.Sealants: Current Technology and Applications*, Sierra, D. et al. eds., Technomic Publishing.Company, Inc.: Lancaster, PA, pp. 135-144.

Lee, Y-M. et al. (Mar. 2000). "The Bone Regenerative Effect of Platelet-Derived Growth Factor-BB Delivered With a Chitosan/Tricalcium Phosphate Sponge Carrier," *J. Periodontal.* 71(3):418-424.

Lee, S.J. et al. (2001, e-pub. Feb. 13, 2001). "Molded Porous Poly ($_L$-Lactide) Membranes for Guided Bone Regeneration with Enhanced Effects by Controlled Growth Factor Release," *Journal of Biomedical Materials Research* 55:295-303.

Lee et al. "Enhanced bone formation by controlled growth factor delivery from chitosan-based biomaterials," *Journal of Controlled Release*, 2002, 78: 187-197.

Lekovic, V. et al. (Feb. 2002). "Comparison of Platelet-Rich Plasma, Bovine Porous Bone Mineral, and Guided Tissue Regeneration Versus Platelet-Rich Plasma and Bovine Porous Bone Mineral in the Treatment of Intrabony Defects: A Reentry Study," *J. Periodontol.* 73(2):198-205.

(56) References Cited

OTHER PUBLICATIONS

Letson, a.K. et al. (1994). "The Effect of Combinations of Growth Factors on Ligament Healing," *Clinical Orhopaedics and Related Research* 308:207-212.

Li, J. et al. (1994). "Systematic Administration of PDGF With or Without Alendronate Increases Spine and Whole Body Bone Mineral Density in OVX Rats," Abstract No. 59, *Sixteenth Annual Meeting of the American Society for Bone and Mineral Research*, Kansas City, MO. , Sep. 9-13, 1994, p. S135.

Liang et al. (Sep. 2000). "Effect of Cytokines on Repair of Tendon Injury," *Pub Med* 14(5):283-285, Abstract Only.

Liang, H.W. et al. (Aug. 2009). "Effect of Platelet -Derived Growth Factor-BB on Proliferation of Tendon Cells Cultured in vitro," *Zhonghua Shao Shang Za Zhi* 25(4):298-300, Abstract Only.

Lind et al. (1998). "Growth Factor Stimulation of Bone Healing," *Acta Orthopaedica Scandinavica Supplementum* Suppl. 283:2-37.

Lioubavina-Hack et al. "Methyl cellulose gel obstructed bone formation by GBR: an experimental study in rats," *J. Clin. Periodontol.*, 2005, 32:1247-1253.

Lioubavina-Hack et al. "Effect of Bio-Oss® with or without platelet-derived growth factor on bone formation by 'guided tissue regeneration': a pilot study in rats," *J Clin. Periodontol*, 2005, 32(12):1254-1260.

Lipshitz, H. et al. (Jun. 1975). "In Vitro Wear of Cartilage," *J. Bone Joint Surg. Am.* 57A(4):527-534.

Lynch, S.E. et al. (Nov. 1987). "Role of Platelet-Derived Growth Factor in Wound Healing: Synergistic Effects with Other Growth Factors," *Proc. Natl. Acad. Sci. USA* 84:7696-7700.

Lynch, S.E. et al. (1988). "Synergistic Effects of Recombinant Platelet-Derived Growth Factor Two and Insulin-Like Growth Factor-I in Wound Healing," Abstract No. 585, *J. Dental Res.* 67:186.

Lynch, S.E. et al. (1988). "Potential Role of Platelet-Derived and Insulin-Like Growth Factors in Periodontal Regeneration," Abstract No. 586, *J. Dental Res.* 67:186.

Lynch, S.E. et al. (Dec. 1988). "Growth Factors in Wound Healing: Single and Synergistic Effects," Abstract No. 238, *J. Cell Biol.* 107(6 Part 3):46a.

Lynch, S.E. et al. (1989). "Comparative Effects of Growth Factors on Soft Tissue Repair," Abstract No. 1153, *J. Dental Res.* 68:326.

Lynch, S.E. et al. (1989). "A Combination of Platelet-Derived and Insulin-Like Growth Factors Enhances Periodontal Regeneration," *J. Clin. Periodontol.* 16:545-548.

Lynch, S.E. (1990). "A Possible Role for Polypeptide Growth and Differentiation Factors in Periodontal Regeneration," Executive Committee on Chemotherpeutics; *Amer. Acad Peridontal—Position Paper* pp. 1-4.

Lynch, S.E. et al. (Jul. 1991). "The Effects of Short Term Application of a Combination of Platelet-Derived and Insulin-Like Growth Factors on Periodontal Wound Healing," *J. Periodontol.* 62(7) :458-467.

Lynch, S.E. et al. (Nov. 1991). "Effects of Platelet-Derived Growth Factor/Insulin Like Growth-Factor-I Combination on Bone Regeneration Around Titanium Dental Implants. Results of a Pilot Study in Beagle Dogs," *J. Periodontol.* 62(11):710-717.

Lynch, S.E. (1991). "Platelet-Derived Growth Factor and Insulin-Like Growth Factor. I: Mediators of Healing Soft Tissue and Bone Wounds," *Periodontol Case Reports NE Soc. Periodontists Bull.* 13(2):13-20.

Lynch, S.E. et al. (1992). "Effect of PDGF-B and IGF-I on Bone Regeneration," Abstract No. 82, *J. Dental Res.* 71:116.

Lynch, S.E. (1993). "Comparison of Results in the Canine and Primate Models Using a Single Regenerative Therapy," Abstract No. 37, *J. Dental Res.* 72:108.

Lynch, S.E. et al. (Jul.-Sep. 1994). "The Combination of Platelet-Derived Growth Factor-BB and Insulin-Like Growth Factor-I Stimulates Bone Repair in Adult Yucatan Miniature Pigs," *Wound Rep. Reg.* 2(3):182-190.

Lynch, S.E. et al. (Jan.-Mar. 1994). "Evidence for a Synergistic Interaction of Platelet-Derived Growth Factor-BB and Insulin-Like Growth Factor-I to Promote bone Repair in Adult Yucatan Micro Pigs," *Wound Repair and Regeneration* Abstract, 2(1):84.

Lynch, S.E. et al. (1994). "Polypeptide Growth Factors: Molecular Mediators of Tissue Repair," Chapter 33 *in Molecular Pathogenesis of Periodontal Disease*, Genco, R. et al eds., A.S.M. Press: Washington DC, pp. 415-425.

Lynch, S.E. (1994). "The Role of Growth Factors in Periodontal Repair and Regeneration," Chapter 11 *in Periodontal Regeneration: Current Status and Directions*, Polson, A. ed.Quintessence Publishing Co, Inc: Chicago, IL, 11:179-197.

Lynch, S.E. (1995). "Introduction," *in Tissue Engineering: Applications in Maxillofacial Surgery and Preiodontics*, Lynch, S.E. et al. eds., Quintessence Publishing, pp. xi-xvi.

Lynch, S.E. (2005). "Bone Regeneration Techniques in the Orofacial Region," Chapter 18 *in Bone Regeneration and Repair: Biology and Clinical Applications*, Lieberman, J.R. et al. eds., Humana Press Inc.: Totowa, NJ, pp. 359-390.

Lynch, S.E. et al. (Dec. 2006). "A New Era in Periodontal and Periimplant Regeneration: *Use of Growth-Factor Enhanced Matrices Incorporating rhPDGF*," *Compendium of Continuing Education in Dentistry* 27(12):672-679.

Lynch, S.E. et al. (2008). "Use of rhPDGF to Improve Bone and Periodontal Regeneration," Chapter 6 *in Tissue Engineering: Applications in Maxillofacial Surgery and Periodontics*, Second Edition, Lynch, S.E. et al. eds., Quintessence Publishing Co.: Hanover Park, IL, pp. 87-102.

Maffulli, N. et al. (2002). "Tendon Healing: Can It Be Optimized?" *British Journal of Sports Medicine* 36:315-316.

Maffulli, N. et al. (2003). "Types and Epidemiology of Tendinopathy," *Clinics in Sports Medicine* 22:675-692.

Maiorana et al. "Maxillary Sinus Augmentation with Anorganic Bovine Bone (Bio-Oss) and Autologous Platelet-Rich Plasma: Preliminary Clinical and Histologic Evaluations," *Int J Periodontics Restorative Den*, 2003, 23(3):227-235.

Manske et al. (Feb. 1985). "Flexor Tendon Healing," *Symposium on Flexor Tendon Surgery, Hand Clinics* 1(1):25-34.

Marcopoulou et al. (2003). "Proliferative Effect of Growth Factors TGF-β1, PDGF-BB, and rhBMP-2 on Human Gingival Fibroblasts and Periodontal Ligament Cells," *Journal of International Academy of Periodontology* 5(3):63-70.

Marx, R.E. et al. (2005). "Bisphosphonate-Induced Exposed Bone (Osteonecrosis/Osteoperosis) of the Jaws: Risk Factors, Recognition, Prevention, and Treatment," *J. Oral Maxillofac. Surg.* 63:1567-1575.

Marx, R.E. (2008). "Application of Tissue Engineering Principles to Clinical Practice," Chapter 4 *in Tissue Engineering: Applications in Maxillofacial Surgery and Periodontics*, Second Edition, Lynch, S.E. et al. eds., Quintessence Publishing Co.: Hanover Park, IL, pp. 47-63.

Marx, R.E. (2008). "Use of PRP in Oral and Maxillofacial Surgery and Periodontology," Chapter 9 *in Tissue Engineering: Applications in Maxillofacial Surgery and Periodontics*, Second Edition, Lynch, S.E. et al. eds., Quintessence Publishing Co.: Hanover Park, IL, pp. 132-144.

Mayfield, L. et al. (Oct. 1998). "Clinical and Radiographic Evaluation, Following Delivery of Fixed Reconstructions, at GBR Treated Titanium Fixtures," *Clin. Oral Implants Res.* 9:292-302.

McAllister, B. et al. (1998). "Long-term Evaluation of Sinus Grafting with Bio-Oss® in the Chimpanzee," Abstract No. 1097, *J. Dental Res.* 77:769.

McAllister et al. "Eighteen-month Radiographic and Histologic Evaluation of Sinus Grafting with Anorganic Bovine Bone in the Chimpanzee," *The International Journal of Oral & Maxillofacial Implants*, 1999, 14(3):361-368.

McCarrel, T. et al. (Aug. 2009, e-pub. Jan. 23, 2009). "Temporal Growth Factor Release from Platelet-Rich Plasma, Trehalose Lyophilized Platelets, and Bone Marrow Aspirate and their Effect on Tendon and Ligament Gene Expression," *J. Orthop. Res.* 27(8):1033-1042, Abstract Only.

McGuire, M.K. et al. (2006). "rhPDGF-BB Promotes Healing of Periodontal Defects: 24-Month Clinical and Radiographic Observations," *Int. J. Periodontics Restorative Dent.* 26(3):223-231.

McGuire, M.K. (2008). "Soft Tissue Engineering Applications in Dentistry," Chapter 7 *in Tissue Engineering: Applications in Maxillofacial Surgery and Periodontics*, Second Edition, Lynch, S.E. et al. eds., Quintessence Publishing Co.: Hanover Park, IL, pp. 103-118.

(56) References Cited

OTHER PUBLICATIONS

McMurty, R.Y. et al. (1992). "Fractures of the Distal Radius," Chapter 35 in *Skeletal Trauma*, Browner B.D. et al. eds., W.B. Saunders Company: Philadelphia, PA, 2:1063-1094.

Mehta, V. et al. (Apr.-Jun. 2005). "The Use of Growth Factors on Tendon Injuries," *Journal of Hand Therapy* 18:87-92.

Melo, M.D. et al. (Dec. 2005). "Osteonecrosis of the Jaws in Patients with a History of Receiving Bisphosphonate Therapy. Strategies for Prevention and Early Recognition," *J. American Dental Association* 136:16751681.

Migliorati, C.A. et al. (Jun. 2006). "Bisphosphate-Associated Osteonecrosis: A Long Term Complication of Bisphophonate Treatment," *Lancet Oncol.* 7:508-514.

Millette, E. et al. (2006). "Platelet-Derived Growth Factor-BB Transactivates the Fibroblast Growth Factor Receptor to Induce Proliferation in Human Smooth Muscle Cells," *Trends Cardiov. Med.* 16(1):25-28.

Mitlak et al. "The Effect of Systemically Administered PDGF-BB on the Rodent Skeleton," *Journal of Bone and Mineral Research*, 1996, 11(2):238-247.

Molloy, T. et al. (2003). "The Roles of Growth Factors in Tendon and Ligament Healing," *Sports Med.* 33(5):381-394.

Mont, M.A. et al. (Oct. 1998). "Osteonecrosis of the Femoral Head. Potential Treatment with Growth and Differentiation Factors," *Clin. Orthop. Relat. Res.* 355(Suppl.):S314-S335, Abstract Only, 2 pages.

Morris, G.J. et al. (Jan. 2007). "Bisphosphonate Therapy for Women with Breast Cancer and at High Risk for Osteoporosis," *Journal of the National Medical Association* 99(1):35-45.

Mott, D.A. et al. (2002). "Enhancement of Osteoblast Proliferation in vitro by Selective Enrichment of Demineralized Freeze-Dried Bone Allograft with Specific Growth Factors," *J. Oral Implantol.* 28(2):57-66.

Mumford, J.H. et al. (Mar. 2001). "The Effects of Platelet Derived Growth Factor-BB on Periodontal Cells in in Vitro Wound Model," *J. Periodontal.* 72(3):331-340.

Nakamura, N. et al. (1998). "Early Biological Effect of in Vivo Gene Transfer of Platelet-derived Grown Factor (PDGF)-B into Healing Patellar Ligament," *Gene Therapy* 5:1165-1170.

Nancollas, G.H. et al. (2006, e-pub. Jul. 20, 2005). "Novel Insights into Actions of Bisphosphonates on Bone: Differences in Interactions with Hydrozyapatite," *Bone* 38:617-627.

Nase, J.B. et al. (Aug. 2006). "Osteonecrosis of the Jaw and Oral Bisphosphonate Treatment," *J. American Dental Association* 137:1115-1119.

Nash, T.J. et al. (Mar. 1994). "Effect of Platelet-Derived Growth Factor on Tibial Osteotomies in Rabbits," *Bone* 15(2):203-208.

Nevins, M.L. et al. (2003). "Evaluation of Periodontal Regeneration Following Grafting Intrabony Defects with Bio-Oss® Collagen: A Human Histologic Report," *Int. J. Periodont. Rest. Dent.* 23(1):9-17.

Nevins et al. "Periodontal Regeneration in Humans Using Recombinant Human Platelet-derived Growth Factor-BB (rhPDGF-BB) and Allogenic Bone," *J. Periodontal*, Sep. 2003, 74(9):1282-1292.

Nevins, M.L. et al. (2005). "Three-Dimensional Micro-Computed Tomographic Evaluation of Periodontal Regeneration: A Human Report of Intrabony Defects Treated with Bio-Oss Collagen," *Int. J. Periodontics Restorative Dent.* 25(4):365-373.

Nevins et al. "Platelet-Derived Growth Factor Stimulates Bone Fill and Rate of Attachment Level Gain: Results of a Large Multicenter Randomized Controlled Trial," *J. Periodontal*, Dec. 2005, 76(12):2205-2215.

Nevins, M. et al. (Oct. 2007). "Clinical Results Using Recombinant Human Platelet-Derived Growth Factor and Mineralized Freeze-Dried Bone Allograft in Periodontal Defects," *Int. J. Periodontics Restorative Dent.* 27(5):421-427.

Nevins, M. et al. (2008). "Treatment of Advanced Periodontal Defects Using Bioactive Therapies," Chapter 5 in *Tissue Engineering: Applications in Maxillofacial Surgery and Periodontics*, Second Edition, Lynch, S.E. et al. eds., Quintessence Publishing Co.: Hanover Park, IL, pp. 67-86.

Nevins, M.L. et al. (2008). "Site Development for Implant Placement: Regenerative and Esthetic Techniques in Oral Plastic Surgery," Chapter 8 in *Tissue Engineering: Applications in Maxillofacial Surgery and Periodontics*, Second Edition, Lynch, S.E. et al. eds., Quintessence.Publishing Co.: Hanover Park, IL, pp. 119-131.

Nickols, J.C. et al. (2008). "The Role of Growth Factors in Tendon Healing," Chapter 20 in *Tissue Engineering: Applications in Maxillofacial Surgery and Periodontics*, Second Edition, Lynch, S.E. et al. eds., Quintessence Publishing Co.: Hanover Park, IL, pp. 276-289.

Nistor, L. (Mar. 1981). "Surgical and Non-Surgical Treatment of Achilles Tendon Rupture: A Prospective Randomized Study," *J. Bone Joint Surg Am.* 63A(3):394-399.

Nociti, F.H. Jr. et al. (2000). "Histometric Evaluation of Bone Regeneration Around Immediate Implants Partially in Contact with Bone: A Pilot Study in Dogs," *Implant Dentistry* 9(4):321-328.

Oberg, S. et al. (Apr. 1994). "Bone Healing After Implantation of Hydroxyapatite Granules and Blocks (Interpore 200) Combined with Autolyzed Antigen-Extracted Allogeneic Bone and Fibrin Glue. Experimental Studies on Adult Rabbits," *International Journal of Oral and Maxillofacial Surgery* 23(2):110-114, abstract only.

Orbay, J.L. et al. (Jan. 2004). "Volar Fixed-Angle Plate Fixation for Unstable Distal Radius Fractures in the Elderly Patient," *J. Hand Surg.* 29A(1):96-102.

Orthovita, Inc. (Dec. 14, 2000). "510(k) Summary. Vitoss™ Scaffold Syntehtic Cancellous Bone Void Filler," located at <http://www.accessdata.fda.gov/cdrh_docs/pdf/k994337.pdf>, last visited on Mar. 30, 2010, 6 pages.

Orthovita, Inc. (Nov. 19, 2002). "Morningstar® Document Research™. Form 10-Q, Quarterly Repot Which Provides a Continuing View of a Company's Financial Position," located at <http://orthovita.com/investors/secfilings.aspx>, last visited on Jun. 17, 2010, 48 pages.

Orthovita, Inc. (2009). "Architects of the New Biomaterials Age, 2008 Annual Report," located at <http://orthovita.com/investors/annual-reports/previousreports.aspx>, last visited on Jun. 17, 2010, 93 pages.

Owen et al. (1984). "Simian Sarcoma Virus-Transformed Cells Secrete a Mitogen Identical to Platelet-Derived Growth factor," *Science* 25:54-56.

Palti, A. et al. (2002). "A Concept for the Treatment of Various Dental Bone Defects," *Implant Dentistry* 11(1):73-78.

Parashis, A. et al. (Jul. 1998). "Comparison of 2 Regenerative Procedures-Guided Tissue Regeneration and Demineralized Freeze-Dried Bone Allograft-in the Treatment of Intrabony Defects: A Clinical and Radiographic Study," *J. Periodontol.* 69(7):751-758.

Park et al. (Jun. 1995). "Periodontal Regeneration in Class III Furcation Defects of Beagle Dogs Using Guided Tissue Regenerative Therapy with Platelet-Derived Growth Factor," *J. Periodontol.* 66:462-477.

Paul, W. et al. (1999). "Development of Porous Spherical Hydroxyapatite Granules: Application Towards Protein Delivery," *J. Mater. Sci. Mater. Med.* 10:383-388.

Persson, G.R. et al. (2000). "A Retrospective Radiographic Outcome Assessment Study of Intra-Bony Defects Treated by Osseous Surgery or by Bone Graft Procedures," *J. Clin. Periodontol.* 27:104-108.

Petersen, W. et al. (Nov. 2003, e-pub. Apr. 16, 2003). "Hypoxia and PDGF Have a Synergistic Effect that Increases the Expression of the Angiogenetic Peptide Vascular Endothelial Growth Factor in Achilles Tendon Fibroblasts,"*Arch. Orthop. Trauma Surg.* 123(9):485-488.

Pfeilschifter, J. et al. (Jul.-Dec. 1990). "Stimulation of Bone Matrix Apposition in Vitro by Local Growth Factors: a Comparison Between Insulin-Like Growth Factor I, Platelet Derived Growth Factor, and Transforming Growth Factor β," *Endocrinology* 127(1):69-75.

Philippart et al. "Human Recombinant Tissue Factor, Platelet-rich Plasma, and Tetracycline Induce a High-Quality Human Bone Graft A 5-year Survey," *The International Journal of Oral and Maxillofacial Implants*, 2003, 18(3):411-416.

Phillips, S. et al. (1988). "The Direct Medical Costs of Osteoporosis for American Woman Aged 45 and Older, 1986," *Bone* 9(4):271-279.

Pickett, F.A. (Jul. 2006). "Bisphosphonate-Associated Osteonecrosis of the Jaw: A Literature Review and Clinical Practice Guidelines," *Journal of Dental Hygiene* 80(3):1-12.

(56) References Cited

OTHER PUBLICATIONS

Pietrzak, W.S. et al. (Jul. 2000). "Calcium Sulfate Bone Void Filler: A Review and a Look Ahead," *J. Craniofac. Surg.* 11(4):327-333; discussion p. 334.

Polverini, P.J. (Aug. 2002). "Angiogenesis in Health and Disease: Insights into Basic Mechanisms and Therapeutic Opportunities," *Journal of Dental Education* 66(8):962-975.

Premdas, J. et al. (2001). "The Presence of Smooth Muscle Action in Fibroblasts in the Torn Human Rotator Cuff," *Journal of Orthopaedic Research* 19:221-228.

Qiu, Y. et al. (2009). "Combination of PDGF-BB and bFGF Reduces Differentiation but Maintains Proliferation of Human Tenocytes in Low Bovine Serum Culture in vitro," *European Cells and Materials* 18(Suppl. 2):86.

Qu, Z. et al. (Nov. 1994). "Immunolocalization of Basic Fibroblast Growth Factor and Platelet-Derived Growth Factor-A During Adjuvant Arthritis in the Lewis Rat," *Am. J. Pathol.* 145(5):1 127-1139.

R&D Systems, Inc. (Date Unknown). "Quantikine® Human PDGF-BB Immunoassay," Package Insert, Catalog No. DBBoo, SBB, and Pdboo, located at <http://www.rndsystems.com/pdf/dbb00.pdf>, last visited on Mar. 30, 2010, 16 pages.

Rao, C.D. et al. (Apr. 1986). "Structure and Sequence of the Human c-*sis*/Platelet-Derived Growth Factor 2 (*SIS/PDGF2*) Transcriptional Unit," *Proc. Natl. Acad. Sci. USA* 83:2392-2396.

Rao, M.V. et al. (Mar. 2009). "Effects of Platelet-Derived Growth Factor, Vitamin D and Parathroid Hormone on Osteoblasts Derived from Cancer Patients on Chronic Bisphosphonate Therapy," *Int. J. Mol. Med.* 23(3):407-413, Abstract Only, 2 pages.

Rasubala, L. et al. "Platelet-derived Growth Factor and Bone Morphogenetic Protein in the Healing of Mandibular Fractures in Rats," *British Journal of Oral and Maxillofacial Surgery*, 2003, 41:173-178.

Rettig, A.C. et al. (2005). "Potential Risk of Rerupture in Primary Achilles Tendon Repair in Athletes Younger Than 30 Years of Age," *Am. J. Sports Med.* 33(1):119-123.

Rickert, M. et al. (2001). "A Growth and Differentiation Factor-5 (GDF-5)-Coated Suture Stimulates Tendon Healing in an Achilles Tendon Model in Rats," *Growth Factors* 19:115-126.

Riley, G. (2004, e-pub. Jul. 16, 2003). "The Pathogenesis of Tendinopathy. A Molecular Perspective," *Rheumatology* 43(2):131-142.

Robbins, K.C. et al. (Oct. 13, 1983). "Structural and Immunological Similarities Between Simian Sarcoma Virus Gene Product(s) and Human Platelet-Derived Growth Factor," *Nature* 305:605-608.

Rodeo, S.A. et al. (Dec. 1993). "Tendon Healing in a Bone Tunnel," *J. Bone Joint Surg. Am.* 75-A(12):1795-1803.

Rodeo, S.A. et al. (1999). "Use of Recombinant Human Bone Morphogenic Protein-2 to Enhance Tendon Healing in a Bone Tunnel," *Am. J. Sports Med.* 27(4):476-488.

Rodriguez et al. "Maxillary Sinus Augmentation with Deproteinated Bovine Bone and Platelet Rich Plasma with Simultaneous Insertion of Endosseous Implants," *J. Oral Maxiilofac. Surg.*, 2003, 61 :157-163.

Rohrich et al. (Nov. 1999). "Mersilene Suture as a Vehicle for Delivery of Growth Factors in Tendon Repair," *Journal of the American Society of Plastic Surgeons* 104(6):1713-1717.

Rolf, C.G. et al. (2001). "Increased Cell Proliferation and Associated Expression of PDGFRβ Causing Hypercellularity in Patellar Tendinosis," *Rheumatology* 40:256-261.

Ruggiero, S.L. et al. (2006, e-pub. Jul. 31, 2006). "Bisphosphonate-Related Osteoncerosis of the Jaw: Background and Guidelines for Diagnosis, Staging and Management," *Oral Surgery, Oral Medicine, Oral Pathology, Oral Radiology, and Endodontology* <http://www.sciencedirect.com/science/journal/10792104>, 8 pages.

Ruiz, G. et al. (1991). "Short Term Administration of Growth Factors Enhances Periodontal Regeneration," Abstract No. 1615, *J. Dental Res.* 70:468.

Rutherford et al. (1992). "Platelet-Derived and Insulin-Like Growth Factors Stimulate Regeneration of Periodontal Attachment in Monkeys," *Journal of Periodontal Research* 27(4-Part 1):285-290.

Sakiyama-Elbert, S.E. et al. (Nov. 2008). "Controlled-Release Kinetics and Biologic Activity of Platelet-Derived Growth Factor-BB for Use in Flexor Tendon Repair," *J. Hand Surg. Am.* 33(9):1548-1557, Abstract Only.

Sandberg, "Matrix in Cartilage and Bone Development: Current Views on the Function and Regulation of Major Organic Components," *Annals of Medicine*, 1991, 23:207-217.

Sarment, D.P. et al. (Feb. 1, 2006). "Effect of rhPDGF-BB on Bone Turnover During Periodontal Repair," *Journal of Clinical Periodontolgy* 33(2):135-140.

Sartori, S. et al. (2003, e-pub. May 20, 2003). "Ten-year Follow-up in a Maxillary Sinus Augmentation Using Anorganic Bovine Bone (Bio-Oss): A Case Report with Histomorphometric Evaluation," *Clin. Oral Implants Res.* 14(3):369-372.

Sasai, Y. et al. (Dec. 2, 1994). "*Xenopus chordin*: A Novel Dorsalizing Factor Activated by Organizer-Specific Homeobox Genes," *Cell* 79:779-790.

Saygin et al. "Molecular and Cell Biology of Cementum," *Periodontology*, 2000, 24:73-98.

Schenk, R.K. et al. (Jan./Feb. 1994). "Healing Pattern of Bone Regeneration in Membrane-Protected Defects: A Histologic Study in the Canine Mandible," *Int. J. Oral Maxillofac. Implants* 9(1):13-29.

Schmidt, C.C. et al. (Mar. 1995). "Effect of Growth Factors on the Proliferation of Fibroblasts from the Medial Collateral and Anterior Cruciate Ligaments," *J. Orthop. Res.* 13(2):184-190, Abstract Only.

Schmidt et al. "A review of the effects of insulin-like growth factor and platelet derived growth factor on in vivo cartilage healing and repair," *Osteoarthritis and Cartilage*, 2006, 14(5):403412.

Schmidt, M.B. et al. (2008). "Tissue Engineering Strategies in the Treatment of TMDs," Chapter 18 *in Tissue Engineering: Applications in Maxillofacial Surgery and Periodontics*, Second Edition, Lynch, S.E. et al. eds., Quintessence Publishing Co.: Hanover Park, IL, pp. 252-264.

Schmitt, J.M. et al. (Nov. 1997). "Comparison of Porous Bone Mineral and Biologically Active Glass in Critical-Sized Defects," *J. Periodontol.* 68(11):1043-1053.

Schnabel, L.V. et al. (Feb. 2007). "Platelet Rich Plasma (PRP) Enhances Anabolic Gene Expression Patterns in Flexor Digitorum Superficialis Tendons," *J. Orthop. Res.* 25(2):230-240, Abstract Only.

Secinfo.com (Mar. 31, 2003). "Interpore International Inc/DE 10-K for Dec. 31, 2002," located at <http://www.secinfo.com/dV179.2kp.htm, last visited on May 20, 2010, 57 pages.

Seeherman, H.J. et al. (Oct. 2008). "rhBMP-12 Accelerates Healing of Rotator Cuff Repairs in Sheep Model," *J. Bone Joint Surg. Am.* 90A(10):2206-2219.

Shahgaldi, B.F. et al. (Jan. 1991). "Repair of Cartilage Lesions Using Biological Implants. A Comparative Histological and Biomechanical Study in Goats," *J. Bone Joint Surg. Br.* 73-B(1):57-64.

Sharma, P. et al. (2008). "Tendinopathy and Tendon Injury: The Future," *Disability and Rehabilitation* 30(20-22):1733-1745.

Simion, M. et al. (Apr. 1994). "A Comparative Study of the Effectiveness of e-PTFE Membranes With and Without Early Exposure During the Healing Period," *Int. J. Periodontics Restorative Dent.* 14(2):166-180.

Simion, M. et al. (1994). "Vertical Ridge Augmentation Using a Membrane Technique Associated with Osseointegrated Implants," *Int. J. Periodontics Restorative Dent.* 14(6):497-511.

Simion, M. et al. (1995). "Bacterial Penetration in vitro Through GTAM Membrane With and Without Topical Chlorhexidine Application: A Light and Scanning Electron Microscopic Study," *J. Clin. Periodontol.* 22:321-331.

Simion, M. et al. (Feb. 1998). "Vertical Ridge Augmentation Around Dental Implants Using a Membrane Technique and Autogenous Bone or Allografts in Humans," *Int. J. Periodontics Restorative Dent.* 18(1):9-23.

Simion, M. et al. (1999). "Effect of Different Microstructures of e-PTFE Membranes on Bone Regeneration and Soft Tissue Response: A Histologic Study in Canine Mandible," *Clin. Oral Implants Res.* 10:73-84.

(56) References Cited

OTHER PUBLICATIONS

Simion, M. et al. (Oct. 2006). "Vertical Ridge Augmentation by Means of Deproteinized Bovine Bone Block and Recombination Human Platelet-Derived Growth Factor-BB: A Histologic Study in a Dog Model," *The International Journal of Periodontics & Restorative Dentistry* 26(5):415-423.

Simion, M. et al. (2008). "Minimally Invasive Strategies for Vertical Ridge Augmentation," Chapter 10 in *Tissue Engineering: Applications in Maxillofacial Surgery and Periodontics*, Second Edition, Lynch, S.E. et al. eds., Quintessence Publishing Co.: Hanover Park, IL, pp. 145-158.

Siris, E.S. et al. (Aug. 2006). "Adherence to Bisphosphonate Therapy and Fracture Rates in Osteoporotic Women: Relationship to Vertebral and Nonvertebral Fractures From 2 US Claims Databases," *Mayo Clin. Proc.* 81(8):1013-1022.

Sode, J. et al. (May 2007, e-pub. Mar. 3, 2007). "Use of Fluroquinolone and Risk of Achilles Tendon Rupture: A Population-based Cohort Study," *Eur. J. Clin. Pharmacol.* 63(5):499-503.

Solheim, E. "Growth Factors in Bone," *International Orthopedics (SICOT)*, 1998, 22:410-416.

Spector, M. (2008). "Basic Principles of Scaffolds in Tissue Engineering," Chapter 2 in *Tissue Engineering: Applications in Maxillofacial Surgery and Periodontics*, Second Edition, Lynch, S.E. et al. eds., Quintessence Publishing Co.: Hanover Park, IL, pp. 26-36.

Spindler, K.P. et al. (1995). "Proliferative Response to Platelet-Derived Growth Factor in Young and Old Rat Patellar Tendon," *Connective Tissue Research* 31(2):171-177.

Spindler, K.P. et al. (Jul. 1996). "Patellar Tendon and Anterior Cruciate Ligament Have Different Mitogenic Responses to Platelet-Derived Growth Factor and Transforming Growth Factor β," Journal of Orthopaedic Research 14(4):542-546.

Stephan, E.B. et al. (Apr. 1999). "Anogranic Bovine Bone Supports Osteoblastic Cell Attachment and Proliferation," *J. Periodontol.* 70(4):364-369.

Stephan et al. "Platelet-Derived Growth Factor Enhancement of a Mineral-Collagen Bone Substitute," *J. Periodontal*, Dec. 2000, 71:1887-1892.

Strom, T.B. (Sep. 6, 2005). "Saving Islets from Allograft Rejection," *PNAS USA* 102(36):12651-12652.

Suba et al. "Facilitation of β-Tricalcium Phosphate-Induced Alveolar Bone Regeneration by Platelet-Rich Plasma in Beage Dogs: A Histologic and Histomorphometric Study," *The International J. of Oral and Maxillofacial Implants*, 2004, 19(6):832-838.

Tadic, D. et al. (2004). "A Novel Method to Produce Hydroxyapatite Objects with Interconnecting Porosity that Avoids Sintering," *Biomaterials* 25(16):3335-3340.

Tamai, N. et al. (2002). "Novel Hydroxyapatite Ceramics with an Interconnective Porous Structure Exhibit Superior Osteoconduction in vivo," *J. Biomed. Mater. Res.* 59:110-117.

Teraoka, K. et al. (2004). "Construction of an Interconnected Pore Network Using Hydroxyapatite Beads," *Key. Eng. Mater.* 254-256:257-259.

Teraoka, K. et al. (Sep. 2004). "Construction of Interconnected Pore Network Using Hydroxyapatite Small Components," *Trans. Mater. Res. Soc. Jpn.* 29(6):2919-2921.

Thompoulos, S. et al. (May 2005). "Effect of Several Growth Factors on Canine Flexor Tendon Fibroblast Proliferation and Collagen Synthesis in vitro," *J. Hand Surg. Am.* 30(3):441447, Abstract Only.

Thomopoulos, S. et al. (Oct. 2007, e-pub. Jun. 5, 2007). "PDGF-BB Released in Tendon Repair Using a Novel Delivery System Promotes Cell Proliferation and Collagen Remodeling," *J. Orthop. Res.* 25(17):1358-1368.

Thomopoulos, S. et al. (Sep. 2009, e-pub. Mar. 25, 2009). "Enhanced Flexor Tendon Healing through Controlled Delivery of PDGF-BB," *J. Orthop. Re.* 27(9):1209-1215.

Thomopoulos, S. et al. (Feb. 2010, e-pub. Nov. 24, 2009). "bFGF and PDGF-BB for Tendon Repair: Controlled Release and Biologic Activity by Tendon Fibroblasts in Vitro," *Ann. Biomed. Eng.* 38(2):225-234.

Tinti, C. et al. (1996). "Vertical Ridge Augmentation: What is the Limit?" *Int. J. Periodontics Restorative Dent.* 16(3):221-229.

Uggen, J.C. et al. (Jan. 2005). "Tendon Gene Therapy Modulates the Local Repair Enviornment in the Shoulder," *J. Am. Osteopath. Assoc.* 105(1):20-21.

Uggen, C. et al. (2010). "The Effect of Recombinant Human Platelet-Derived Growth Factor BB-Coated Sutures on Rotator Cuff Healing in a Sheep Model," *Arthroscopy* 26(11):1456-1462.

U.S. Appl. No. 10/965,319, filed Oct. 14, 2004, by Lynch.

Van Den Wyngaert, T. et al. (Aug. 2006). "Bisphosphonates and Osteonecrosis of the Jaw: Cause and Effect or a post hoc Fallacy?" *Annals of Oncology* 17(8):1197-1204.

Venkatasatya, M. et al. (2008). The Effect of PDGF, Vitamin D and Pth on Osteoblasts Derived From Patients on Chronic Bisphosphonate Therapy , Dissertation for the State University of New York at Buffalo, located at <http://gradworks.umi.com/14/531/1453440.html>, last visited on Mar. 31, 2010, 2 pages, Abstract Only.

Virchenko, O. et al. (2008, e-pub. Jul. 4, 2008). "Early Achilles Tendon Healing in Sheep," *Arch. Orthop. Trauma Surg.* 128:1001-1006.

Visnapuu et al. "Distribution of fibroblast growth factors (FGFR-1 and -3) and platelet-derived growth factor receptors (PDGFR) in the rat mandibular condyle during growth," *Orthod. Craniofadal.* 2002, 5:147-153.

Walter, C. et al. (2006, e-pub. Aug. 29, 2006). "Prevalence of Bisphophonate Associated Osteonecrosis of the Jaw within the Filed of Osteonecrosis," *Support Care Center* 6 pages.

Wang, Y. et al. (Feb. 23, 1996). "A Large Family of Putative Transmembrane Receptors Homologous to the Product of the *Drosophila* Tissue Polarity Gene Frizzled," *J. Biol. Chem.* 271(8):4468-4476.

Wang, L. et al. (2004). "Three-Dimensional Porous Network Structure Developed in Hydroxyapatite-Based Nanocomposites Containing Enzyme Pretreated Silk Fibronin," *J. Nanopart.* 6(1):91-98.

Wang, X.T. et al. (Sep. 2004). "Tendon Healing In Vitro: Genetic Modification of Tenocytes With Exogenous Pdgf Gene and Promotion of Collagen Gene Expression," *The Journal of Hand Surgery* 29A(5):884-890.

Warner, J.J.P. et al. (Jan. 1992). "Anatomy and Relationships of the Suprascapular Nerve: Anatomical Constraints to Mobalization of the Supraspinauts and Infraspinatus Muscles in the Management of Massive Rotator-Cuff Tears," *J. Bone Joint Surg. Am.* 74-A(1):36-45.

Wei et al. "Nano-Fibrous Scaffold for Controlled Delivery of Recombinant Human PDGF-BB," *Journal of Controlled Release*, 2006, e-pub. Mar. 3, 2006, 112:103-110.

Weiler, A. et al. (2004). "The Influence of Locally Applied Platelet-Derived Growth Factor-BB on Free Tendon Graft Remodeling After Anterior Cruciate Ligament Reconstruction," *Am. J. Sports Med.* 32(4):881-891.

White, E. et al. (1986). "Biomaterial Aspects of lnterpore-200 Porous Hydroxyapatite," *Dent. Clin. North Am.* 30(1):49-67, Abstract only.

Wiesen, R.J. et al. (1998). "Efficacy of Bovine Bone Mineral in Vertical Osseous Defects," Abstract No. 1165, *J. Dental Res.* 77:777.

Wikesjö et al. (1988). "Repair of Periodontal Furcation Defects in Beagle Dogs Following Reconstructive Surgery Including Root Surface Demineralization with Tetracycline Hydrochloride and Topical Fibronectin Application," *J. Clin. Periodontol* 15:73-79.

Wikesjö et al. (1989). "Effects of Subgingival Irrigation on A. actinomycetemcomitans," *J. Clin. Perrodont.* 16:116-119.

Williams et al. "Tissue Engineering: What Does It Mean? Why Is It Important?" *Compendium*, Jan. 2005, 26(1):54-60.

Wisner-Lynch, L.A. (Oct. 2006). "From Passive to Active: Will Recombinant Growth Factor Therapeutics Revolutionize Regeneration?" *Int. J. Periodont. and Rest. Dent.* 26(5):409-411.

Wong, M.W. et al. (Oct. 2003). "Effect of Dexamethasone on Cultured Human Tenocytes and its Reversibility by Platelet-Derived Growth Factor," *Journal of Bone and Joint Surgery American* 85-A(10)1914-1920, Abstract Only.

Woo, S.L-Y. et al. (1998). "Engineering the Healing of the Rabbit Medical Collateral Ligament," *Medical and Biological Engineering and Computing* 36:359-364.

(56) References Cited

OTHER PUBLICATIONS

Woo, S-B. et al. (May 16, 2006). "Systematic Review: Bisphosphonates and Osteonecrosis of the Jaws," *Annals of Internal Medicine* 144(10):753-761.
Yang, C. et al. (2003). "Vascular Endothelial Growth Factor Gene Transfection to Enhance the Repair of Avascular Necrosis of the Femoral Head of Rabbit," *Chinese Medical Journal* 116(10):1544-1548.
Yazawa et al. "Basic Studies on the Clinical Applications of Platelet-Rich Plasma," *Cell Transplantation*, 2003, 12:509-518.
Yazawa, M. et al. (May 2004). "Basic Studies on the Bone Formation Ability by Platelet Rich Plasma in Rabbits," *Journal of Craniofacial Surgery* 15(3):439-446.
Yokota, K. et al. (2008, e-pub. Feb. 1, 2008). "Platelet-Rich Plasma Accelerated Surgical Angio-Genesis in Vascular Necrotic Bone. An Experimental Study in Rabbits," *Acta Orhopaedica* 79(1):106-1 10.
Younger, E.M. et al. (1989). "Morbidity at Bone Graft Donor Sites," *J. Orthop. Trauma* 3(3):192-195.
Zavras, A.I. et al. (2006). "Bisphosphonates Are Associated With Increased Risk for Jaw Surgery in Medical Claims Data: Is it Osteonecrosis?" *J. Oral Maxillofac. Surg.* 64:917-923.
Zhu et al. "Gene Transfer and Expression of Platelet-Derived Growth Factors Modulate Periodontal Cellular Activity," *J. Dent Res*, 2001, 80(3):892-897.
Zimmer, Inc. (2005). "Zimmer® Collagen Repair Patch," Product No. 04-4100-001-00, 6 pages.
Advisory Action Before the Filing of an Appeal Brief mailed on Apr. 4, 2008, for U.S. Appl. No. 11/159,533, filed Jun. 23, 2005, 3 pages.
Advisory Action Before the Filing of an Appeal Brief mailed on Jun. 4, 2008, for U.S. Appl. No. 11/159,533, filed Jun. 23, 2005, 3 pages.
Amendment After Request for Continued Examination submitted on Aug. 7, 2008, for U.S. Appl. No. 11/159,533, filed Jun. 23, 2005, 18 pages.
Amendment and Response to Final Office Action submitted on Feb. 25, 2008, for U.S. Appl. No. 11/159,533, filed Jun. 23, 2005, 9 pages.
Amendment and Response to Non-Final Office Action submitted on Oct. 26, 2007, for U.S. Appl. No. 11/159,533, filed Jun. 23, 2005, 15 pages.
Amendment in Response to Non-Final Office Action submitted on Dec. 18, 2009, for U.S. Appl. No. 11/704,685, filed Feb. 9, 2007, 32 pages.
Amendment in Response to Non-Final Office Action submitted on Oct. 6, 2010, for U.S. Appl. No. 12/323,183, filed Nov. 25, 2008, 11 pages.
Amendment in Response to Non-Final Office Action submitted on Jan. 14, 2011, for U.S. Appl. No. 11/601,376, filed Nov. 17, 2006, 14 pages.
Amendment in Response to Non-Final Office Action submitted on Jan. 14, 2011, for U.S. Appl. No. 12/368,242, filed Feb. 9, 2009, 19 pages.
Amendment in Response to Non-Final Office Action submitted on Mar. 21, 2011, for U.S. Appl. No. 11/778,498, filed Jul. 16, 2007, 21 pages.
Extended European Search Report mailed on Jul. 26, 2010, for EP Patent Application No. 10166327.6, filed on Oct. 10, 2005, 6 pages.
Extended European Search Report mailed on Feb. 28, 2011, for EP Patent Application No. 11152879.0, filed on Oct. 10, 2006, 6 pages.
Extended European Search Report mailed on Mar. 2, 2011, for EP Patent Application No. 11152889.9, filed on Oct. 10, 2006, 6 pages.
Extended European Search Report mailed on Mar. 22, 2011, for EP Patent Application No. 11152743.7, filed on Feb. 9, 2007, 11 pages.
Final Office Action mailed on Feb. 7, 2008, for U.S. Appl. No. 11/159,533, filed Jun. 23, 2005, 8 pages.
Final Office Action mailed on Jan. 7, 2011, for U.S. Appl. No. 12/323,183, filed Nov. 25, 2008, 9 pages.
Final Office Action mailed on Jun. 9, 2011, for U.S. Appl. No. 12/513,491, filed Nov. 5, 2007 (Int'l filed), 10 pages.
Final Office Action mailed on Jun. 13, 2011, for U.S. Appl. No. 11/778,498, filed Jul. 16, 2007, 13 pages.

International Search Report mailed on Aug. 3, 2007, for PCT Application No. PCT/US2007/003582, filed on Feb. 9, 2007, 2 pages.
International Search Report mailed on Oct. 2, 2007, for PCT Application No. PCT/US05/36447, filed on Oct. 12, 2005, 1 page.
International Search Report mailed on Dec. 7, 2007, for PCT Application No. PCT/US2006/044766, filed on Nov. 17, 2006, 4 pages.
International Search Report mailed on May 20, 2009, for PCT Application No. PCT/US2007/083638, filed on Nov. 5, 2007, 5 pages.
International Search Report mailed on Jul. 8, 2009, for PCT Application No. PCT/US2008/054354, filed on Feb. 20, 2008, 8 pages.
International Search Report mailed on Aug. 4, 2008 for PCT Patent Application No. PCT/US2008/065666, filed on Jun. 3, 2008, 3 pages.
International Search Report mailed on Jun. 26, 2009, for PCT Application No. PCT/US2009/033596, filed on Feb. 9, 2009, 6 pages.
International Search Report mailed on Apr. 27, 2010, for PCT Patent Application No. PCT/US2010/026450, filed on Mar. 5, 2010, 1 page.
Non-Final Office Action mailed on Jul. 27, 2007, for U.S. Appl. No. 11/159,533, filed Jun. 23, 2005, 13 pages.
Non-Final Office Action mailed on Oct. 31, 2008, for U.S. Appl. No. 11/159,533, filed Jun. 23, 2005, 11 pages.
Non-Final Office Action mailed on Oct. 16, 2009, for U.S. Appl. No. 11/704,685, filed Feb. 9, 2007, 19 pages.
Non-Final Office Action mailed on Jul. 7, 2010, for U.S. Appl. No. 12/323,183, filed Nov. 25, 2008, 11 pages.
Non-Final Office Action mailed on Jul. 16, 2010, for U.S. Appl. No. 12/368,242, filed Feb. 9, 2009, 12 pages.
Non-Final Office Action mailed on Sep. 14, 2010, for U.S. Appl. No. 11/601,376, filed Nov. 17, 2006, 18 pages.
Non-Final Office Action mailed on Sep. 23, 2010, for U.S. Appl. No. 12/513,491, filed Nov. 5, 2007 (Int'l filed), 10 pages.
Non-Final Office Action mailed on Oct. 21, 2010, for U.S. Appl. No. 11/778,498, filed Jul. 16, 2007, 18 pages.
Non-Final Office Action mailed on Apr. 22, 2011, for U.S. Appl. No. 11/601,376, filed Nov. 17, 2006, 15 pages.
Non-Final Office Action mailed on Apr. 22, 2011, for U.S. Appl. No. 12/527,692, filed Feb. 20, 2008 (Int'l filed), 7 pages.
Notice of Allowance mailed on Apr. 23, 2010, for U.S. Appl. No. 11/704,685, filed Feb. 9, 2007, 10 pages.
Notice of Allowance mailed on Mar. 4, 2011, for U.S. Appl. No. 12/368,242, filed Feb. 9, 2009, 5 pages.
Response to Advisory Action submitted on Apr. 28, 2008, for U.S. Appl. No. 11/159,533, filed Jun. 23, 2005, 15 pages.
Response to Notice of Non-Compliant Amendment submitted on Nov. 2, 2007, for U.S. Appl. No. 11/159,533, filed Jun. 23, 2005, 7 pages.
Supplemental Response to Advisory Action of Jun. 4, 2008, submitted on Jun. 9, 2008, for U.S. Appl. No. 11/159,533, filed Jun. 23, 2005, 15 pages.
Supplementary European Search Report mailed on Aug. 29, 2008, for EP Application No. 05803356.4, filed on Oct. 12, 2005, 7 pages.
Written Opinion of the International Searching Authority mailed on Aug. 3, 2007, for PCT Application No. PCT/US07/003582, filed on Feb. 8, 2007, 7 pages.
Written Opinion of the International Searching Authority mailed on Oct. 2, 2007, for PCT Application No. PCT/US05/36447, filed on Oct. 12, 2005, 4 pages.
Written Opinion of the International Searching Authority mailed on Dec. 7, 2007, for PCT Application No. PCT/US2006/044766 filed on Nov. 17, 2006, 6 pages.
Written Opinion of the International Searching Authority mailed on May 20, 2009, for PCT Application No. PCT/US2007/083638, filed on Nov. 5, 2007, 6 pages.
Written Opinion of the International Searching Authority mailed on Jul. 8, 2009, for PCT Application No. PCT/US2008/054354, filed on Feb. 20, 2008, 10 pages.
Written Opinion of the International Searching Authority mailed on Aug. 4, 2008, for PCT Patent Application No. PCT/US2008/065666, filed on Jun. 3, 2008, 7 pages.
Written Opinion of the International Searching Authority mailed on Jun. 26, 2009, for PCT Patent Application No. PCT/US2009/033596, filed on Feb. 9, 2009, 6 pages.

(56) References Cited

OTHER PUBLICATIONS

Written Opinion of the International Searching Authority mailed on Apr. 27, 2010, for PCT Patent Application No. PCT/US2010/026450, filed on Mar. 5, 2010, 6 pages.

Amendment in Response to Non-Final Office Action submitted on Jul. 22, 2011, for U.S. Appl. No. 11/601,376, filed Nov. 17, 2006, 12 pages.

Al-Zube, L. et al. (2008). "Stimulation of Fracture Healing by Recombinant Human Platelet-Derived Growth Factor BB(rhPDGF-BB) Combined with Beta-Tricalcium Phosphate/Collagen Matrix in a Diabetic Rat Fracture Model," Poster No. 988, presented at 54th Annual Meeting of the Orthopaedic Research Society, San Francisco, CA, Mar. 2-5, 2008, one page.

Dines, J. et al. (2008). "rhPDGF-BB Enhances Rotator Cuff Tendon Healing in a Sheep Model," Paper No. 316, presented at 54th Annual Meeting of the Orthopaedic Research Society, San Francisco, CA, Mar. 2-5, 2008, one page.

Ehrlich, M.G. et al. (2008). "rhPDGF-BB Augmentation of New Bone Formation in a Rat Model of Distraction Osteogenesis," Poster No. 876, presented at 54th Annual Meeting of the Orthopaedic Research Society, San Francisco, CA, Mar. 2-5, 2008, one page.

Hollinger, J.O. (2007). "Enhanced Fracture Healing in the Geriatric-Osteoporotic Rat with Recombinant Human Platelet-Derived Growth Factor Homodimer BB (rhPDGF-BB) and Collagen/8-Tricalcium Phosphate Matrix," Poster No. 0930, 53rd Annual Meeting of the Orhopaedic Research Society, San Diego, CA, located at <http://www.ors.org/web/Transactions/53/0930.PDF>, last visited on Mar. 22, 2011, 1 page.

Kovacevic, D. et al. (2008). "PDGF Induces Cell Proliferation and Angiogenesis in a Rat Rotator Cuff Repair Model of Tendon-Bone Healing," Poster No. 1498, presented at 54th Annual Meeting of the Orthopaedic Research Society, San Francisco, CA, Mar. 2-5, 2008, one page.

Liu, Y. et al. (2008). "Evaluation of Recombinant Human Platelet-Derived Growth Factor-BB Combined with a Collagen Matrix as a Devices for Tendon Repair," Poster No. 1479, presented at 54th Annual Meeting of the Orthopaedic Research Society, San Francisco, CA, Mar. 2-5, 2008, one page.

Liu, Y. et al. (2009). "Evaluation of Four Collagen Matrices in Combination with Recombinant Human Platelet-Derived Growth Factor-BB (rhPDGF-BB) for Application in Rotator Cuff Repair," Poster No. 1266, presented at se Annual Meeting of the Orthopaedic Research Society, Las Vegas, NV, Feb. 22-25, 2009, one page.

Perrien, D.S. et al. (2008). "Percutaneous Injection of Gemos®2, a Cobmination of rhPDGF-BB and Bovine Type I Collagen/8 Tricalcium Phosphate ((3TCP) Matrix Increases Vertebral Bone Mineral Density in Geriatric Female Baboons," Poster No. 963, 54th Annual Meeting of the Orthopaedic Research Society, San Francisco, CA, located at <http://www.ors.org/web/Transactions/54/0963.PDF>, last visited on Mar. 22, 2011, 1 page.

Young, C.S. et al. (2007). "Bone Toxicology Study of Recombinant Human Platelet-Derived Growth Factor-BB (rhPDGF-BB) Injected Locally at the Metatarsus and Femur of Rats," Poster No. 1550, 53rd Annual Meeting of the Orhopaedic Research Society, San Diego, CA, located at <http://www.ors.org/web/Transactions/53/1550.PDF>, last visited on Mar. 22, 2011, 1 page.

Young, C.S. et al. (2008). "Release, Potency and Stability of Clinical Formulation of Recombinant Human Platelet-Derived Growth Factor-BB (rhPDGF-BB) Combined with Two Osteoconductive Materials: Gem OS®1 and Gem 21s®," Poster No. 1693, presented at 54th Annual Meeting of the Orthopaedic Research Society, San Francisco, CA, Mar. 2-5, 2008, one page.

Young, C.S. (2009). "Distribution, Mass Balance and Excretion of $^{125}$Iodine-Labeled Recombinant Human Platelet-Derived Growth Factor BB (rhPDGF-BB) Administered Intravenously to Rats," Poster No. 597, *presented at 55$^{th}$ Annual Meeting of the Orthopaedic Research Society*, Las Vegas, NV, Feb. 22-25, 2009, one page.

\* cited by examiner

COMPOSITIONS AND METHODS FOR TREATING THE VERTEBRAL COLUMN

CROSS REFERENCE TO RELATED APPLICATIONS

This application is a continuation-in-part of International Application No. PCT/US2008/065666, filed on Jun. 3, 2008, which claims priority of U.S. Provisional Patent Application Ser. Nos. 60/933,202, filed Jun. 4, 2007, and 61/026,835 filed Feb. 7, 2008, all of which are incorporated herein by reference in their entirety. This application is also a continuation-in-part of International Application No. PCT/US2007/003582 and U.S. patent application Ser. No. 11/704,685, now U.S. Pat. No. 7,799,754, both of which were filed on Feb. 9, 2007, and both of which claim priority of U.S. Provisional Patent Application Ser. Nos. 60/817,988, filed Jun. 30, 2006, and 60/859,809, filed Nov. 17, 2006, all of which are incorporated herein by reference in their entirety.

FIELD OF THE INVENTION

The present invention relates to compositions and methods useful for treating structures of the vertebral column, including vertebral bodies.

BACKGROUND OF THE INVENTION

Musculoskeletal problems are pervasive throughout the population in all age groups and in both sexes. Half of Americans will need services for fractures at some point in their lifetimes according to a widely published article presented at the 2003 annual meeting of the American Academy of Orthopedic Surgeons (AAOS). More than $10 billion per year is spent in the U.S. on hospital care associated with fracture treatment according to this report.

Vertebral compression fractures (VCFs) are the most common osteoporotic fractures, occurring in about 20% of post-menopausal women (Eastell et al., J Bone Miner Res 1991; 6:207-215). It is estimated that 700,000 VCFs occur annually, and only 250,000 of these are diagnosed and treated. Because these fractures are left untreated, osteoporosis may remain untreated and progress rapidly. Post-menopausal women have a 5-fold increased risk of sustaining another vertebral fracture within the coming year and 2-fold increased risk of other fragility fractures, including hip fractures (Klotzbuecher et al, J Bone Miner Res, 2000; 15:721-739).

VCFs occur when there is a break in one or both of the vertebral body end plates, usually due to trauma, causing failure of the anterior column and weakening the vertebrae from supporting the body during activities of daily living. Vertebral compression fractures caused by osteoporosis can cause debilitating back pain, spinal deformity, and height loss. Both symptomatic and asymptomatic vertebral fractures are associated with increased morbidity and mortality. With the number of aged people at risk for osteoporosis is expected to increase dramatically in the coming decades, accurate identification of VCFs and treatment intervention is necessary to reduce the enormous potential impact of this disease on patients and health care systems.

Traditionally, VCFs caused by osteoporosis have been treated with bed rest, narcotic analgesics, braces, and physical therapy. Bed rest, however, leads to accelerated bone loss and physical deconditioning, further aggravating the patient as well as contributing to the problem of osteoporosis. Moreover, the use of narcotics can worsen the mood and mentation problem that may already be prevalent in the elderly. Additionally, brace wear is not well-tolerated by the elderly. Although the current treatments of osteoporosis such as hormone replacement, bisphosphonates, calcitonin, and parathyroid hormone (PTH) analogs deal with long-term issues, except for calcitonin, they provide no immediate benefit in terms of pain control once a fracture occurs (Kapuscinski et al., Master Med. Pol. 1996; 28:83-86).

Recently, minimally invasive treatments for vertebral body compression fractures, vertebroplasty and kyphoplasty, have been developed to address the issues of pain and fracture stabilization. Vertebroplasty is the filling of a fractured vertebral body with the goals of stabilizing the bone, preventing further collapse, and eliminating acute fracture pain. Vertebroplasty, however, does not attempt to restore vertebral height and/or sagittal alignment. In addition, because there is no void in the bone, vertebral filling is performed under less control with less viscous cement and, as a consequence, filler leaks are common.

Kyphoplasty is a minimally invasive surgical procedure with the goal of safety, improving vertebral height and stabilizing VCF. Guided by x-ray images, an inflatable bone tamp is inflated in the fractured vertebral body. This compacts the inner cancellous bone as it pushes the fractured cortices back toward their normal position. Fixation can then be done by filling the void with a biomaterial under volume control with a more viscous cement. Although kyphoplasty is considered a safe and effective treatment of vertebral compression fractures, biomechanical studies demonstrate that cement augmentation places additional stress on adjacent levels. In fact, this increased stiffness can decrease the ultimate load to failure of adjacent vertebrae by 8 to 30% and provoke subsequent fractures (Berlemann et al., J Bone Joint Surgery BR, 2002; 84:748-52). Compression fracture of one or more vertebral bodies subsequent to vertebroplasty or kyphoplasty is referred to herein as a "secondary vertebral compression fracture."

In a recent clinical study, a higher rate of secondary vertebral compression fracture was observed after kyphoplasty compared with historical data for untreated fractures. Most of these occurred at an adjacent level within 2 months of the index procedure. After this two-month period, there were only occasional secondary vertebral compression fractures which occurred at remote levels. This study confirmed biomechanical studies showing that cement augmentation places additional stress on adjacent level. (Fribourg et al., Incidence of subsequent vertebral fracture after kyphoplasty, Spine, 2004; 20; 2270-76).

Given the increased incidence of the use of minimally invasive surgical techniques for the treatment of vertebral compression fractures, and the predisposition of adjacent vertebrae to undergo secondary compression fracture, an unmet clinical need exists to prophylactically treat and prevent secondary VCFs.

SUMMARY OF THE INVENTION

The present invention provides compositions and methods useful for treating structures of the vertebral column, including vertebral bodies. In some embodiments of the present invention, compositions are provided for promoting bone formation in a vertebral body. In other embodiments, compositions and methods are provided for preventing or decreasing the likelihood of vertebral compression fractures. In another embodiment, methods and compositions are provided for preventing or decreasing the likelihood of secondary vertebral compression fractures associated with vertebroplasty and/or kyphoplasty. The present compositions and methods can be useful in treating vertebral bodies of compromised patients, such as those with osteoporosis, diabetes, or other diseases or conditions.

In one aspect, a composition for promoting bone formation in a vertebral body comprises a solution comprising platelet derived growth factor (PDGF) and biocompatible matrix, wherein the solution is disposed or incorporated in the biocompatible matrix. In some embodiments, the PDGF is absorbed by the biocompatible matrix. In other embodiments, the PDGF is adsorbed onto one or more surfaces of the biocompatible matrix. In a further embodiment, the PDGF is absorbed by the biocompatible matrix and adsorbed onto one or more surfaces of the biocompatible matrix.

In some embodiments, PDGF is present in the solution in a concentration ranging from about 0.01 mg/ml to about 10 mg/ml, from about 0.05 mg/ml to about 5 mg/ml, from about 0.1 mg/ml to about 1.0 mg/ml, or from about 0.2 mg/ml to about 0.4 mg/ml. The concentration of PDGF within the solution may be within any of the concentration ranges stated above.

In some embodiments of the present invention, PDGF comprises PDGF homodimers and heterodimers, including PDGF-AA, PDGF-BB, PDGF-AB, PDGF-CC, PDGF-DD, and mixtures and derivatives thereof. In one embodiment, PDGF comprises PDGF-BB. In another embodiment PDGF comprises a recombinant human (rh) PDGF such as recombinant human PDGF-BB (rhPDGF-BB).

In some embodiments of the present invention, PDGF comprises PDGF fragments. In one embodiment rhPDGF-B comprises the following fragments: amino acid sequences 1-31, 1-32, 33-108, 33-109, and/or 1-108 of the entire B chain. The complete amino acid sequence (1-109) of the B chain of PDGF is provided in FIG. 15 of U.S. Pat. No. 5,516,896. It is to be understood that the rhPDGF compositions of the present invention may comprise a combination of intact rhPDGF-B (1-109) and fragments thereof. Other fragments of PDGF may be employed such as those disclosed in U.S. Pat. No. 5,516,896. In some embodiments, rhPDGF-BB comprises at least 65% of intact rhPDGF-B (1-109).

A biocompatible matrix, according to some embodiments of the present invention, comprises a bone substituting agent (also called a scaffolding material herein) and optionally a biocompatible binder. Bone substituting agents, in some embodiments, comprise calcium phosphate including amorphous calcium phosphate, monocalcium phosphate monohydrate (MCPM), monocalcium phosphate anhydrous (MCPA), dicalcium phosphate dihydrate (DCPD), dicalcium phosphate anhydrous (DCPA), octacalcium phosphate (OCP), α-tricalcium phosphate, β-TCP, hydroxyapatite (OHAp), poorly crystalline hydroxapatite, tetracalcium phosphate (TTCP), heptacalcium decaphosphate, calcium metaphosphate, calcium pyrophosphate dihydrate, calcium pyrophosphate, carbonated calcium phosphate, hydroxyapatite, or derivatives or mixtures thereof. In some embodiments, bone substituting agents comprise calcium sulfate or demineralized bone such as dried cortical or cancellous bone.

In another aspect, the present invention provides a composition for promoting bone formation in a vertebral body comprising a PDGF solution disposed in a biocompatible matrix, wherein the biocompatible matrix comprises a bone scaffolding material and a biocompatible binder. The PDGF solution may have a concentration of PDGF as described above. A bone scaffolding material, in some embodiments, comprises calcium phosphate. In an embodiment, calcium phosphate comprises β-TCP. In one aspect, biocompatible matrices may include calcium phosphate particles with or without biocompatible binders or bone allograft such as demineralized freeze dried bone allograft (DFDBA), mineralized freeze dried bone allograft (FDBA), or particulate demineralized bone matrix (DBM). In another aspect, biocompatible matrices may include bone allograft such as DFDBA, DBM, or other bone allograft materials including cortical bone shapes, such as blocks, wedges, cylinders, or particles, or cancellous bone particles of various shapes and sizes.

Moreover, a biocompatible binder, according to some embodiments of the present invention, comprises proteins, polysaccharides, nucleic acids, carbohydrates, synthetic polymers, or mixtures thereof. In one embodiment, a biocompatible binder comprises collagen. In another embodiment, a biocompatible binder comprises hyaluronic acid.

In another aspect the present invention provides a composition for preventing or decreasing the likelihood of vertebral compression fractures, including secondary vertebral compression fractures. In some embodiments, a composition for preventing or decreasing the likelihood of vertebral compression fractures comprises a solution comprising PDGF and a biocompatible matrix wherein the solution is disposed in the biocompatible matrix. In other embodiments, a composition for preventing or decreasing the likelihood of vertebral compression fractures comprises a PDGF solution disposed in a biocompatible matrix, wherein the biocompatible matrix comprises a bone scaffolding material and a biocompatible binder. In embodiments of a composition for preventing or decreasing the likelihood of vertebral compression fractures, a PDGF solution may have a concentration of PDGF as described above. Moreover, a bone scaffolding material, in some embodiments, comprises calcium phosphate. In an embodiment, calcium phosphate comprises β-tricalcium phosphate. A biocompatible binder, according to some embodiments of the present invention, comprises proteins, polysaccharides, nucleic acids, carbohydrates, synthetic polymers, or mixtures thereof. In one embodiment, a biocompatible binder comprises collagen. In another embodiment, a biocompatible binder comprises collagen, such as bovine collagen.

In some embodiments of the present invention, compositions for promoting bone formation in vertebral bodies and compositions for preventing or reducing the likelihood of vertebral compression fractures further comprise at least one contrast agent. Contrast agents, according to embodiments of the present invention, are substances operable to at least partially provide differentiation of two or more bodily tissues when imaged. Contrast agents, according to some embodiments, comprise cationic contrast agents, anionic contrast agents, nonionic contrast agents, or mixtures thereof. In some embodiments, contrast agents comprise radiopaque contrast agents. Radiopaque contrast agents, in some embodiments, comprise iodo-compounds including (S)—N,N'-bis[2-hydroxy-1-(hydroxymethyl)-ethyl]-2,4,6-triiodo-5-lactamido-isophthalamide (Iopamidol) and derivatives thereof.

In another aspect, the present invention provides a kit comprising a biocompatible matrix in a first package and a solution comprising PDGF in a second package. In some embodiments, the biocompatible matrix comprises a scaffolding material, a scaffolding material and a biocompatible binder, and/or bone allograft such as DFDBA or particulate DBM. In one embodiment, the scaffolding material comprises a calcium phosphate, such as β-TCP. Moreover, in some embodiments, the solution comprises a predetermined concentration of PDGF. The concentration of the PDGF can be predetermined according to the surgical procedure being performed, such as promoting or accelerating bone growth in a vertebral body or preventing or decreasing the likelihood of secondary vertebral compression fractures. Moreover, in some embodiments, the biocompatible matrix can be present in the kit in a predetermined amount. The amount of biocompatible matrix provided by a kit can be dependent on the surgical procedure being performed. In some embodiments, the second package containing the PDGF solution comprises a syringe. A syringe can facilitate disposition of the PDGF solution in the biocompatible matrix. Once the PDGF solution has been disposed in the biocompatible matrix, in some embodiments, the resulting composition can placed in a second syringe and/or cannula and delivered to a vertebral body.

The present invention also provides methods of producing compositions for promoting bone formation in vertebral bodies and preventing or decreasing the likelihood of compression fractures of vertebral bodies, including secondary vertebral compression fractures. In one embodiment, a method for producing such compositions comprises providing a solution comprising PDGF, providing a biocompatible matrix, and disposing the solution in the biocompatible matrix. In some embodiments, a method of producing compositions for promoting bone formation in a vertebral body and preventing or decreasing the likelihood of compression fracture in a vertebral body further comprises providing a contrast agent and disposing the contrast agent in the biocompatible matrix.

In another aspect, the present invention provides methods for promoting or accelerating bone formation in a vertebral body comprising providing a composition comprising a PDGF solution disposed in a biocompatible matrix and applying an effective amount of the composition to at least one vertebral body. Applying the composition to at least one vertebral body, in some embodiments, comprises injecting the composition into the at least one vertebral body.

In another aspect, the present invention provides methods comprising preventing or decreasing the likelihood of vertebral compression fractures, including secondary vertebral compression fractures. Preventing or decreasing the likelihood of vertebral compression fractures, according to embodiments of the present invention comprises providing a composition comprising a PDGF solution disposed in a biocompatible matrix and applying an effective amount of the composition to at least one vertebral body. In some embodiments, applying the composition to at least one vertebral body comprises injecting the composition into the at least one vertebral body. In one embodiment, the composition is applied to a second vertebral body, in some instances an adjacent vertebral body, subsequent to a vertebroplasty or kyphoplasty of a first vertebral body. In some embodiments, a composition comprising a PDGF solution disposed in a biocompatible matrix is applied to at least one high risk vertebral body. "High risk vertebral bodies" (HVB), as used herein, refer to vertebral bodies of vertebrae T5 through T12 as well as L1 through L4, which are at the greatest risk of undergoing secondary vertebral compression fracture.

In some embodiments of methods of the present invention, the biocompatible matrix comprises a bone scaffolding material. In some embodiments, the biocompatible matrix comprises a bone scaffolding material and a biocompatible binder.

In some embodiments, methods for promoting bone formation in vertebral bodies and preventing or decreasing the likelihood of compression fractures of vertebral bodies further comprise providing at least one pharmaceutical composition in addition to the composition comprising a PDGF solution disposed in a biocompatible matrix and administering the at least one pharmaceutical composition locally and/or systemically. The at least one pharmaceutical composition, in some embodiments, comprises vitamins, calcium supplements, or any osteoclast inhibitor known to one of skill in the art, including bisphosphonates. In some embodiments, the at least one pharmaceutical composition is administered locally. In such embodiments, the at least one pharmaceutical composition can be incorporated into the biocompatible matrix or otherwise disposed in and around a vertebral body. In other embodiments, the at least one pharmaceutical composition is administered systemically to a patient. In one embodiment, for example, the at least one pharmaceutical composition is administered orally to a patient. In another embodiment, the at least one pharmaceutical composition is administered intravenously to a patient.

Accordingly, it is an object of the present invention to provide a composition comprising PDGF useful in promoting bone formation in vertebral bodies.

It is another object of the present invention to provide a composition comprising PDGF useful in strengthening vertebral bodies.

It is another object of the present invention to provide a composition comprising PDGF useful in strengthening vertebral bodies of patients with osteoporosis.

It is another object of the present invention to provide a composition comprising PDGF useful in preventing or decreasing the likelihood of vertebral compression fractures, including secondary vertebral compression fractures.

Another object of the present invention is to provide methods for promoting bone formation in vertebral bodies using compositions comprising PDGF.

A further object of the present invention is to provide methods of preventing or decreasing the likelihood of vertebral compression fractures, including secondary vertebral compression fractures, using compositions comprising PDGF.

These and other embodiments of the present invention are described in greater detail in the detailed description which follows. These and other objects, features and advantages of the present invention will become apparent after a review of the following detailed description of the disclosed embodiments and claims.

DETAILED DESCRIPTION

Figure 1:
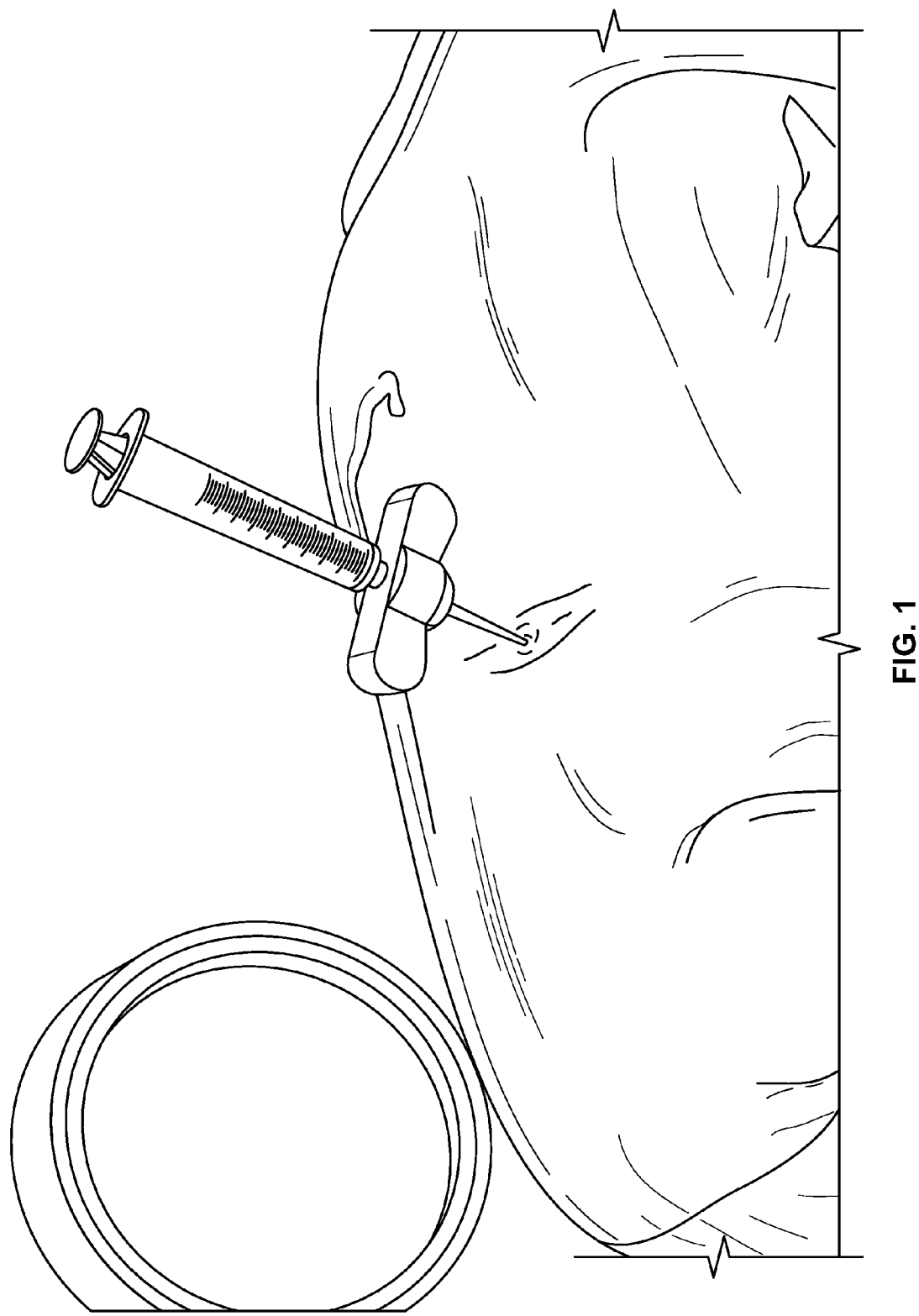
FIG. 1 illustrates a syringe and related apparatus penetrating tissue overlaying a vertebral body to deliver a composition of the present invention to the vertebral body according to an embodiment of the present invention.

The present invention provides compositions and methods useful for treating structures of the vertebral column, including vertebral bodies. According to embodiments described herein, the present invention provides compositions for promoting bone formation in a vertebral body and compositions for preventing or decreasing the likelihood of vertebral compression fractures, including secondary vertebral compression fractures. In one embodiment, the compositions comprise a solution comprising PDGF and a biocompatible matrix, wherein the solution is disposed in the biocompatible matrix. In another embodiment, the compositions comprise a PDGF solution disposed in a biocompatible matrix, wherein the biocompatible matrix comprises a bone scaffolding material and a biocompatible binder. In one aspect, biocompatible matrices include calcium phosphate particles with or without biocompatible binders or bone allograft such as DFDBA or particulate DBM. In another aspect, biocompatible matrices may include DFDBA or DBM.

Turning now to components that can be included in various embodiments of the present invention, compositions of the present invention comprise a solution comprising PDGF.

PDGF Solutions

PDGF plays an important role in regulating cell growth and migration. PDGF, as with other growth factors, binds with the extracellular domains of receptor tyrosine kinases. The binding of PDGF to these transmembrane proteins activate the kinase activity of their catalytic domains located on the cytosolic side of the membrane. By phosphorylating tyrosine residues of target proteins, the kinases induce a variety of cellular processes that include cell growth and extracellular matrix production.

In one aspect, a composition provided by the present invention comprises a solution comprising PDGF and a biocompatible matrix, wherein the solution is disposed or incorporated in the biocompatible matrix. In some embodiments, PDGF is present in the solution in a concentration ranging from about 0.01 mg/ml to about 10 mg/ml, from about 0.05 mg/ml to about 5 mg/ml, or from about 0.1 mg/ml to about 1.0 mg/ml. PDGF may be present in the solution at any concentration within these stated ranges including the upper limit and lower limit of each range. In other embodiments, PDGF is present in the solution at any one of the following concentrations: about 0.05 mg/ml; about 0.1 mg/ml; about 0.15 mg/ml; about 0.2 mg/ml; about 0.25 mg/ml; about 0.3 mg/ml; about 0.35 mg/ml; about 0.4 mg/ml; about 0.45 mg/ml; about 0.5 mg/ml, about 0.55 mg/ml, about 0.6 mg/ml, about 0.65 mg/ml, about 0.7 mg/ml; about 0.75 mg/ml; about 0.8 mg/ml; about 0.85 mg/ml; about 0.9 mg/ml; about 0.95 mg/ml; or about 1.0 mg/ml. In some embodiments, PDGF is present in the solution in a concentration ranging from about 0.2 mg/ml to about 2 mg/ml, from about 0.3 mg/ml to about 3 mg/ml, from about 0.4 mg/ml to about 4 mg/ml, or from about 0.5 mg/ml to about 5 mg/ml. It is to be understood that these concentrations are simply examples of particular embodiments, and that the concentration of PDGF may be within any of the concentration ranges stated above including the upper limit and the lower limit of each range.

Various amounts of PDGF may be used in the compositions of the present invention. Amounts of PDGF that could be used include amounts in the following ranges: about 1 µg to about 50 mg, about 10 µg to about 25 mg, about 100 µg to about 10 mg, and about 250 µg to about 5 mg.

The concentration of PDGF or other growth factors in embodiments of the present invention can be determined by using an enzyme-linked immunoassay as described in U.S. Pat. Nos. 6,221,625, 5,747,273, and 5,290,708, or any other assay known in the art for determining PDGF concentration. When provided herein, the molar concentration of PDGF is determined based on the molecular weight (MW) of PDGF dimer (e.g., PDGF-BB; MW about 25 kDa).

In some embodiments of the present invention, PDGF comprises PDGF homodimers and heterodimers, including PDGF-AA, PDGF-BB, PDGF-AB, PDGF-CC, PDGF-DD, and mixtures and derivatives thereof. In one embodiment, for example, PDGF comprises PDGF-BB. In another embodiment PDGF comprises a recombinant human PDGF, such as rhPDGF-BB. In some embodiments, PDGF comprises mixtures of the various homodimers and/or heterodimers. Embodiments of the present invention contemplate any combination of PDGF-AA, PDGF-BB, PDGF-AB, PDGF-CC, and/or PDGF-DD.

PDGF, in some embodiments, can be obtained from natural sources. In other embodiments, PDGF can be produced by recombinant DNA techniques. In other embodiments, PDGF or fragments thereof may be produced using peptide synthesis techniques known to one of ordinary skill in the art, such as solid phase peptide synthesis. When obtained from natural sources, PDGF can be derived from biological fluids. Biological fluids, according to some embodiments, can comprise any treated or untreated fluid associated with living organisms including blood Biological fluids, in another embodiment, can also comprise blood components including platelet concentrate (PC), apheresed platelets, platelet-rich plasma (PRP), plasma, serum, fresh frozen plasma (FFP), and buffy coat (BC). Biological fluids, in a further embodiment, can comprise platelets separated from plasma and resuspended in a physiological fluid.

When produced by recombinant DNA techniques, a DNA sequence encoding a single monomer (e.g., PDGF B-chain or A-chain), in some embodiments, can be inserted into cultured prokaryotic or eukaryotic cells for expression to subsequently produce the homodimer (e.g. PDGF-BB or PDGF-AA). In other embodiments, a PDGF heterodimer can be generated by inserting DNA sequences encoding for both monomeric units of the heterodimer into cultured prokaryotic or eukaryotic cells and allowing the translated monomeric units to be processed by the cells to produce the heterodimer (e.g. PDGF-AB). Commercially available GMP recombinant PDGF-BB can be obtained commercially from Novartis Corporation (Emeryville, Calif.). Research grade rhPDGF-BB can be obtained from multiple sources including R&D Systems, Inc. (Minneapolis, Minn.), BD Biosciences (San Jose, Calif.), and Chemicon, International (Temecula, Calif.). In some embodiments, monomeric units can be produced in prokaryotic cells in a denatured form, wherein the denatured form is subsequently refolded into an active molecule.

In embodiments of the present invention, PDGF comprises PDGF fragments. In one embodiment rhPDGF-B comprises the following fragments: amino acid sequences 1-31, 1-32, 33-108, 33-109, and/or 1-108 of the entire B chain. The complete amino acid sequence (1-109) of the B chain of PDGF is provided in FIG. 15 of U.S. Pat. No. 5,516,896. It is to be understood that the rhPDGF compositions of the present invention may comprise a combination of intact rhPDGF-B (1-109) and fragments thereof. Other fragments of PDGF may be employed such as those disclosed in U.S. Pat. No. 5,516,896. In accordance with one embodiment, the rhPDGF-BB comprises at least 60% of intact rhPDGF-B (1-109). In another embodiment, the rhPDGF-BB comprises at least 65%, 75%, 80%, 85%, 90%, 95%, or 99% of intact rhPDGF-B (1-109).

In some embodiments of the present invention, PDGF can be purified. Purified PDGF, as used herein, comprises compositions having greater than about 95% by weight PDGF prior to incorporation in solutions of the present invention. The solution may be any pharmaceutically acceptable solution. In other embodiments, the PDGF can be substantially purified. Substantially purified PDGF, as used herein, comprises compositions having about 5% to about 95% by weight PDGF prior to incorporation into solutions of the present invention. In one embodiment, substantially purified PDGF comprises compositions having about 65% to about 95% by weight PDGF prior to incorporation into solutions of the present invention. In other embodiments, substantially purified PDGF comprises compositions having about 70% to about 95%, about 75% to about 95%, about 80% to about 95%, about 85% to about 95%, or about 90% to about 95%, by weight PDGF, prior to incorporation into solutions of the present invention. Purified PDGF and substantially purified PDGF may be incorporated into scaffolds and binders.

In a further embodiment, PDGF can be partially purified. Partially purified PDGF, as used herein, comprises compositions having PDGF in the context of platelet rich plasma (PRP), fresh frozen plasma (FFP), or any other blood product that requires collection and separation to produce PDGF. Embodiments of the present invention contemplate that any of the PDGF isoforms provided herein, including homodimers and heterodimers, can be purified or partially purified. Compositions of the present invention containing PDGF mixtures may contain PDGF isoforms or PDGF fragments in partially purified proportions. Partially purified and purified PDGF, in some embodiments, can be prepared as described in U.S. patent application Ser. No. 11/159,533 (Publication No: 20060084602).

In some embodiments, solutions comprising PDGF are formed by solubilizing PDGF in one or more buffers. Buffers suitable for use in PDGF solutions of the present invention can comprise, but are not limited to, carbonates, phosphates (e.g. phosphate buffered saline), histidine, acetates (e.g. sodium acetate), acidic buffers such as acetic acid and HCl, and organic buffers such as lysine, Tris buffers (e.g. tris(hydroxymethyl)aminoethane), N-2-hydroxyethylpiperazine-N'-2-ethanesulfonic acid (HEPES), and 3-(N-morpholino) propanesulfonic acid (MOPS). Buffers can be selected based on biocompatibility with PDGF and the buffer's ability to impede undesirable protein modification. Buffers can additionally be selected based on compatibility with host tissues. In one embodiment, sodium acetate buffer is used. The buffers may be employed at different molarities, for example, about 0.1 mM to about 100 mM, about 1 mM to about 50 mM, about 5 mM to about 40 mM, about 10 mM to about 30 mM, or about 15 mM to about 25 mM, or any molarity within these ranges. In some embodiments, an acetate buffer is employed at a molarity of about 20 mM.

In another embodiment, solutions comprising PDGF are formed by solubilizing lyophilized PDGF in water, wherein prior to solubilization the PDGF is lyophilized from an appropriate buffer.

Solutions comprising PDGF, according to embodiments of the present invention, can have a pH ranging from about 3.0 to about 8.0. In one embodiment, a solution comprising PDGF has a pH ranging from about 5.0 to about 8.0, from about 5.5 to about 7.0, or from about 5.5 to about 6.5, or any value within these ranges. The pH of solutions comprising PDGF, in some embodiments, can be compatible with the prolonged stability and efficacy of PDGF or any other desired biologically active agent. PDGF is more stable in an acidic environment. Therefore, in accordance with one embodiment the present invention comprises an acidic storage formulation of a PDGF solution. In accordance with this embodiment, the PDGF solution preferably has a pH from about 3.0 to about 7.0 or from about 4.0 to about 6.5. The biological activity of PDGF, however, can be optimized in a solution having a neutral pH range. Therefore, in a further embodiment, the present invention comprises a neutral pH formulation of a PDGF solution. In accordance with this embodiment, the PDGF solution preferably has a pH from about 5.0 to about 8.0, from about 5.5 to about 7.0, or from about 5.5 to about 6.5. In accordance with a method of the present invention, an acidic PDGF solution is reformulated to a neutral pH composition, wherein such composition is then used to treat bone and promote bone growth and/or healing. In accordance with some embodiments of the present invention, the PDGF utilized in the solutions is rh-PDGF-BB. In a further embodiment, the pH of the PDGF containing solution may be altered to optimize the binding kinetics of PDGF to a matrix substrate or linker. If desired, the pH of the material equilibrates to adjacent material, the bound PDGF may become labile.

The pH of solutions comprising PDGF, in some embodiments, can be controlled by the buffers recited herein. Various proteins demonstrate different pH ranges in which they are stable. Protein stabilities are primarily reflected by isoelectric points and charges on the proteins. The pH range can affect the conformational structure of a protein and the susceptibility of a protein to proteolytic degradation, hydrolysis, oxidation, and other processes that can result in modification to the structure and/or biological activity of the protein.

In some embodiments, solutions comprising PDGF can further comprise additional components, such as other biologically active agents. In other embodiments, solutions comprising PDGF can further comprise cell culture media, other stabilizing proteins such as albumin, antibacterial agents, protease inhibitors [e.g., ethylenediaminetetraacetic acid (EDTA), ethylene glycol-bis(beta-aminoethylether)-N,N,N',N'-tetraacetic acid (EGTA), aprotinin, $\epsilon$-aminocaproic acid (EACA), etc.] and/or other growth factors such as fibroblast growth factors (FGFs), epidermal growth factors (EGFs), transforming growth factors (TGFs), keratinocyte growth factors (KGFs), insulin-like growth factors (IGFs), hepatocyte growth factors (HGFs), bone morphogenetic proteins (BMPs), or other PDGFs including compositions of PDGF-AA, PDGF-BB, PDGF-AB, PDGF-CC and/or PDGF-DD.

In addition to solutions comprising PDGF, compositions of the present invention also comprise a biocompatible matrix in which to dispose the PDGF solutions and may also comprise a biocompatible binder either with or without addition of a biocompatible matrix.

Biocompatible Matrix

Bone Scaffolding Material

A biocompatible matrix, according to embodiments of the present invention, comprises a bone scaffolding material. It is to be understood that the terms bone scaffolding material and bone substituting agent are used interchangeably in the present application. The bone scaffolding material provides the framework or scaffold for new bone and tissue growth to occur. In some embodiments, a bone scaffolding material has multidirectional and interconnected pores of varying diameters. In some embodiments, a bone scaffolding material comprises a plurality of pockets and non-interconnected pores in addition to the interconnected pores. A bone scaffolding material, in some embodiments, is one that can permanently or temporarily replace bone. Following implantation, the bone scaffolding material can be retained by the body or it can be resorbed by the body and replaced by bone.

A bone scaffolding material, in some embodiments, comprises at least one calcium phosphate. In other embodiments, a bone scaffolding material can comprise a plurality of calcium phosphates. Calcium phosphates suitable for use as a bone scaffolding material, in embodiments of the present invention, have a calcium to phosphorus atomic ratio ranging from 0.5 to 2.0. In some embodiments, a bone scaffolding material comprises an allograft such as DFDBA, FDBA, or particulate DBM. In some embodiments, a bone scaffolding material comprises mineralized bone allograft, mineralized bone, mineralized deproteinized xenograft, or demineralized bone.

Non-limiting examples of calcium phosphates suitable for use as bone scaffolding materials comprise amorphous calcium phosphate, monocalcium phosphate monohydrate (MCPM), monocalcium phosphate anhydrous (MCPA), dicalcium phosphate dihydrate (DCPD), dicalcium phosphate anhydrous (DCPA), octacalcium phosphate (OCP), α-tricalcium phosphate, β-TCP, hydroxyapatite (OHAp), poorly crystalline hydroxapatite, tetracalcium phosphate (TTCP), heptacalcium decaphosphate, calcium metaphosphate, calcium pyrophosphate dihydrate, calcium pyrophosphate, carbonated calcium phosphate, hydroxyapatite, or derivatives or mixtures thereof.

In some embodiments, a bone scaffolding material comprises a polymeric material. A polymeric scaffold, in some embodiments, comprises collagen, polylactic acid, poly(L-lactide), poly(D,L-lactide), polyglycolic acid, poly(L-lactide-co-glycolide), poly(L-lactide-co-D,L-lactide), polyacrylate, polymethacrylate, polymethylmethacrylate, chitosan, or combinations or derivatives thereof.

In some embodiments, a bone scaffolding material comprises porous structure. Porosity is a desirable characteristic as it facilitates cell migration and infiltration into the scaffolding material so that the infiltrating cells can secrete extracellular bone matrix. Porosity also provides access for vascularization. Porosity also provides a high surface area for enhanced resorption and release of active substances as well as increased cell-matrix interaction. A bone scaffolding material, in some embodiments, can be sized and shaped prior to use. In some embodiments, the bone scaffolding material can be provided in a shape suitable for implantation.

Porous bone scaffolding materials, according to some embodiments, can comprise pores having diameters ranging from about 1 μm to about 1 mm. In one embodiment, a bone scaffolding material comprises macropores having diameters ranging from about 100 μm to about 1 mm or greater. In another embodiment, a bone scaffolding material comprises mesopores having diameters ranging from about 10 μm to about 100 μm. In a further embodiment, a bone scaffolding material comprises micropores having diameters less than about 10 μm. Embodiments of the present invention contemplate bone scaffolding materials comprising macropores, mesopores, and micropores or any combination thereof.

A porous bone scaffolding material, in one embodiment, has a porosity greater than about 25% or greater than about 40%. In another embodiment, a porous bone scaffolding material has a porosity greater than about 50%, greater than about 60%, greater than about 65%, greater than about 70%, greater than about 80%, or greater than about 85%. In a further embodiment, a porous bone scaffolding material has a porosity greater than about 90%. In some embodiments, a porous bone scaffolding material comprises a porosity that facilitates cell migration into the scaffolding material.

In some embodiments, a bone scaffolding material comprises a plurality of particles. A bone scaffolding material, for example, can comprise a plurality of calcium phosphate particles. Particles of a bone scaffolding material, in some embodiments, can individually demonstrate any of the pore diameters and porosities provided here for the bone scaffolding material. In other embodiments, particles of a bone scaffolding material can form an association to produce a matrix having any of the pore diameters or porosities provided herein for the bone scaffolding material.

Bone scaffolding particles may be mm, μm, or submicron (nm) in size. Bone scaffolding particles, in one embodiment, have an average diameter ranging from about 1 μm to about 5 mm. In other embodiments, particles have an average diameter ranging from about 1 mm to about 2 mm, from about 1 mm to about 3 mm, or from about 250 μm to about 750 μm. Bone scaffolding particles, in another embodiment, have an average diameter ranging from about 100 μm to about 300 μm. In a further embodiment, bone scaffolding particles have an average diameter ranging from about 75 μm to about 300 μm. In additional embodiments, bone scaffolding particles have an average diameter less than about 25 μm, less than about 1 μm, or less than about 1 mm. In some embodiments, scaffolding particles have an average diameter ranging from about 100 μm to about 5 mm or from about 100 μm to about 3 mm. In other embodiments, bone scaffolding particles have an average diameter ranging from about 250 μm to about 2 mm, from about 250 μm to about 1 mm, or from about 200 μm to about 3 mm. Particles may also be in the range of about 1 nm to about 1 μm, less than about 500 nm, or less than about 250 nm.

Bone scaffolding materials, according to some embodiments, can be provided in a shape suitable for implantation (e.g., a sphere, a cylinder, or a block). In other embodiments, bone scaffolding materials are moldable, extrudable and/or injectable. Moldable, extrudable, and injectable bone scaffolding materials can facilitate efficient placement of compositions of the present invention in and around vertebral bodies. In some embodiments, bone scaffolding materials are flowable. Flowable bone scaffolding materials, in some embodiments, can be applied vertebral bodies through a syringe and needle or cannula. In some embodiments, bone scaffolding materials harden in vivo.

In some embodiments, bone scaffolding materials are bioresorbable. A bone scaffolding material, in one embodiment, can be at least 30%, 40%, 50%, 60%, 70%, 75%, or 90% resorbed within one year subsequent to in vivo implantation. In another embodiment, a bone scaffolding material can be resorbed at least 5%, 10%, 20%, 30%, 40%, 50%, 60%, 70%, 75%, or 90% within 1, 3, 6, 9, 12, or 18 months of in vivo implantation. In some embodiments, a bone scaffolding material is greater than 90% resorbed within 1, 3, 6, 9, 12, or 18 months of in vivo implantation. Bioresorbability will be dependent on: (1) the nature of the matrix material (i.e., its chemical make up, physical structure and size); (2) the location within the body in which the matrix is placed; (3) the amount of matrix material that is used; (4) the metabolic state of the patient (diabetic/non-diabetic, osteoporotic, smoker, old age, steroid use, etc.); (5) the extent and/or type of injury treated; and (6) the use of other materials in addition to the matrix such as other bone anabolic, catabolic and anti-catabolic factors.

Bone Scaffolding Comprising β-Tricalcium Phosphate (β-TCP)

A bone scaffolding material for use as a biocompatible matrix can comprise β-TCP. β-TCP, according to some embodiments, can comprise a porous structure having multi-directional and interconnected pores of varying diameters. In some embodiments, β-TCP comprises a plurality of pockets and non-interconnected pores of various diameters in addition to the interconnected pores. The porous structure of β-TCP, in one embodiment, comprises macropores having diameters ranging from about 100 μm to about 1 mm or greater, mesopores having diameters ranging from about 10

μm to about 100 μm, and micropores having diameters less than about 10 μm. Macropores and micropores of the β-TCP can facilitate osteoinduction and osteoconduction while macropores, mesopores and micropores can permit fluid communication and nutrient transport to support bone regrowth throughout the β-TCP biocompatible matrix.

In comprising a porous structure, β-TCP, in some embodiments, can have a porosity greater than 25% or greater than about 40%. In other embodiments, β-TCP can have a porosity greater than 50%, greater than about 60%, greater than about 65%, greater than about 70%, greater than about 75%, greater than about 80%, or greater than about 85%. In a further embodiment, β-TCP can have a porosity greater than 90%. In some embodiments, β-TCP can have a porosity that facilitates cell migration into the β-TCP.

In some embodiments, a β-TCP bone scaffolding material comprises β-TCP particles. β-TCP particles, in some embodiments, can individually demonstrate any of the pore diameters, pore structures, and porosities provided herein for scaffolding materials.

β-TCP particles, in one embodiment have an average diameter ranging from about 1 μm to about 5 mm. In other embodiments, β-TCP particles have an average diameter ranging from about 1 mm to about 2 mm, from about 1 mm to about 3 mm, from about 100 μm to about 5 mm, from about 100 μm to about 3 mm, from about 250 μm to about 2 mm, from about 250 μm to about 750 μm, from about 250 μm to about 1 mm, from about 250 μm to about 2 mm, or from about 200 μm to about 3 mm. In another embodiment, β-TCP particles have an average diameter ranging from about 100 μm to about 300 μm. In some embodiments, β-TCP particles have an average diameter ranging from about 75 μm to about 300 μm. In some embodiments, β-TCP particles have an average diameter of less than about 25 μm, less than about 1 μm, or less than about 1 mm. In some embodiments, β-TCP particles have an average diameter ranging from about 1 nm to about 1 μm. In a further embodiment, β-TCP particles have an average diameter less than about 500 nm or less than about 250 nm.

A biocompatible matrix comprising a β-TCP bone scaffolding material, in some embodiments, can be provided in a shape suitable for implantation (e.g., a sphere, a cylinder, or a block). In other embodiments, a β-TCP bone scaffolding material can be moldable, extrudable, and/or flowable thereby facilitating application of the matrix to vertebral bodies. Flowable matrices may be applied through syringes, tubes, cannulas, or spatulas.

A β-TCP bone scaffolding material, according to some embodiments, is bioresorbable. In one embodiment, a β-TCP bone scaffolding material can be at least 30%, 40%, 50%, 60%, 65%, 70%, 75%, 80%, or 85% resorbed one year subsequent to in vivo implantation. In another embodiment, a β-TCP bone scaffolding material can be greater than 90% resorbed one year subsequent to in vivo implantation.

Bone Scaffolding Material and Biocompatible Binder

In another embodiment, a biocompatible matrix comprises a bone scaffolding material and a biocompatible binder. Bone scaffolding materials in embodiments of a biocompatible matrix further comprising a biocompatible binder are consistent with those provided hereinabove.

Biocompatible binders, according to some embodiments, can comprise materials operable to promote cohesion between combined substances. A biocompatible binder, for example, can promote adhesion between particles of a bone scaffolding material in the formation of a biocompatible matrix. In certain embodiments, the same material may serve as both a scaffolding material. In some embodiments, for example, polymeric materials described herein such as collagen and chitosan may serve as both scaffolding material and a binder.

Biocompatible binders, in some embodiments, can comprise collagen, polysaccharides, nucleic acids, carbohydrates, proteins, polypeptides, poly(α-hydroxy acids), poly (lactones), poly(amino acids), poly(anhydrides), polyurethanes, poly(orthoesters), poly(anhydride-co-imides), poly(orthocarbonates), poly(α-hydroxy alkanoates), poly(dioxanones), poly(phosphoesters), polylactic acid, poly (L-lactide) (PLLA), poly(D,L-lactide) (PDLLA), polyglycolide (PGA), poly(lactide-co-glycolide (PLGA), poly(L-lactide-co-D,L-lactide), poly(D,L-lactide-co-trimethylene carbonate), polyglycolic acid, polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate)polyamide, and copolymers and mixtures thereof.

Biocompatible binders, in other embodiments, can comprise alginic acid, arabic gum, guar gum, xantham gum, gelatin, chitin, chitosan, chitosan acetate, chitosan lactate, chondroitin sulfate, N,O-carboxymethyl chitosan, a dextran (e.g., α-cyclodextrin, β-cyclodextrin, γ-cyclodextrin, or sodium dextran sulfate), fibrin glue, lecithin, phosphatidylcholine derivatives, glycerol, hyaluronic acid, sodium hyaluronate, a cellulose (e.g., methylcellulose, carboxymethylcellulose, hydroxypropyl methylcellulose, or hydroxyethyl cellulose), a glucosamine, a proteoglycan, a starch (e.g., hydroxyethyl starch or starch soluble), lactic acid, pluronic acids, sodium glycerophosphate, glycogen, a keratin, silk, and derivatives and mixtures thereof.

In some embodiments, a biocompatible binder is water-soluble. A water-soluble binder can dissolve from the biocompatible matrix shortly after its implantation, thereby introducing macroporosity into the biocompatible matrix. Macroporosity, as discussed herein, can increase the osteoconductivity of the implant material by enhancing the access and, consequently, the remodeling activity of the osteoclasts and osteoblasts at the implant site.

In some embodiments, a biocompatible binder can be present in a biocompatible matrix in an amount ranging from about 5 weight percent to about 50 weight percent of the matrix. In other embodiments, a biocompatible binder can be present in an amount ranging from about 10 weight percent to about 40 weight percent of the biocompatible matrix. In another embodiment, a biocompatible binder can be present in an amount ranging from about 15 weight percent to about 35 weight percent of the biocompatible matrix. In a further embodiment, a biocompatible binder can be present in an amount of about 20 weight percent of the biocompatible matrix. In another embodiment, a biocompatible binder can be present in a biocompatible matrix in an amount greater than about 50 weight percent or 60 weight percent of the matrix. In one embodiment, a biocompatible binder can be present in a biocompatible matrix in an amount up to about 99 weight percent of the matrix.

A biocompatible matrix comprising a bone scaffolding material and a biocompatible binder, according to some embodiments, can be flowable, moldable, and/or extrudable. In such embodiments, a biocompatible matrix can be in the form of a paste or putty. A biocompatible matrix in the form of a paste or putty, in one embodiment, can comprise particles of a bone scaffolding material adhered to one another by a biocompatible binder.

A biocompatible matrix in paste or putty form can be molded into the desired implant shape or can be molded to the contours of the implantation site. In one embodiment, a biocompatible matrix in paste or putty form can be injected into an implantation site with a syringe or cannula.

In some embodiments, a biocompatible matrix in paste or putty form does not harden and retains a flowable and moldable form subsequent to implantation. In other embodiments, a paste or putty can harden subsequent to implantation, thereby reducing matrix flowability and moldability.

A biocompatible matrix comprising a bone scaffolding material and a biocompatible binder, in some embodiments, can also be provided in a predetermined shape including a block, sphere, or cylinder or any desired shape, for example a shape defined by a mold or a site of application.

A biocompatible matrix comprising a bone scaffolding material and a biocompatible binder, in some embodiments, is bioresorbable. A biocompatible matrix, in such embodiments, can be resorbed within one year of in vivo implantation. In another embodiment, a biocompatible matrix comprising a bone scaffolding material and a biocompatible binder can be resorbed within 1, 3, 6, or 9 months of in vivo implantation. In some embodiments, a biocompatible matrix comprising a scaffolding material and a biocompatible binder can be resorbed within 1, 3, or six years of in vivo implantation. Bioresorbablity will be dependent on: (1) the nature of the matrix material (i.e., its chemical make up, physical structure and size); (2) the location within the body in which the matrix is placed; (3) the amount of matrix material that is used; (4) the metabolic state of the patient (diabetic/non-diabetic, osteoporotic, smoker, old age, steroid use, etc.); (5) the extent and/or type of injury treated; and (6) the use of other materials in addition to the matrix such as other bone anabolic, catabolic and anti-catabolic factors.

Biocompatible Matrix Comprising β-TCP and Collagen

In some embodiments, a biocompatible matrix can comprise a β-TCP bone scaffolding material and a biocompatible collagen binder. β-TCP bone scaffolding materials suitable for combination with a collagen binder are consistent with those provided hereinabove.

A collagen binder, in some embodiments, can comprise any type of collagen, including Type I, Type II, and Type III collagens. In one embodiment, a collagen binder comprises a mixture of collagens, such as a mixture of Type I and Type II collagen. In other embodiments, a collagen binder is soluble under physiological conditions. Other types of collagen present in bone or musculoskeletal tissues may be employed. Recombinant, synthetic and naturally occurring forms of collagen may be used in the present invention.

A biocompatible matrix, according to some embodiments, can comprise a plurality of β-TCP particles adhered to one another with a collagen binder. In some embodiments, β-TCP particles for combination with a collagen binder have an average diameter ranging from about 1 μm to about 5 mm. In other embodiments, β-TCP particles have an average diameter ranging from about 1 mm to about 2 mm, from about 1 mm to about 3 mm, from about 100 μm to about 5 mm, from about 100 μm to about 3 mm, from about 250 μm to about 2 mm, from about 250 μm to about 750 μm, from about 250 μm to about 1 mm, from about 250 μm to about 2 mm, or from about 200 μm to about 3 mm. In another embodiment, β-TCP particles have an average diameter ranging from about 100 μm to about 300 μm. In some embodiments, β-TCP particles have an average diameter ranging from about 75 μm to about 300 μm. In some embodiments, β-TCP particles have an average diameter of less than about 25 μm, less than about 1 μm, or less than about 1 mm. In some embodiments, β-TCP particles have an average diameter ranging from about 1 nm to about 1 μm. In a further embodiment, β-TCP particles have an average diameter less than about 500 nm or less than about 250 nm.

β-TCP particles, in some embodiments, can be adhered to one another by the collagen binder so as to produce a biocompatible matrix having a porous structure. In some embodiments, the porous structure of a biocompatible matrix comprising β-TCP particles and a collagen binder demonstrates multidirectional and interconnected pores of varying diameters. In some embodiments, a the biocompatible matrix comprises a plurality of pockets and non-interconnected pores of various diameters in addition to the interconnected pores.

In some embodiments, a biocompatible matrix comprising β-TCP particles and a collagen binder can comprise pores having diameters ranging from about 1 μm to about 1 mm. A biocompatible matrix comprising β-TCP particles and a collagen binder can comprise macropores having diameters ranging from about 100 μm to about 1 mm or greater, mesopores having diameters ranging from about 10 μm to 100 μm, and micropores having diameters less than about 10 μm.

A biocompatible matrix comprising β-TCP particles and a collagen binder can have a porosity greater than about 25% or greater than about 40%. In another embodiment, the biocompatible matrix can have a porosity greater than about 50%, greater than about 65%, greater than about 70%, greater than about 75%, greater than about 80%, or greater than about 85%. In a further embodiment, the biocompatible matrix can have a porosity greater than about 90%. In some embodiments, the biocompatible matrix can have a porosity that facilitates cell migration into the matrix.

In some embodiments, the β-TCP particles can individually demonstrate any of the pore diameters, pore structures, and porosities provided herein for a biocompatible matrix comprising the β-TCP and collagen binder.

A biocompatible matrix comprising β-TCP particles, in some embodiments, can comprise a collagen binder in an amount ranging from about 5 weight percent to about 50 weight percent of the matrix. In other embodiments, a collagen binder can be present in an amount ranging from about 10 weight percent to about 40 weight percent of the biocompatible matrix. In another embodiment, a collagen binder can be present in an amount ranging from about 15 weight percent to about 35 weight percent of the biocompatible matrix. In a further embodiment, a collagen binder can be present in an amount of about 20 weight percent of the biocompatible matrix.

A biocompatible matrix comprising β-TCP particles and a collagen binder, according to some embodiments, can be flowable, moldable, and/or extrudable. In such embodiments, the biocompatible matrix can be in the form of a paste or putty. A paste or putty can be molded into the desired implant shape or can be molded to the contours of the implantation site. In one embodiment, a biocompatible matrix in paste or putty form comprising β-TCP particles and a collagen binder can be injected into an implantation site with a syringe or cannula.

In some embodiments, a biocompatible matrix in paste or putty form comprising β-TCP particles and a collagen binder can retain a flowable and moldable form when implanted. In other embodiments, the paste or putty can harden subsequent to implantation, thereby reducing matrix flowability and moldability.

A biocompatible matrix comprising β-TCP particles and a collagen binder, in some embodiments, can be provided in a predetermined shape such as a block, sphere, or cylinder.

A biocompatible matrix comprising β-TCP particles and a collagen binder can be resorbable. In one embodiment, a biocompatible matrix comprising β-TCP particles and a collagen binder can be at least 75% resorbed one year subsequent to in vivo implantation. In another embodiment, a biocompatible matrix comprising β-TCP particles and a collagen binder can be greater than 90% resorbed one year subsequent to in vivo implantation.

A solution comprising PDGF can be disposed in a biocompatible matrix to produce a composition for treating structures of the vertebral column according to embodiments described herein.

In some embodiments, compositions comprising a PDGF solution disposed in a biocompatible matrix for promoting bone formation in a vertebral body and preventing or reducing the likelihood of vertebral compression fractures, as described herein, further comprise at least one contrast agent. Contrast agents, according to some embodiments, comprise cationic contrast agents, anionic contrast agents, nonionic contrast agents or mixtures thereof. In some embodiments, contrast agents comprise radiopaque contrast agents. Radiopaque contrast agents, in some embodiments, comprise iodo-compounds including (S)—N,N'-bis[2-hydroxy-1-(hydroxymethyl)-ethyl]-2,4,6-triiodo-5-lactamidoisophthalamide (Iopamidol) and derivatives thereof.

Disposing PDGF Solution in a Biocompatible Matrix

The present invention provides methods for producing compositions for promoting bone formation in a vertebral body and preventing or reducing the likelihood of compression fractures of vertebral bodies, including secondary vertebral fractures. In one embodiment, a method for producing such compositions comprises providing a solution comprising PDGF, providing a biocompatible matrix, and disposing the solution in the biocompatible matrix. PDGF solutions and biocompatible matrices suitable for combination are consistent with those described hereinabove.

In some embodiments, a PDGF solution can be disposed in a biocompatible matrix by soaking the biocompatible matrix in the PDGF solution. A PDGF solution, in another embodiment, can be disposed in a biocompatible matrix by injecting the biocompatible matrix with the PDGF solution. In some embodiments, injecting a PDGF solution can comprise disposing the PDGF solution in a syringe and expelling the PDGF solution into the biocompatible matrix to saturate the biocompatible matrix.

In some embodiments, the PDGF is absorbed into the pores of the biocompatible matrix. In some embodiments, the PDGF is adsorbed onto one or more surfaces of the biocompatible matrix, including surfaces within pores of the biocompatible matrix.

The biocompatible matrix, according to some embodiments, can be in a predetermined shape, such as a brick or cylinder, prior to receiving a PDGF solution. Subsequent to receiving a PDGF solution, the biocompatible matrix can have a paste or putty form that is flowable, extrudable, and/or injectable. In other embodiments, the biocompatible matrix can already demonstrate a flowable paste or putty form prior to receiving a solution comprising PDGF. Flowable, extrudable, and/or injectable forms of compositions comprising a PDGF solution disposed in a biocompatible matrix are advantageous for use in methods of the present application as they can applied to vertebral bodies with syringes and/or cannulas.

In some embodiments, methods of producing compositions for promoting bone formation in vertebral bodies and preventing or decreasing the likelihood of compression fractures in vertebral bodies further comprise providing at least one contrast agent and disposing the at least one contrast agent in the biocompatible matrix. In some embodiments, disposing at least one contrast agent in a biocompatible matrix comprises combining the at least one contrast agent with a PDGF solution and injecting the biocompatible matrix with the PDGF/contrast agent solution.

In another embodiment, disposing at least one contrast agent in a biocompatible matrix comprises combining the at least one contrast agent with a PDGF solution and soaking the biocompatible matrix in the PDGF/contrast agent solution. Alternatively, in some embodiments, a contrast agent is disposed in a biocompatible matrix independent of the PDGF solution.

Contrast agents, according to some embodiments of the present invention, facilitate placement or application of compositions of the present invention in and around vertebral bodies. Contrast agents, according to some embodiments, comprise cationic contrast agents, anionic contrast agents, nonionic contrast agents, or mixtures thereof. In some embodiments, contrast agents comprise radiopaque contrast agents. Radiopaque contrast agents, in some embodiments, comprise iodo-compounds including (S)—N,N'-bis[2-hydroxy-1-(hydroxymethyl)-ethyl]-2,4,6-triiodo-5-lactamido-isophthalamide (Iopamidol) and derivatives thereof.

Compositions Further Comprising Biologically Active Agents

Compositions of the present invention, according to some embodiments, can further comprise one or more biologically active agents in addition to PDGF. Biologically active agents that can be incorporated into compositions of the present invention, in addition to PDGF, can comprise organic molecules, inorganic materials, proteins, peptides, nucleic acids (e.g., genes, gene fragments, small interfering ribonucleic acids [si-RNAs], gene regulatory sequences, nuclear transcriptional factors, and antisense molecules), nucleoproteins, polysaccharides (e.g., heparin), glycoproteins, and lipoproteins. Non-limiting examples of biologically active compounds that can be incorporated into compositions of the present invention, including, e.g., anti-cancer agents, antibiotics, analgesics, anti-inflammatory agents, immunosuppressants, enzyme inhibitors, antihistamines, hormones, muscle relaxants, prostaglandins, trophic factors, osteoinductive proteins, growth factors, and vaccines, are disclosed in U.S. patent application Ser. No. 11/159,533 (Publication No: 20060084602). In some embodiments, biologically active compounds that can be incorporated into compositions of the present invention include osteostimulatory factors such as insulin-like growth factors, fibroblast growth factors, or other PDGFs. In accordance with other embodiments, biologically active compounds that can be incorporated into compositions of the present invention preferably include osteoinductive and osteostimulatory factors such as bone morphogenetic proteins (BMPs), BMP mimetics, calcitonin, or calcitonin mimetics, statins, statin derivatives, fibroblast growth factors, insulin-like growth factors, growth differentiating factors, small molecule or antibody blockers of Wnt antagonists (e.g. sclerostin, DKK, soluble Wnt receptors), and/or parathyroid hormone. In some embodiments, factors also include protease inhibitors, as well as osteoporotic treatments that decrease bone resorption including bisphosphonates, teriparadide, and antibodies to the activator receptor of the NF-kB ligand (RANK) ligand.

Standard protocols and regimens for delivery of additional biologically active agents are known in the art. Additional biologically active agents can introduced into compositions of the present invention in amounts that allow delivery of an appropriate dosage of the agent to the implant site. In most cases, dosages are determined using guidelines known to practitioners and applicable to the particular agent in question. The amount of an additional biologically active agent to be included in a composition of the present invention can depend on such variables as the type and extent of the condition, the overall health status of the particular patient, the formulation of the biologically active agent, release kinetics, and the bioresorbability of the biocompatible matrix. Standard clinical trials may be used to optimize the dose and dosing frequency for any particular additional biologically active agent.

A composition of the present invention, according to some embodiments, can further comprise the addition of additional bone grafting materials with PDGF including autologous bone marrow, autologous platelet extracts, allografts, synthetic bone matrix materials, xenografts, and derivatives thereof.

Methods of Treating Vertebral Bodies

In some embodiments, the present invention provides methods for promoting bone formation in a vertebral body comprising providing a composition comprising a PDGF solution disposed in a biocompatible matrix and applying the composition to at least one vertebral body. In some embodiments, the composition can be applied to a plurality of vertebral bodies. Applying the composition, in some embodiments, comprises injecting at least one vertebral body with the composition. Compositions of the present invention, in some embodiments, are injected into the cancellous bone of a vertebral body. Vertebral bodies, in some embodiments, comprise thoracic vertebral bodies, lumbar vertebral bodies, or combinations thereof. Vertebral bodies, in some embodiments, comprise cervical vertebral bodies, coccygeal vertebral bodies, the sacrum, or combinations thereof.

In another aspect, the present invention provides methods for preventing or decreasing the likelihood of vertebral compression fractures, including secondary vertebral compression fractures by strengthening vertebrae. Preventing or decreasing the likelihood of vertebral compression fractures, according to embodiments of the present invention, comprises providing a composition comprising a PDGF solution disposed in a biocompatible matrix and applying the composition to at least one vertebral body. In some embodiments, applying the composition to at least one vertebral body comprises injecting the composition into the at least one vertebral body.

In some embodiments, a composition of the present invention is applied to a second vertebral body subsequent to vertebroplasty or kyphoplasty of a first vertebral body. In some embodiments, the second vertebral body is adjacent to the first vertebral body. In other embodiments, the second vertebral body is not adjacent to the first vertebral body. In a further embodiment, a composition of the present invention is applied to a third vertebral body subsequent to vertebroplasty or kyphoplasty of a first vertebral body. In some embodiments, the third vertebral body is adjacent to the first vertebral body. In other embodiments, the third vertebral body is not adjacent to the first vertebral body. Embodiments of the present invention additionally contemplate application of compositions provided herein to a plurality of vertebral bodies, including high risk vertebral bodies, subsequent to vertebroplasty or kyphoplasty of a first vertebral body. It is to be understood that first, second, and third vertebral bodies, as used herein, do not refer to any specific position in the vertebral column as methods for inhibiting vertebral compression fractures, including secondary compression fractures, can be applied to all types of vertebral bodies including thoracic vertebral bodies, lumbar vertebral bodies, cervical vertebral bodies, coccygeal vertebral bodies, and the sacrum.

In some embodiments, methods for promoting bone formation in vertebral bodies and preventing or decreasing the likelihood of compression fractures of vertebral bodies further comprise providing at least one pharmaceutical composition in addition to the composition comprising a PDGF solution disposed in a biocompatible matrix and administering the at least one pharmaceutical composition locally and/or systemically. The at least one pharmaceutical composition, in some embodiments, comprises vitamins, such as vitamin D3, calcium supplements, or any osteoclast inhibitor known to one of skill in the art, including bisphosphonates. In some embodiments, the at least one pharmaceutical composition is administered locally. In such embodiments, the at least one pharmaceutical composition can be incorporated into the biocompatible matrix or otherwise disposed in and around a vertebral body. In other embodiments, the at least one pharmaceutical composition is administered systemically to a patient. In one embodiment, for example, the at least one pharmaceutical composition is administered orally to a patient. In another embodiment, the at least one pharmaceutical composition is administered intravenously to a patient.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

Example 1

Preparation of a Composition Comprising a Solution of PDGF and a Biocompatible Matrix A composition comprising a solution of PDGF and a biocompatible matrix was prepared according to the following procedure.

A pre-weighed block of biocompatible matrix comprising β-TCP and collagen was obtained. The β-TCP comprised β-TCP particles having an average diameter ranging from about 100 μm to about 300 μm. The β-TCP particles were formulated with about 20% weight percent soluble bovine type I collagen binder. Such a β-TCP/collagen biocompatible matrix can be commercially obtained from Kensey Nash (Exton, Pa.).

A solution comprising rhPDGF-BB was obtained. rhPDGF-BB is commercially available from Novartis Corporation at a stock concentration of 10 mg/ml (i.e., Lot #QA2217) in a sodium acetate buffer. The rhPDGF-BB is produced in a yeast expression system by Chiron Corporation and is derived from the same production facility as the rhPDGF-BB that is utilized in the products REGRANEX, (Johnson & Johnson) and GEM 21S (BioMimetic Therapeutics) which have been approved for human use by the United States Food and Drug Administration. This rhPDGF-BB is also approved for human use in the European Union and Canada. The rhPDGF-BB solution was diluted to 0.3 mg/ml in the acetate buffer.

The rhPDGF-BB solution can be diluted to any desired concentration according to embodiments of the present invention, including 1.0 mg/ml.

A ratio of about 3 ml of rhPDGF-BB solution to about 1 g dry weight of the (3-TCP/collagen biocompatible matrix was used to produce the composition. In the preparation of the composition, the rhPDGF-BB solution was expelled on the biocompatible matrix with a syringe, and the resulting composition was blended into a paste for placement into a syringe for subsequent injection into a vertebral body.

Example 2

Method of Inhibiting Secondary Vertebral Compression Fractures

Experimental Design and Overview

This prospective, randomized, controlled, single-center clinical trial is to evaluate the efficacy of compositions comprising a PDGF solution disposed in a tricalcium phosphate matrix for inhibiting secondary compression fractures in high risk vertebral bodies (HVBs) at the time of kyphoplasty of vertebral compression fractures. Comparisons are made between vertebral bodies treated with a β-tricalcium phosphate+rhPDGF-BB composition and untreated vertebral bodies. The present study is a pilot, clinical trial to support the proof-or-principle of β-TCP+rh-PDGF-BB to prevent or decrease the likelihood of secondary vertebral compression fractures by increased bone formation in HVBs.

The study is performed on up to a total of 10 patients requiring prophylactic treatment of HVBs at the time of kyphoplasty. Potential patients are screened to determine if they meet the inclusion and exclusion criteria If all entry criteria are achieved, the potential patients are invited to participate in the clinical trial. All patients considered for entry into the study are documented on the Screening Log and reasons for exclusion are recorded.

All patients have undergone kyphoplasty and do not have a symptomatic VCF adjacent to the two vertebral bodies treated in this study. The subject is not to be enrolled into the study if the surgeon determines intraoperatively that the fracture does not meet the fracture enrollment criteria or other fractures exist that would preclude treatment in this protocol.

A total of 10 patients are enrolled and treated in the present study. A first vertebral body adjacent to the kyphoplasty of each patient is injected with 3.0 ml of a composition of β-TCP+0.3 mg/ml of rhPDGF-BB prepared in accordance with Example 1 herein. The second vertebral body adjacent to the kyphoplasty remains untreated and serves as a control. The treated vertebral body may be either cranial or caudal to the kyphoplasty and is determined randomly.

Patients are treated according to the standard protocols and follow-up for kyphoplasty/vertebroplasty. Each patient is examined by the surgeon at 7-14 days, and at 6, 12, 24, and 52 weeks for clinical, radiographic and quantitative computed tomography (QCT). All over-the-counter and prescribed medication usage is recorded. An independent radiologist, unaware of the patients' treatment group assignments, performs QCT analysis to assess bone density. These measurements are documented and analyzed.

All postoperative complications and device-related adverse events are recorded on the appropriate case report form. If a subject experiences a subsequent VCF during the study period or another surgical procedure for a serious adverse event or the investigational device is removed, the subject is monitored for safety until the end of the study. Those subjects who are re-operated and/or have the fracture fixation hardware removed are requested to give permission to examine the explants for histological purposes. All patients are monitored during the 12-month trial and any subject who requests study withdrawal or is withdrawn by the investigator is requested to provide a reason for study discontinuance. Table 1 provides a timeline summary for the present study.

TABLE 1

Study Timeline Survey

| Visit 1 Screening Visit ↓ Within 21 Days of Surgery | Visit 2 Surgical Visit ↓ Within 21 Days of Screening | Visit 3 Post Tx Follow Up ↓ | Visit 4 Post Tx Follow Up ↓ | Visit 5 Post Tx Follow Up ↓ | Visit 6 Post Tx Follow Up ↓ | Visit 7 Post Tx Follow Up ↓ |
|---|---|---|---|---|---|---|
| | Day 0 | Day 7-14 | Week 6 ± 3 days | Week 12 ± 7 days | Week 24 ± 7 days | Week 52 ± 14 days |

The primary endpoint is the bone density at 12 weeks post-operatively measured by QCT scans. Secondary endpoints include subject pain and quality of life assessments.

Surgical Protocol

After patients have been enrolled in the study, satisfying both the inclusion and exclusion criteria, the following surgical protocol is undertaken.

Patients are brought into an operating room (OR) in the standard fashion, and standard methods are used to perform the kyphoplasty procedure with methyl methacrylate cement augmentation of the fractured vertebral body. Standard radiographs are taken of the vertebral bodies treated with kyphoplasty and with preventative bone augmentation treatment.

Following the kyphoplasty treatment, the investigator identifies and qualifies the two levels to be treated with prophylactic bone augmentation. If two (2) qualified vertebral bodies are not available for treatment, as determined at the time of surgery, the patient is considered a screen failure and not enrolled into the study.

Upon identification of the two HVBs, the investigator requests that the randomization code be opened to determine the study treatment administered. The randomization code specifies treatment with the β-TCP+rhPDGF composition either proximally or distally in relation to the level treated with kyphoplasty. The other HVB remains untreated.

The β-TCP+rhPDGF composition is mixed according to the procedure provided in Example 1. Once mixed, the paste is loaded into a syringe for injection using aseptic technique. Once the β-TCP+rhPDGF composition is mixed, the clinician waits about 10 minutes prior to implantation. A new sterile mixing device (spatula) is used for each mix. The investigator directs the assistant who performs the mixing to record the cumulative amount of implanted composition, as well as the residual amount of composition not implanted. The amount of composition is calculated and documented using qualitative relative measurements (⅓, ⅔, All).

An 8 to 16 gauge JAMSHIDI® needle available from Cardinal Health of Dublin, Ohio is inserted through an extrapedicular approach into the vertebral bodies requiring prophylactic treatment. The wire is passed through the JAMSHIDI® needle and the JAMSHIDI® needle through the stylet over the wire The appropriate mixed preparation is injected into the subject vertebral body. Care should be taken to minimize leakage of the paste outside of the vertebral body.

Figure 2:
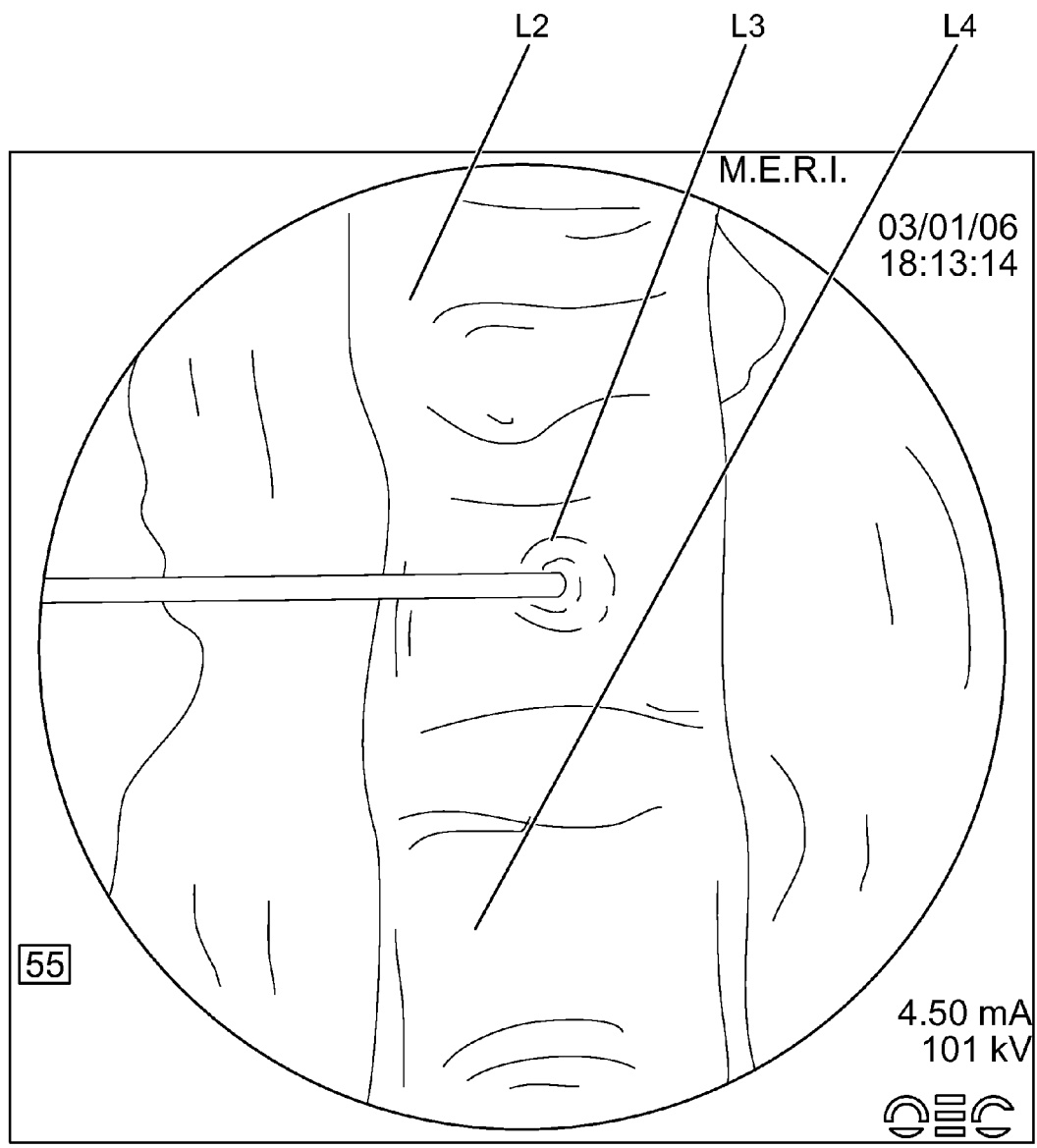
FIG. 2 is a radiograph illustrating injection of a composition into a vertebral body according to an embodiment of the present invention.

Contrast agents, according to embodiments of the present invention, can assist in identifying the leakage of the paste outside the vertebral body. FIG. 1 illustrates a syringe and related apparatus penetrating tissue overlaying a vertebral body to deliver a composition of the present invention to the vertebral body. FIG. 2 is a radiograph illustrating injection of a composition of the present invention into the vertebral body of the L3 vertebra according to one embodiment.

The instrumentation is removed. Thorough irrigation and standard wound closure techniques are employed.

Follow-up Evaluations

Patients are seen for post-operative evaluations at days 7-14, and at 6 (±3 days), 12 (±7 days), 24 (±7 days), and 52 (±14 days) weeks post-surgery. Routine evaluations and procedures are performed during the follow-up period, as specified in the study flowchart of Table 2 below.

Assessment of Effectiveness

Outcome data is collected from this study on findings derived from radiographs, QCTs, and from direct examination of function. The schedule of these measurements is provided in Table 3.

TABLE 3

Frequency of Radiographic and Functional Assessments

| Timepoint | Study Parameters | | | |
|---|---|---|---|---|
| | Plain film radiographs | Qualitative CT Scans | Pain | Function |
| Prior to Treatment | X | X | X | X |
| Immediately Post-Treatment | X | | | |
| Day 7-14 | | X | | |
| Week 6 | X | X | X | X |
| Week 12 | X | X | X | X |
| Week 24 | X | X | X | X |
| Week 52 | X | X | X | X |

Vertebral bodies injected with a β-TCP+rhPDGF composition are expected to display increased bone mineral density (BMD) in comparison to untreated vertebral bodies. Increased bone mineral density in a vertebral body can render the vertebral body less susceptible to fractures including secondary fractures induced by kyphoplasty/vertebroplasty operations.

TABLE 2

Study Flow Chart and Follow-up Assessments

| | | | Post-Treatment Follow-Up Evaluations | | | | |
|---|---|---|---|---|---|---|---|
| Procedure | Screening Visit 1 | Surgery Visit 2 Day 0 | Visit 3 Day 7-14 | Visit 4 Week 6 ± 3 Days | Visit 5 Week 12 ± 7 Days | Visit 6 Week 24 ± 7 Days | Visit 7 Week 52 ± 14 Days |
| Informed Consent | X[1] | | | | | | |
| Screening Log | X | | | | | | |
| Medical History | X | | | | | | |
| Physical Examination of Spine | X | X | X | X | X | X | X |
| Subject Eligibility Criteria Verification | X | X | | | | | |
| Identification of High-Risk Vertebral Bodies | X | | | | | | |
| Randomization | | X | | | | | |
| Kyphoplasty and Preventative Bone Augmentation | | X | | | | | |
| Volume of Graft Material Placed | | X | | | | | |
| Qualitative CT Assessments[2] | | X | | X | X | X | |
| Plain Radiographic Assessments | X | X | | X | X | X | X |
| Adverse Events/Complications | | X | X | X | X | X | X |
| Concomitant Medications Review | X | X | X | X | X | X | X |

[1]Must occur prior to any study-specific procedures.
[2]Quantitative Computed Tomography (QCT) is performed according to standard protocol to obtain BMD data which is determined by the designated musculoskeletal radiologist.

Example 3

Method of Inhibiting Vertebral Compression Fractures in Osteoporotic Individuals A method of inhibiting vertebral compression fractures in osteoporotic individuals comprises promoting bone formation in vertebral bodies through treatment with compositions comprising a PDGF solution disposed in a biocompatible matrix such as β-tricalcium phosphate.

Compositions of the present invention are mixed in accordance with that provided in Example 1. The concentration of PDGF in the PDGF solutions ranges from 0.3 mg/ml to 1.0 mg/ml. Once mixed, the composition is loaded into a syringe for injection using aseptic technique. The surgeon waits about 10 minutes prior to implantation. A new sterile mixing device (spatula) is used for each mix.

The JAMSHIDI® needle is inserted through an extrapedicular approach into the vertebral bodies requiring prophylactic treatment. Vertebral bodies requiring prophylactic treatment, in some embodiments, comprise high risk vertebral bodies including vertebral bodies T5 through T12 and L1 through L4. The wire is passed through the JAMSHIDI® needle and the JAMSHIDI® needle through the stylet over the wire The mixed composition is injected into the subject vertebral body. Care is taken to minimize leakage of the paste outside of the vertebral body. A plurality of vertebral bodies are treated according to the present example. Osteoporotic patients receiving this treatment have a lower incidence of vertebral compression fractures than untreated osteoporotic patients.

Example 4

Evaluation of the Chronic Safety of rh-PDGF-BB Combined with Collagen/β-tricalcium Phosphate Matrix in a Rabbit Paravertebral Implant Model Experimental Design and Overview This study evaluated the safety of implanting injectable rhPDGF-BB/collagen/β-TCP material in a paravertebral intramuscular site adjacent to the spine of rabbits. The animals were observed for signs of neurotoxicity, and the implant sites with adjacent vertebral bodies and spinal cord were examined histologically to document tissue-specific responses to the material.

The study protocol and animal care was approved by the local IACUC and conducted according to AAALAC guidelines. Twelve (12) naïve, female, albino New Zealand rabbits weighing≥2.5 kg were assigned to one of 4 groups: 0.3 mg/ml PDGF; 1.0 mg/ml PDGF; rubber; or acetate buffer. PDGF treated rabbits received 0.2 cc implants of appropriately concentrated rhPDGF-BB in matrix injected into a 1 cm pocket in the right paravertebral muscle adjacent to the L4-L5 vertebral bodies while high density polyethylene (HDPE) was implanted in a similar incision in the left paravertebral muscles near L2-L3 of the same animals. Rabbits in the sodium acetate buffer group received sodium acetate buffer in place of the PDGF+matrix implant, while those in the rubber group received only rubber in the right paravertebral muscle. One rabbit in each group was sacrificed at 29, 90, and 180 days post-surgery.

Body weights were measured prior to surgery and biweekly following surgery for the duration of the study. Radiographs were taken prior to surgery, immediately following surgery, and immediately prior to sacrifice. Digital photography of the surgical sites was performed during surgery and at the study end points. Weekly clinical observations of the implant sites were recorded for signs of erythema, edema, and inflammation and for signs of neurotoxicity, such as ambulatory changes. At necropsy, each implant site along with the adjacent vertebral body and spinal cord were harvested en bloc, fixed in formalin, and prepared for decalcified, paraffin embedded histopathological analysis.

Materials

The dosages of rhPDGF-BB tested in this study included 0.3 mg/ml and 1.0 mg/ml in 20 mM sodium acetate buffer, pH 6.0+/−0.5. The matrix material consisted of 20% lyophilized bovine type I collagen and 80% β-TCP with a particle size of 100-300 μm (Kensey Nash Corporation). Negative control material consisted of high-density polyethylene (HDPE) and positive control material consisted of black rubber. Immediately prior to surgery, the rhPDGF-BB and control solutions were mixed with matrix material in a 3:1 liquid to mass ratio.

Briefly, the PDGF solution was allowed to saturate the material for about 2 minutes then was manually mixed for about 3 minutes to generate a paste-like consistency. The homogeneous distribution of rhPDGF-BB throughout the mixed material using this mixing technique was confirmed by eluting the PDGF from samples of similar mass and then quantifying the PDGF by ELISA (R&D Systems).

Results

Following manual mixing of 0.3 mg/ml rhPDGF-BB with the collagen/β-TCP matrix, the homogeneity of rhPDGF-BB throughout the mixed material was confirmed within +/−4% error across samples.

All animals recovered from surgery, and at the time of this writing, all clinical observations were reported to be normal with no signs of neurotoxicity or abnormal wound healing at the surgical sites. Two animals treated with sodium acetate buffer and matrix control exhibited minor scabbing at the surgical wounds which healed completely. One animal that received 0.3 mg/ml rhPDGF-BB exhibited slight erythema at the surgical site 3-4 days after surgery and then returned to normal appearance. A histopathological analysis of test article implant sites 29 days post-surgery indicated a mild amount of tissue in-growth into the implanted test materials and a mild inflammatory response. No ectopic or abnormal bone formation was observed in the vertebral bodies adjacent to the implant sites. These findings are summarized in Table 4 and compared with ratings for negative control HDPE implant sites.

TABLE 4

Summary of Histopathology Findings at Implant Sites 29 Days After Surgery

| [PDGF-BB] (mg/ml) | Macrophages | MGCs | Tissue In-growth | Ectopic Bone | Exostosis |
|---|---|---|---|---|---|
| 0.3 | 3, 1(NC) | 2, 0(NC) | 2, 0(NC) | 0, 0(NC) | 0, 0(NC) |
| 1.0 | 2, 2(NC) | 2, 0 (NC) | 2, 0(NC) | 0, 0(NC) | 0, 0(NC) |

NC = Negative Control; MGC = multinucleated giant cells; Bioreactivity scale: 0 = Absent, 1 = Minimal/Slight, 2 = Mild, 3 = Moderate, 4 = Marked/Severe Preliminary evidence from this study based on clinical observations, suggests that collagen/β-tricalcium phosphate combined with either 1.0 mg/ml, 0.3 mg/ml rhPDGF-BB, or sodium acetate buffer does not elicit any acute or chronic neurotoxic effects. Histopathological assessment of the implant sites 29 days post-surgery indicated a normal and expected mild amount of tissue in-growth into the implanted material and a mild inflammatory response. No ectopic bone formation, exostosis, or abnormal bone resorption was observed at any of the implant sites. Based on observations of the animals treated in this study, collagen/β-tricalcium phosphate combined with either 1.0 mg/ml, 0.3 mg/ml rhPDGF-BB is safe to use when injected in close proximity to the spinal column.

Example 5

Evaluation of the Safety of PDGF-BB Combined with a Bovine Type I Collagen/β-TCP Matrix for Vertebral Therapy This study evaluated the safety of a composition comprising rhPDGF-BB combined with a biocompatible matrix comprising β-tricalcium phosphate and type I collagen for bone augmentation following injection of the composition into vertebral bodies of baboons. Experimental Design A total of 6 female baboons (*Papio anubis*) of 18 to 21 years of age were studied, each baboon being assigned to one of two treatment groups as provided in Table 5. During the study, the animals were imaged and analyzed using radiography, quantitative computed tomography (QCT), magnetic resonance imaging (MRI) techniques, terminal histology and non-GLP microcomputed tomography (microCT).

Figure 3:
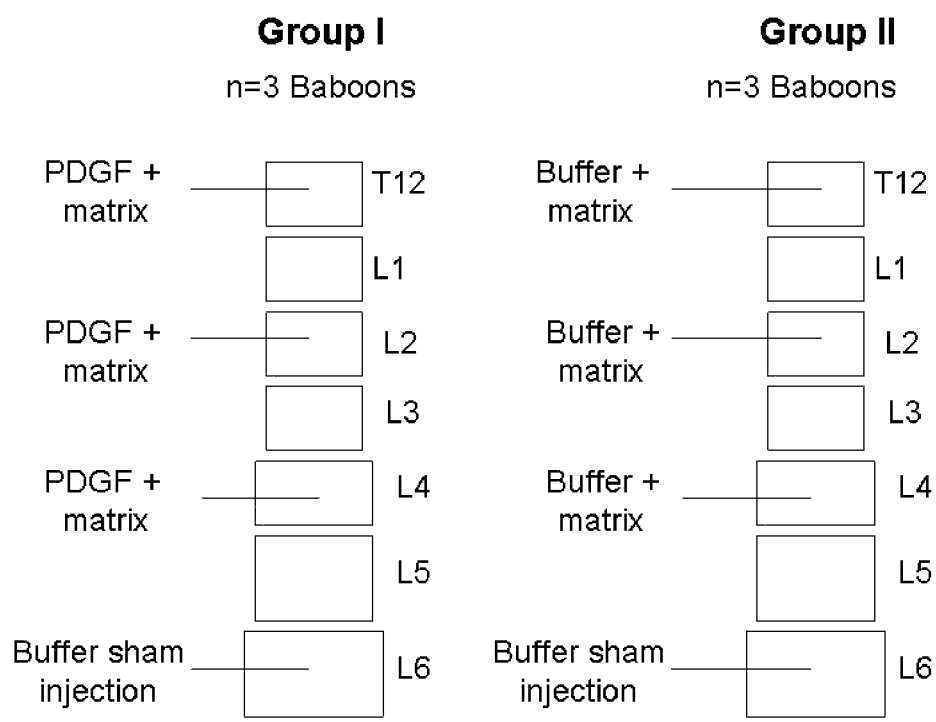
FIG. 3 illustrates vertebrae receiving compositions of the present invention according to one embodiment of the present invention.

Four vertebral levels (T12, L2, L4 and L6) were investigated in each animal. Each animal of Group I received an injection of about 0.5 cc of a 1.0 mg/ml rhPDGF-BB+collagen/β-TCP (matrix) composition into each of the T12, L2 and L4 vertebral bodies. The 1.0 mg/ml rhPDGF-BB+collagen/β-TCP (matrix) compositions were prepared as set forth in Example 1 hereinabove. Each animal of Group II received an injection of about 0.5 cc of a sodium acetate buffer+collagen/β-TCP (matrix) composition into each of the T12, L2, and L4 vertebral bodies. Animals of each group I and II additionally received an injection of about 0.5 cc of a sodium acetate buffer into the L6 vertebral bodies. Therefore, a total of four (4) vertebral bodies per animal received an injection. FIG. 3 summarizes the injection strategy of the present study. Documentation of the treatments in each animal was recorded on study forms.

Surgery was conducted using a percutaneous, fluoroscopically guided approach. The procedure was performed similar to a vertebroplasty, except that an injectable 1.0 mg/ml rhPDGF-BB+collagen/β-TCP matrix or appropriate control treatment was injected. About 0.5 cc of a rhPDGF-BB+collagen/β-TCP material, control material, or buffer was injected into each vertebral body as described above. Each animal was provided anesthesia during the surgery.

A. Assignment to Dose Group

Three animals were assigned to treatment groups by a manual scheme designed to achieve similar group mean body weights.

B. Assignment to Surgery Days

Animals were assigned to one of two surgery days (Day I or Day II). For each animal, a coin flip determined assignment into the Day I group or the Day II group. This process was continued until each of the days was filled with three animals. The animal numbers, their dosing group assignments, and surgery days were recorded. The animal treatment groups were known to the study monitors and study director. The radiologists and histopathologist were blind to the treatment groups.

C. In-Vivo Observations And Measurements
Clinical Observations

Animals were observed within their cages daily throughout the study. Recording of cageside observations was commenced after the pre-selection criteria was completed and is continued until the end of study. Each animal was observed for changes in general appearance and behavior, including changes in ambulation. Each animal was observed for evidence of menstrual cycling over the course of the study. The cycling readings were performed non-GLP and were recorded in the Southwest Foundation for Biomedical Research (SFBR) animal database.

Treatment of the animals was in accordance with SFBR standard operating procedures (SOPs), which adhere to the regulations outlined in the USDA Animal Welfare Act (9 CFR, Parts 1, 2 and 3) and the conditions specified in The Guide for Care and Use of Laboratory Animals (ILAR publication, 1996, National Academy Press). The study animals were observed and were recorded at least once daily for signs of illness or distress, including changes in ambulation, and any such observations were reported to the responsible veterinarian and study director.

Body Weight

Body weights were measured at the initial health check, prior to surgery, and prior to follow up radiographs. Food was withheld prior to sedation and subsequent body weight measurements.

Food Consumption

Except when animals were fasting for study procedures, food consumption was qualitatively assessed daily for each animal (as part of the cageside observations), beginning at least 7 days prior to surgery. Each animal was provided a full

TABLE 5

Summary of Treatments for Injection of rhPDGF-BB+ Collagen/β-TCP Matrix in Vertebral Bodies of Baboons

| Group | Dose | Timepoints | Analyses |
| --- | --- | --- | --- |
| I | 1.0 mg/ml PDGF + collagen/β-TCP matrix. L6 received sodium acetate buffer only | Pre- and post-surgery, 1 and 3 months, (optionally 6 months) | QCT, MRI, Clinical Observations, Serum Chemistry and Hematology (Pre- and post-surgery, and at 1 month, 3 months, and 6 months post-surgery), Body Weights, Radiography, Histology, non-GLP microCT |
| II | 20 mM sodium acetate buffer, pH 6.0 + collagen/β-TCP matrix. L6 received sodium acetate buffer only | Pre- and post-surgery, 1 and 3 months, (optionally 6 months) | QCT, MRI, Clinical Observations, Serum Chemistry and Hematology (Pre- and post-surgery, and at 1 month, 3 months, and 6 months post-surgery), Body Weights, Radiography, Histology, non-GLP microCT | feeder of food once a day (non-sedation days) and the amount eaten was documented as per SFBR SOPs. On sedation days, the animals were fed once each day when they recovered from anesthesia.

D. Fluoroscopy, Photography, Radiography, MRI and QCT Imaging

Non-GLP digital photographs were taken of the injection sites pre-operatively, immediately post-operatively, and at 1, 3, 6, and 9 months post-operatively.

Anteroposterior and lateral radiographs were taken pre-treatment and immediately following surgery as well as at about 1, 3, 6, and 9 months post-operatively. For anteroposterior radiographs, the animals were placed on their backs in supine position with their legs supported. For lateral radiographs, the animals were positioned lying on their left sides with arms and legs supported. Energy (kV) and intensity (mA) settings for each position and animal were recorded.

Non-GLP fluorographs were captured intraoperatively before, during, and after injection of the test and control articles into the vertebrae of the animals. Fluorographs were not assessed as an outcome of this study, but enable the surgeon to accurately insert the introduction needle into the vertebral bodies during surgery.

Magnetic resonance imaging (MRI) was performed to image the spine of each animal pre-operatively and within 4 to 10 days post-operatively. MRI was additionally performed to image the spine of each animal at about 1, 3, 6, and 9 months post-operatively. MRI sessions consisted of T1 and T2-weighted scans.

Quantitative computed tomography imaging (QCT) was performed to image the spine of each animal pre-operatively and within 4 to 10 days post-operatively. QCT was additionally performed to image the spine of each animal at about 1, 3, 6, and 9 months post-operatively. Scans consisted of a series of contiguous cross-sectional slices of the torso from the caudal endplate of the 11th thoracic vertebrae to the cranial endplate of the sacrum.

QCT was also used to obtain 3 mm thick cross sectional images of injected and intervening untreated vertebral bodies of each baboon 1 week prior to surgery (pre-surgical) and at 1, 4, and 12 weeks post surgery. A total of 5-8 slices were required to fully image each vertebral body. The DICOM (digital imaging and communications in medicine) format images produced by the QCT were transferred and converted to a file format for 3-dimensional volumetric analysis using software developed by Scanco AG (Bassersdorf, Switzerland). Volumetric bone mineral density (vBMD) of the anterior compartment of each vertebral body was determined by manually selecting a region of interest (ROI) that excluded the cortical shell in each slice. The evaluation software created a z-stack of the individual slices and ROI's before extracting the volumetric ROI and calculating volumetric density in arbitrary units derived from the gray-scale intensity in the images and a percent change from the baseline scans was calculated. One-way repeated measures ANOVA with Tukey's post-hoc test was used to determine the presence of any statistically significant changes in vBMD for animals of Group I and Group II from pre-surgical or 1 wk post-surgical to the conclusion of the study.

The radiographs, MRI, and QCT images were evaluated by one board certified clinical radiologist and one qualified associate to provide a consensus assessment of the neuropathological, osteopathological and surrounding soft tissue pathological outcomes resulting from the treatments of the vertebrae. The evaluation consisted of a qualitative examination of each image for abnormalities of the bone and of the neural tissues and adjacent surrounding soft tissues. The radiologist followed the Radiology Assessment Protocol to evaluate the radiology data.

E. Clinical Pathology Evaluation

Serum Chemistry

About 3 ml whole blood was collected into containers without anticoagulant pre-surgery and post-surgery. About 3 ml whole blood was also collected into containers without anticoagulant at about 1, 3, 6, and 9 months post-operatively. The animals were fasted overnight prior to blood collection for serum chemistry. Serum was analyzed for the following parameters set forth in Table 6.

TABLE 6

Serum Analysis

| | |
|---|---|
| Sodium | Phosphorus |
| Potassium | Glucose |
| Chloride | Urea nitrogen (BUN) |
| Total carbon dioxide (bicarbonate) | Creatinine |
| Total bilirubin | Total protein |
| Alkaline phosphatase (AP) | Albumin |
| Lactate dehydrogenase (LDH) | Globulin |
| Aspartate aminotransferase (AST) | Albumin/globulin ratio |
| Alanine aminotransferase (ALT) | Cholesterol |
| Gamma-glutamyltransferase (GGT) | Triglycerides |
| Calcium | BUN/CREAT Ratio |
| Anion Gap | Direct Bilirubin |
| CPK | |

Hematology

About 3 ml of blood was collected in EDTA-containing tubes pre-surgery and post-surgery. About 3 ml of blood was also collected in EDTA-containing tubes at 1, 3, 6, and 9 months post-surgery. The whole blood samples were analyzed for the following parameters set forth in Table 7.

TABLE 7

Blood Analysis

| | |
|---|---|
| Red blood cell (RBC) counts | Mean corpuscular hemoglobin (MCH) |
| White blood cells (WBCs) (total and differential*) | Mean corpuscular hemoglobin concentration (MCHC) |
| Hemoglobin concentration | Mean corpuscular volume (MCV) |
| Hematocrit | Platelet counts (Plt) |
| RDW | Abnormal blood cell morphology |

*Includes polysegmented neutrophils, band cells, lymphocytes, monocytes, basophils, eosinophils.

Serum Collection for Analysis by Sponsor or SFBR

About 14 ml of blood was collected into non-additive (i.e., "clot") tubes from all animals once pre-surgery and post-surgery. About 14 ml of blood was also collected into non-additive (i.e., "clot") tubes from all animals at 1, 3, 6, and 9 months post-surgery. The blood was centrifuged to obtain serum and divided into two aliquots. The serum is stored at −70° C. or lower.

Anatomic Pathology

All animals are humanely sacrificed at the end of the study. A gross necropsy is conducted on each animal sacrificed in a moribund or diseased condition to determine the cause and/or nature of the moribund or diseased condition.

Necropsy

A complete necropsy is conducted under the supervision of the study pathologist on the sacrificed animals in a moribund or diseased condition during the study to determine the cause and/or nature of the moribund or diseased condition. A standard necropsy includes an examination of external surfaces and orifices, extremities, body cavities, and internal organ/tissues. All of the treated vertebrae are collected and are examined for abnormalities. A brief morphologic description of all macroscopic abnormalities is recorded on individual necropsy forms.

Tissue Collection and Preservation

The following tissues and organs are obtained at sacrifice and are preserved in 10% neutral-buffered formalin (except for the eyes, which were preserved in Bouin's Solution for optimum fixation). Each tissue or organ specimen is then embedded in paraffin for preservation purposes and is archived at a sponsor-approved site or used to help determine the cause of death.

For all baboons, all treated and adjacent untreated vertebrae (T12 thru L6) are individually harvested en bloc including the spinal cord and spinal canal and are appropriately identified as to the treatment received. The T12 vertebral body is identified by leaving a minimum of 2 cm of the ribs attached to the bone. All bone specimens are placed in formalin fixative in preparation for plastic embedding.

Each of the soft tissues or organ specimens is embedded in paraffin for preservation purposes and are archived. A summary of the tissue samples to be collected is provided in Table 8.

TABLE 8

Summary of Tissue Samples to be Collected at Necropsy

Cardiovascular
    Aorta
    Heart
Digestive
    Salivary Gland (mandibular)
    Tongue
    Esophagus
    Stomach
    Small Intestine
    Duodenum
    Jejunum
    Ileum
    Large Intestine
    Cecum
    Colon
    Rectum
    Pancreas
    Liver
    Gallbladder
Respiratory
    Trachea
    Lung (including bronchi)
Lymphoid/Hematopoietic
    Bone Marrow (sternum)
    Thymus
    Spleen
    Lymph Nodes
        Axillary
        Mandibular
        Mesenteric
Endocrine
    Adrenals
    Pituitary
    Thyroid/Parathyroids*
Urogenital
    Kidneys
    Urinary Bladder
    Ovaries
    Uterus
    Cervix
    Vagina TABLE 8-continued Summary of Tissue Samples to be Collected at Necropsy Skin/Musculoskeletal
    Skin/Mammary Gland (males and females)
    Bone (femoral head)
    Bone (7th rib)
    Skeletal Muscle (thigh)
    Knee joint
    Shoulder joint
    Mandible
    Right Foot
    Left Ankle
    Right Hand
    Left Wrist
    Spine from T12 to L7/Sacrum - separated
Nervous/Special Sense
    Eyes with optic nerve
    Sciatic Nerve
    Brain
    Optic chiasm
    Cerebrum
    Cerebellum
    Medulla
    Pons
    Spinal Cord (thoracic)
Other
    Animal Number Tattoo
    Gross Lesions
    Lacrimal glands

*The occasional absence of the parathyroid gland from the routine tissue section will not require a recut of the section.

Vertebral bodies injected with a composition comprising a rhPDGF-BB solution disposed in a β-TCP/collagen matrix displayed the formation of normal bone with no adverse neurotoxic effects. Moreover, soft tissues adjacent to vertebral bodies receiving a composition comprising a rhPDGF-BB solution disposed in a β-TCP/collagen matrix did not demonstrate abnormalities resulting from the administration of the rh-PDGF/matrix composition.

Figure 4:
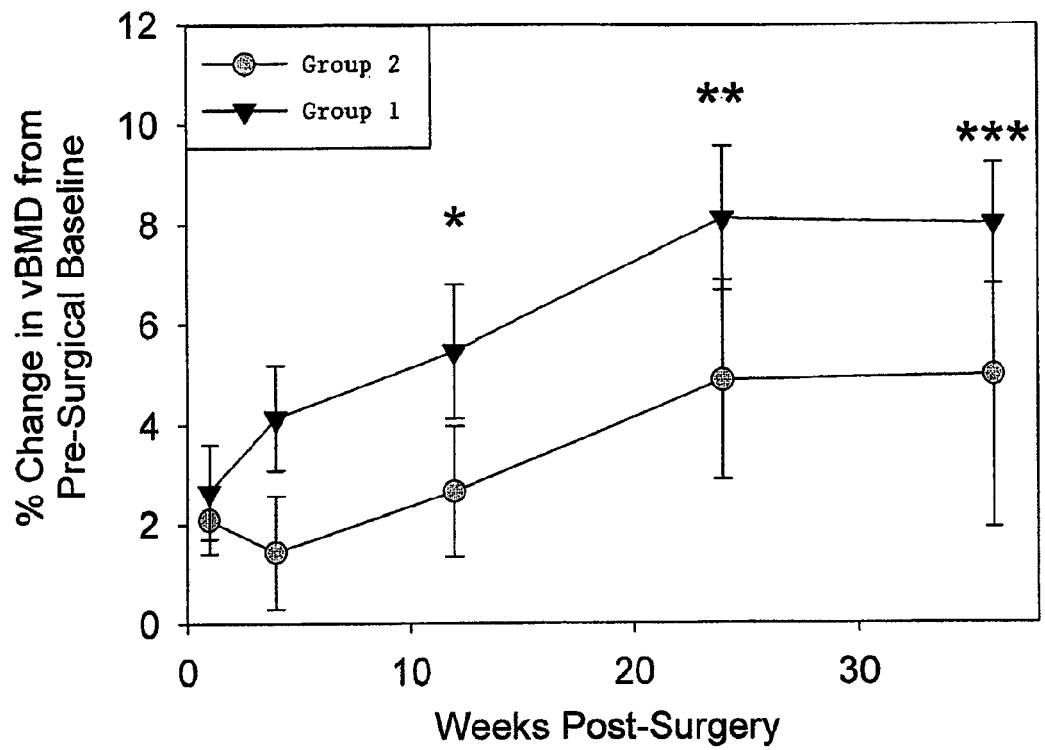
FIG. 4 illustrates percent change in volumetric bone mineral density for vertebral bodies receiving a composition comprising 1.0 mg/ml of rhPDGF-BB disposed in a β-TCP/collagen matrix in comparison with vertebral bodies receiving a composition comprising 20 mM sodium acetate buffer disposed in a β-TCP/collagen matrix according to one embodiment of the present invention.

Furthermore, vertebral bodies injected with a composition comprising a rhPDGF-BB solution disposed in a β-TCP/collagen matrix additionally displayed increased volumetric bone mineral densities. FIG. 4 illustrates percent change in volumetric bone mineral density (vBMD) for vertebral bodies of animals of Group I and Group II. Each data point in FIG. 4 represents an average of all vertebral bodies treated within each group. For example, the first data point in FIG. 4 for Group I is the average of nine vertebral body measurements (T12, L2, and L4 for each of three animals in Group I) taken after injection of the rhPDGF-BB matrix composition into the vertebral bodies. Similarly, the first data point in FIG. 4 for Group 2 is the average of nine vertebral body measurements (T12, L2 and L4 for each of three animals in Group II) taken after injection of a collagen/β-TCP matrix into the vertebral bodies.

As illustrated in FIG. 4, vertebral bodies treated with a composition comprising a rhPDGF-BB solution disposed in a β-TCP/collagen matrix (Group I) demonstrated a steady increase in vBMD over the course of the study, the increase in vBMD becoming statistically significant over the 1 week post-operative level by the third month [2.64%+/−1.16 (week 1) v. 5.93%+/−1.33 (week 12); p=0.023]. vBMD continued to increase through the sixth month of the study before reaching a plateau at the ninth month. Vertebral bodies treated with a composition comprising 20 mM sodium acetate buffer disposed in the β-TCP/collagen matrix (Group II), however, did not demonstrate significant increases in vBMD over the course of the study.

Figure 5:
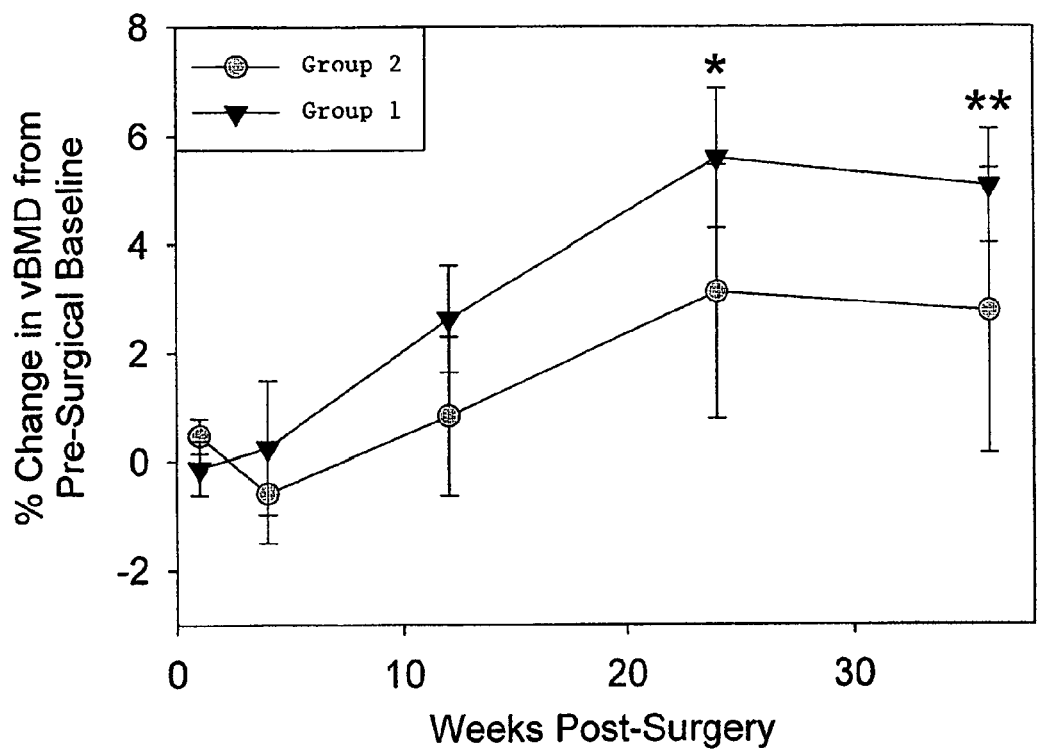
FIG. 5 illustrates percent change in volumetric bone mineral density for vertebral bodies receiving a composition comprising 1.0 mg/ml of rhPDGF-BB disposed in a β-TCP/collagen matrix in comparison with vertebral bodies receiving a composition comprising 20 mM sodium acetate buffer disposed in a β-TCP/collagen matrix according to one embodiment of the present invention.

Additionally, FIG. 5 illustrates percent change in vBMD for vertebral bodies of animals of Group I and Group II wherein the injected β-TCP/collagen matrix is subtracted from the volumetric bone mineral density analysis. As in FIG. 4, each data point in FIG. 5 represents an average of all vertebral bodies treated within each group.

As illustrated in FIG. 5, vertebral bodies treated with a rhPDGF-BB matrix composition (Group I) demonstrated increases in vBMD. The subtraction of the β-TCP/collagen matrix from the volumetric bone mineral density analysis provided a clear indication that vBMD increased throughout all regions of the vertebral bodies of Group I as opposed to regions local to the injection site of the rhPDGF-BB matrix composition.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

The invention claimed is:

1. A method for increasing bone density in a vertebral body in an individual comprising:
applying a composition to the vertebral body,
wherein the composition consists of a biocompatible matrix having incorporated therein a solution consisting of platelet derived growth factor (PDGF) at a concentration in a range of about 0.1 mg/ml to about 1.0 mg/ml in a buffer, wherein the biocompatible matrix consists of (i) particles of a porous calcium phosphate in a range of about 100 µm to about 5 mm in size or (ii) (a) particles of a porous calcium phosphate in a range of about 100 µm to about 5 mm in size and (b) collagen, and
wherein the calcium phosphate comprises interconnected pores.

2. The method of claim 1, wherein the vertebral body is a high risk vertebral body.

3. The method of claim 1, wherein the vertebral body is an osteoporotic vertebral body.

4. The method of claim 1, wherein the individual is a medically compromised patient.

5. The method of claim 1, wherein the method is for prevention or decreasing the likelihood of a vertebral compression fracture.

6. The method of claim 1, wherein the PDGF is at a concentration of about 0.3 mg/ml.

7. The method of claim 1, wherein the PDGF comprises PDGF-BB.

8. The method of claim 1, wherein the PDGF comprises rhPDGF-BB or a fragment thereof, wherein the fragment is selected from the group consisting of amino acid sequences 1-31, 1-32, 33-108, 33-109 and 1-108 of the entire B chain.

9. The method of claim 8, wherein the rhPDGF-BB comprises at least 65% of intact rhPDGF-BB.

10. The method of claim 1, wherein the calcium phosphate consists of particles having an average diameter in a range from about 100 µm to about 300 µm.

11. The method of claim 1, wherein the calcium phosphate consists of particles having an average diameter in a range from about 1000 µm to about 2000 µm.

12. The method of claim 1, wherein the calcium phosphate consists of particles having an average diameter in a range from about 250 µm to about 1000 µm.

13. The method of claim 1, where the calcium phosphate is β-tricalcium phosphate.

14. The method of claim 1, wherein the calcium phosphate has a porosity greater than about 50%.

15. The method of claim 1, wherein the calcium phosphate has a porosity greater than about 90%.

16. The method of claim 1, wherein the composition has a porosity that facilitates cell migration into the calcium phosphate.

17. The method of claim 16, wherein the porosity comprises macroporosity.

18. The method of claim 1, wherein the composition is resorbable such that at least 90% of the calcium phosphate is resorbed within one year of being implanted.

19. The method of claim 1, wherein the incorporated liquid is adsorbed or absorbed to the biocompatible matrix.

20. The method of claim 1, wherein the composition is flowable.

21. The method of claim 1, wherein the matrix consists of the particles of the porous calcium phosphate.

22. The method of claim 21, wherein the calcium phosphate has a porosity greater than 90%.

23. The method of claim 21, wherein the PDGF comprises PDGF-BB or a fragment thereof, wherein the fragment is selected from the group consisting of amino acid sequences 1-31, 1-32, 33-108, 33-109 and 1-108 of the entire B chain, wherein the composition has a porosity that facilitates cell migration into the composition.

24. The method of claim 1, wherein the matrix consists of the particles of the porous calcium phosphate and collagen.

25. The method of claim 24, wherein the PDGF comprises PDGF-BB or a fragment thereof, wherein the fragment is selected from the group consisting of amino acid sequences 1-31, 1-32, 33-108, 33-109 and 1-108 of the entire B chain, wherein the calcium phosphate has a porosity greater than about 50%.

26. The method of claim 24, wherein the PDGF comprises PDGF-BB or a fragment thereof, wherein the fragment is selected from the group consisting of amino acid sequences 1-31, 1-32, 33-108, 33-109 and 1-108 of the entire B chain, wherein the calcium phosphate has interconnected pores, and wherein the composition has a porosity that facilitates cell migration into the composition.

27. The method of claim 24, wherein the collagen comprises Type I collagen.

28. The method of claim 24, wherein the ratio of calcium phosphate:collagen is about 80:20.

29. The method of claim 1, wherein applying the composition comprises injecting the composition into the vertebral body.

* * * * *